United States Patent
Sowards et al.

(10) Patent No.: US 12,220,219 B2
(45) Date of Patent: Feb. 11, 2025

(54) STEERABLE FIBER OPTIC SHAPE SENSING ENABLED ELONGATED MEDICAL INSTRUMENT

(71) Applicant: Bard Access Systems, Inc., Salt Lake City, UT (US)

(72) Inventors: Steffan Sowards, Salt Lake City, UT (US); Anthony K. Misener, Bountiful, UT (US); Anthony D. Decheek, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 313 days.

(21) Appl. No.: 17/535,406

(22) Filed: Nov. 24, 2021

(65) Prior Publication Data

US 2022/0160209 A1    May 26, 2022

Related U.S. Application Data

(60) Provisional application No. 63/119,858, filed on Dec. 1, 2020, provisional application No. 63/117,901, filed on Nov. 24, 2020.

(51) Int. Cl.
*A61B 5/06* (2006.01)
*A61B 1/00* (2006.01)
(Continued)

(52) U.S. Cl.
CPC .......... *A61B 5/065* (2013.01); *A61B 1/00098* (2013.01); *A61B 1/0055* (2013.01);
(Continued)

(58) Field of Classification Search
None
See application file for complete search history.

(56) References Cited

U.S. PATENT DOCUMENTS

| 3,493,288 A | 2/1970 | Oltman et al. |
| 4,768,855 A | 9/1988 | Nishi et al. |
| (Continued) | | |

FOREIGN PATENT DOCUMENTS

| CA | 3025240 A1 | 11/2017 |
| DE | 102016109601 A1 | 11/2017 |
| (Continued) | | |

OTHER PUBLICATIONS

PCT/US2021/044216 filed Aug. 2, 2021 International Search Report and Written Opinion dated Nov. 18, 2021.
(Continued)

*Primary Examiner* — Katherine L Fernandez
(74) *Attorney, Agent, or Firm* — Rutan & Tucker LLP

(57) ABSTRACT

Disclosed herein is a system, apparatus and method directed to placing a medical instrument in a vasculature of a patient body, where the medical instrument includes an optical fiber having one or more core fibers. The system also includes a console having non-transitory computer-readable medium storing logic that, when executed, causes operations of providing an incident light signal to the optical fiber, receiving a reflected light signal of the incident light, processing the reflected light signals associated with the optical fiber and determining a location of a distal tip of the medical instrument within the patient body. The medical instrument may be steerable in one of various methods including having a predetermined curvature, a distal tip that is magnetic, magnetized, metallic or ferrous and is steerable by an external magnetic device or a having a variable stiffness at a distal tip.

19 Claims, 23 Drawing Sheets

(51) Int. Cl.
*A61B 1/005* (2006.01)
*A61B 1/05* (2006.01)
*A61B 1/07* (2006.01)
*A61B 5/00* (2006.01)
*A61M 25/01* (2006.01)
*A61B 5/283* (2021.01)
*A61B 34/20* (2016.01)

(52) U.S. Cl.
CPC .................. *A61B 1/05* (2013.01); *A61B 1/07* (2013.01); *A61B 5/6852* (2013.01); *A61M 25/0102* (2013.01); *A61M 25/0105* (2013.01); *A61M 25/0127* (2013.01); *A61B 5/283* (2021.01); *A61B 2034/2061* (2016.02); *A61M 2025/0166* (2013.01)

(56) References Cited

U.S. PATENT DOCUMENTS

| | | |
|---|---|---|
| 4,813,429 A | 3/1989 | Eshel et al. |
| 5,099,845 A | 3/1992 | Besz et al. |
| 5,163,935 A | 11/1992 | Black et al. |
| 5,178,153 A | 1/1993 | Einzig |
| 5,207,672 A | 5/1993 | Roth et al. |
| 5,211,165 A | 5/1993 | Dumoulin et al. |
| 5,220,703 A | 6/1993 | Kanayama et al. |
| 5,275,151 A | 1/1994 | Shockey et al. |
| 5,295,212 A | 3/1994 | Morton et al. |
| 5,423,321 A | 6/1995 | Fontenot |
| 5,454,807 A | 10/1995 | Lennox et al. |
| 5,517,997 A | 5/1996 | Fontenot |
| 5,599,492 A | 2/1997 | Engelson |
| 5,622,170 A | 4/1997 | Schulz |
| 5,633,494 A | 5/1997 | Danisch |
| 5,693,043 A | 12/1997 | Kittrell et al. |
| 5,740,808 A | 4/1998 | Panescu et al. |
| 5,827,313 A | 10/1998 | Ream |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 5,957,831 A | 9/1999 | Adair |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,210,362 B1 | 4/2001 | Ponzi |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,619,857 B2 | 9/2003 | Miyake |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 6,975,803 B2 | 12/2005 | Koide et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,699,855 B2 | 4/2010 | Anderson et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,197,494 B2 | 6/2012 | Jaggi et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,119,551 B2 | 9/2015 | Qi et al. |
| 9,186,046 B2 | 11/2015 | Ramamurthy et al. |
| 9,339,206 B2 | 5/2016 | Grunwald |
| 9,345,510 B2 | 5/2016 | Patel et al. |
| 9,360,630 B2 | 6/2016 | Jenner et al. |
| 9,549,685 B2 | 1/2017 | Cox et al. |
| 9,560,954 B2 | 2/2017 | Jacobs et al. |
| 9,572,492 B2 | 2/2017 | Simpson et al. |
| 9,622,706 B2 | 4/2017 | Dick et al. |
| 9,645,326 B1 | 5/2017 | Sausse et al. |
| 9,649,048 B2 | 5/2017 | Cox et al. |
| 9,678,275 B1 | 6/2017 | Griffin |
| 9,678,284 B2 | 6/2017 | Coggi et al. |
| 9,872,978 B1 | 1/2018 | Zaborsky et al. |
| 10,231,643 B2 | 3/2019 | Grunwald |
| 10,231,753 B2 | 3/2019 | Burnside et al. |
| 10,258,240 B1 | 4/2019 | Eberle et al. |
| 10,265,133 B1 | 4/2019 | McClellan |
| 10,327,830 B2 | 6/2019 | Grant et al. |
| 10,349,890 B2 | 7/2019 | Misener et al. |
| 10,448,837 B2 | 10/2019 | Manzke et al. |
| 10,492,876 B2 | 12/2019 | Anastassiou et al. |
| 10,568,586 B2 | 2/2020 | Begin et al. |
| 10,603,126 B2 | 3/2020 | Karguth et al. |
| 10,620,386 B2 | 4/2020 | Van Der Mark et al. |
| 10,631,718 B2 | 4/2020 | Petroff et al. |
| 10,932,670 B2 | 3/2021 | Smith et al. |
| 10,939,889 B2 | 3/2021 | Flexman et al. |
| 10,992,078 B2 | 4/2021 | Thompson et al. |
| 10,992,079 B2 | 4/2021 | Stats et al. |
| 11,000,207 B2 | 5/2021 | Burnside et al. |
| 11,000,265 B1 | 5/2021 | Ryu et al. |
| 11,103,321 B2 | 8/2021 | Braun et al. |
| 11,123,047 B2 | 9/2021 | Jaffer et al. |
| 11,259,892 B2 | 3/2022 | Hufford et al. |
| 11,284,916 B2 | 3/2022 | Patel et al. |
| 11,382,653 B2 | 7/2022 | Patel et al. |
| 11,474,310 B2 | 10/2022 | Sowards et al. |
| 11,525,670 B2 | 12/2022 | Messerly et al. |
| 11,547,282 B2 | 1/2023 | Weise et al. |
| 11,607,150 B2 | 3/2023 | Schweikert et al. |
| 11,621,518 B2 | 4/2023 | Stats et al. |
| 11,707,205 B2 | 7/2023 | Messerly et al. |
| 11,806,096 B2 | 11/2023 | Flatt et al. |
| 11,850,073 B2 | 12/2023 | Wright et al. |
| 11,931,112 B2 | 3/2024 | Thompson et al. |
| 2002/0019627 A1* | 2/2002 | Maguire ............ A61B 18/1492 606/41 |
| 2002/0087206 A1 | 7/2002 | Hirschberg et al. |
| 2002/0166190 A1 | 11/2002 | Miyake et al. |
| 2002/0198457 A1 | 12/2002 | Tearney et al. |
| 2003/0045798 A1 | 3/2003 | Hular et al. |
| 2003/0092995 A1 | 5/2003 | Thompson |
| 2004/0111020 A1 | 6/2004 | Long |
| 2004/0111147 A1 | 6/2004 | Rabkin et al. |

(56) References Cited

U.S. PATENT DOCUMENTS

| | | |
|---|---|---|
| 2004/0242995 A1 | 12/2004 | Maschke |
| 2004/0260182 A1 | 12/2004 | Zuluaga et al. |
| 2005/0033264 A1 | 2/2005 | Redinger |
| 2006/0013523 A1 | 1/2006 | Childlers et al. |
| 2006/0036164 A1 | 2/2006 | Wilson et al. |
| 2006/0100610 A1 | 5/2006 | Wallace et al. |
| 2006/0189959 A1 | 8/2006 | Schneiter |
| 2006/0200049 A1* | 9/2006 | Leo .................. G01L 1/246 600/587 |
| 2006/0241395 A1 | 10/2006 | Kruger et al. |
| 2006/0241492 A1 | 10/2006 | Boese et al. |
| 2007/0060847 A1 | 3/2007 | Leo et al. |
| 2007/0156019 A1 | 7/2007 | Larkin et al. |
| 2007/0179485 A1 | 8/2007 | Yeik et al. |
| 2007/0201793 A1 | 8/2007 | Askins et al. |
| 2007/0253673 A1 | 11/2007 | Nielsen et al. |
| 2007/0287886 A1 | 12/2007 | Saadat |
| 2007/0299425 A1 | 12/2007 | Waner et al. |
| 2008/0034519 A1 | 2/2008 | Fujiwara |
| 2008/0172119 A1 | 7/2008 | Yamasaki et al. |
| 2008/0183128 A1 | 7/2008 | Morriss et al. |
| 2008/0281293 A1* | 11/2008 | Peh .................. A61B 1/00082 604/523 |
| 2008/0285909 A1* | 11/2008 | Younge .................. A61B 1/009 385/13 |
| 2009/0005675 A1 | 1/2009 | Grunwald et al. |
| 2009/0018393 A1 | 1/2009 | Dick et al. |
| 2009/0046980 A1 | 2/2009 | Rohlen |
| 2009/0062634 A1 | 3/2009 | Say et al. |
| 2009/0137952 A1 | 5/2009 | Ramamurthy et al. |
| 2009/0208143 A1 | 8/2009 | Yoon et al. |
| 2009/0227992 A1 | 9/2009 | Nir et al. |
| 2009/0234328 A1 | 9/2009 | Cox et al. |
| 2009/0253967 A1* | 10/2009 | Gill .................. A61B 1/07 600/249 |
| 2009/0304582 A1 | 12/2009 | Rousso et al. |
| 2009/0318757 A1 | 12/2009 | Singh |
| 2009/0324161 A1 | 12/2009 | Prisco |
| 2010/0016729 A1 | 1/2010 | Futrell |
| 2010/0030063 A1 | 2/2010 | Lee et al. |
| 2010/0063534 A1* | 3/2010 | Kugler .................. A61B 17/221 604/528 |
| 2010/0114115 A1 | 5/2010 | Schlesinger et al. |
| 2010/0114190 A1 | 5/2010 | Bendett et al. |
| 2010/0139669 A1 | 6/2010 | Piferi et al. |
| 2010/0204569 A1 | 8/2010 | Burnside et al. |
| 2010/0286531 A1* | 11/2010 | Ryan .................. A61B 5/6852 600/478 |
| 2010/0292758 A1 | 11/2010 | Lee et al. |
| 2011/0087112 A1 | 4/2011 | Leo et al. |
| 2011/0098533 A1 | 4/2011 | Onoda et al. |
| 2011/0144481 A1 | 6/2011 | Feer et al. |
| 2011/0144630 A1 | 6/2011 | Loeb |
| 2011/0166442 A1 | 7/2011 | Sarvazyan |
| 2011/0172680 A1 | 7/2011 | Younge et al. |
| 2011/0178509 A1 | 7/2011 | Zerfas et al. |
| 2011/0196248 A1 | 8/2011 | Grunwald |
| 2011/0245662 A1 | 10/2011 | Eggers et al. |
| 2011/0295108 A1 | 12/2011 | Cox et al. |
| 2012/0046562 A1 | 2/2012 | Powers et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0150732 A1 | 6/2013 | Manzke et al. |
| 2013/0188855 A1 | 7/2013 | Desjardins et al. |
| 2013/0190741 A1 | 7/2013 | Moll et al. |
| 2013/0204124 A1* | 8/2013 | Duindam .................. A61B 17/3468 604/272 |
| 2013/0211246 A1 | 8/2013 | Parasher |
| 2013/0296652 A1 | 11/2013 | Farr |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0031674 A1 | 1/2014 | Newman et al. |
| 2014/0046261 A1 | 2/2014 | Newman et al. |
| 2014/0058368 A1 | 2/2014 | Hogue |
| 2014/0088413 A1 | 3/2014 | Von Bucsh et al. |
| 2014/0121468 A1 | 5/2014 | Eichenholz |
| 2014/0155948 A1 | 6/2014 | Walsh et al. |
| 2014/0188133 A1 | 7/2014 | Misener |
| 2014/0221829 A1 | 8/2014 | Maitland et al. |
| 2014/0259477 A1 | 9/2014 | Huang |
| 2014/0275997 A1 | 9/2014 | Chopra et al. |
| 2014/0318825 A1 | 10/2014 | Erb et al. |
| 2014/0378945 A1 | 12/2014 | Beri |
| 2015/0029511 A1 | 1/2015 | 'T Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0105654 A1 | 4/2015 | Meyer |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0244465 A1 | 8/2015 | Chou et al. |
| 2015/0270900 A1 | 9/2015 | Hilario et al. |
| 2015/0301288 A1 | 10/2015 | Thornton, Jr. |
| 2015/0305816 A1 | 10/2015 | Hadzic |
| 2015/0320977 A1 | 11/2015 | Vitullo et al. |
| 2016/0018602 A1 | 1/2016 | Govari et al. |
| 2016/0151115 A1 | 6/2016 | Karguth et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2016/0374589 A1 | 12/2016 | Misener et al. |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1 | 3/2017 | Silverstein et al. |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0303824 A1 | 10/2017 | Schlesinger et al. |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2018/0369432 A1 | 12/2018 | Zaborsky |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |

(56) References Cited

U.S. PATENT DOCUMENTS

| | | |
|---|---|---|
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1 | 12/2019 | Courtney et al. |
| 2020/0046434 A1 | 2/2020 | Graetzel et al. |
| 2020/0155073 A1 | 5/2020 | Hwang et al. |
| 2020/0170724 A1 | 6/2020 | Flatt et al. |
| 2020/0188036 A1* | 6/2020 | Ding ............... A61B 17/7074 |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1 | 2/2021 | Thompson et al. |
| 2021/0298680 A1 | 3/2021 | Sowards et al. |
| 2021/0154440 A1 | 5/2021 | Misener |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1* | 9/2021 | Tegg .................... A61B 5/062 |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2023/0082991 A1 | 3/2023 | Sowards et al. |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1 | 11/2023 | Moore |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 3545849 A1 | 10/2019 |
| EP | 3725252 A1 | 10/2020 |
| WO | 99/64099 A1 | 12/1999 |
| WO | 1999064099 A1 | 12/1999 |
| WO | 2006080076 A1 | 8/2006 |
| WO | 2006122001 A2 | 11/2006 |
| WO | 2009/155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016/061431 A1 | 4/2016 |
| WO | 2016193051 A1 | 12/2016 |
| WO | 2018071490 A1 | 4/2018 |
| WO | 2018/096491 A1 | 5/2018 |
| WO | 2019037071 A1 | 2/2019 |
| WO | 2019/046769 A1 | 3/2019 |
| WO | 2019230713 A1 | 12/2019 |
| WO | 2020/142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022/031613 A1 | 2/2022 |
| WO | 2022/081586 A1 | 4/2022 |
| WO | 2022/081723 A1 | 4/2022 |
| WO | 2022109045 A1 | 5/2022 |
| WO | 2022115624 A1 | 6/2022 |
| WO | 2022221608 A1 | 10/2022 |
| WO | 2023043947 A1 | 3/2023 |
| WO | 2023/172652 A1 | 9/2023 |
| WO | 2023/177822 A1 | 9/2023 |
| WO | 2023/177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

PCT/US2021/054802 filed Oct. 13, 2021 International Search Report and Written Opinion dated Feb. 2, 2022.
PCT/US2021/060849 filed Nov. 24, 2021 International Search Report and Written Opinion dated Mar. 9, 2022.
U.S. Appl. No. 17/185,777, filed Feb. 25, 2021 Non-Final Office Action dated Feb. 9, 2022.
PCT/US2023/014849 filed Mar. 8, 2023 International Search Report and Written Opinion dated Jun. 7, 2023.
PCT/US2023/015416 filed Mar. 16, 2023 International Search Report and Written Opinion dated May 26, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020044 filed Apr. 26, 2023 International Search Report and Written Opinion dated Jul. 19, 2023.
U.S. Appl. No. 17/217,852, filed Mar. 30, 2021 Non Final Office Action dated Jun. 7, 2023.
U.S. Appl. No. 17/499,644, filed Oct. 12, 2021 Restriction Requirement dated Jul. 11, 2023.
U.S. Appl. No. 17/697,895, filed Mar. 17, 2022 Final Office Action dated Aug. 16, 2023.
U.S. Appl. No. 17/697,895, filed Mar. 17, 2022 Non Final Office Action dated Jun. 14, 2023.
PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
PCT/US2018/026493 filed Apr. 6, 2018 International Search Report and Written Opinion dated Jun. 22, 2018.
PCT/US2020/044801 filed Aug. 3, 2020 International Search Report and Written Opinion dated Oct. 26, 2020.
PCT/US2020/062396 filed Nov. 25, 2020 International Search Report and Written Opinion dated Mar. 2, 2021.
PCT/US2020/062407 filed Nov. 25, 2020 International Search Report and Written Opinion dated Mar. 11, 2021.
PCT/US2021/019713 filed Feb. 25, 2021 International Search Report and Written Opinion dated Jul. 6, 2021.

(56) References Cited

OTHER PUBLICATIONS

PCT/US2021/020079 filed Feb. 26, 2021 International Search Report and Written Opinion dated Jun. 4, 2021.
PCT/US2021/020732 filed Mar. 3, 2021 International Search Report and Written Opinion dated Jul. 5, 2021.
PCT/US2021/038899 filed Jun. 24, 2021 International Search Report and Written Opinion dated Oct. 6, 2021.
PCT/US2021/038954 filed Jun. 24, 2021 International Search Report and Written Opinion dated Oct. 28, 2021.
PCT/US2021/041128 filed Jul. 9, 2021 International Search Report and Written Opinion dated Oct. 25, 2021.
U.S. Appl. No. 15/947,267, filed Apr. 6, 2018 Final Office Action dated Jun. 30, 2021.
U.S. Appl. No. 15/947,267, filed Apr. 6, 2018 Final Office Action dated Nov. 10, 2020.
U.S. Appl. No. 15/947,267, filed Apr. 6, 2018 Non-Final Office Action dated Mar. 12, 2021.
U.S. Appl. No. 15/947,267, filed Apr. 6, 2018 Non-Final Office Action dated May 29, 2020.
U.S. Appl. No. 15/947,267, filed Apr. 6, 2018 Non-Final Office Action dated Oct. 13, 2021.
PCT/US2022/043698 filed Sep. 15, 2022 International Search Report and Written Opinion dated Dec. 19, 2022.
U.S. Appl. No. 17/967,794, filed Oct. 17, 2022 Notice of Allowance dated Feb. 15, 2023.
U.S. Appl. No. 17/217,852, filed Mar. 30, 2021 Restriction Requirement dated Mar. 21, 2023.
U.S. Appl. No. 17/187,536, filed Feb. 26, 2021 Non-Final Office Action dated May 17, 2023.
PCT/US2022/024934 filed Apr. 14, 2022 International Search Report and Written Opinion dated Jul. 18, 2022.
PCT/US2023/020042 filed Apr. 26, 2023 International Search Report and Written Opinion dated Sep. 26, 2023.
PCT/US2023/025757 filed Jun. 20, 2023 International Search Report and Written Opinion dated Sep. 11, 2023.
PCT/US2023/027527 filed Jul. 12, 2023 International Search Report and Written Opinion dated Oct. 16, 2023.
U.S. Appl. No. 17/187,536, filed Feb. 26, 2021 Advisory Action dated Nov. 21, 2023.
U.S. Appl. No. 17/187,536, filed Feb. 26, 2021 Final Office Action dated Sep. 20, 2023.
U.S. Appl. No. 17/187,536, filed Feb. 26, 2021 Non-Final Office Action dated Dec. 15, 2023.
U.S. Appl. No. 17/217,852, filed Mar. 30, 2021 Ex Parte Quayle Action dated Sep. 8, 2023.
U.S. Appl. No. 17/217,852, filed Mar. 30, 2021 Notice of Allowance dated Nov. 7, 2023.
U.S. Appl. No. 17/499,644, filed Oct. 12, 2021 Notice of Allowance dated Sep. 18, 2023.
U.S. Appl. No. 17/697,895, filed Mar. 17, 2022 Advisory Action dated Sep. 8, 2023.
U.S. Appl. No. 17/697,895, filed Mar. 17, 2022 Non-Final Office Action dated Jan. 11, 2024.
PCT/US2021/059755 filed Nov. 17, 2021 International Search Report and Written Opinion dated Apr. 29, 2022.
U.S. Appl. No. 17/185,777, filed Feb. 25, 2021 Notice of Allowance dated Jun. 10, 2022.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/689,773, filed Mar. 8, 2022 Non-Final Office Action dated Mar. 19, 2024.
U.S. Appl. No. 17/697,895, filed Mar. 17, 2022 Notice of Allowance dated May 8, 2024.
U.S. Appl. No. 17/731,155, filed Apr. 27, 2022 Restriction Requirement dated Feb. 28, 2024.
U.S. Appl. No. 17/849,447, filed Jun. 24, 2022 Non-Final Office Action dated Apr. 10, 2024.
U.S. Appl. No. 17/187,536, filed Feb. 26, 2021 Final Office Action dated Jul. 2, 2024.
U.S. Appl. No. 17/689,773, filed Mar. 8, 2022 Final Office Action dated Aug. 1, 2024.
U.S. Appl. No. 17/696,675, filed Mar. 16, 2022 Non-Final Office Action dated Jun. 11, 2024.
U.S. Appl. No. 17/725,394, filed Apr. 20, 2022 Non-Final Office Action dated Jun. 17, 2024.
U.S. Appl. No. 17/849,447, filed Jun. 24, 2022 Final Office Action dated Aug. 8, 2024.
U.S. Appl. No. 18/524,620, filed Nov. 30, 2023 Non-Final Office Action dated Jun. 18, 2024.
PCT/US2023/015536 filed Mar. 17, 2023 International Preliminary Report on Patentability dated Sep. 10, 2024.
PCT/US2023/018076 filed Apr. 10, 2023 International Preliminary Report on Patentability dated Oct. 8, 2024.
PCT/US2023/019130 filed Apr. 19, 2023 International Preliminary Report on Patentability dated Oct. 8, 2023.
U.S. Appl. No. 17/187,536, filed Feb. 26, 2021 Advisory Action dated Oct. 9, 2024.
U.S. Appl. No. 17/187,536, filed Feb. 26, 2021 Notice of Allowance dated Oct. 29, 2024.
U.S. Appl. No. 17/191,551, filed Mar. 3, 2021 Non-Final Office Action dated Aug. 16, 2024.
U.S. Appl. No. 17/529,022, filed Nov. 17, 2021 Non-Final Office Action dated Sep. 30, 2024.
U.S. Appl. No. 17/689,773, filed Mar. 8, 2022 Advisory Action dated Nov. 1, 2024.
U.S. Appl. No. 17/731,155 filed Apr. 27, 2022 Non-Final Office Action dated Aug. 22, 2024.
U.S. Appl. No. 17/849,447, filed Jun. 24, 2022 Advisory Action dated Oct. 24, 2024.
U.S. Appl. No. 18/141,289, filed Apr. 28, 2023 Non-Final Office Action dated Sep. 28, 2024.
U.S. Appl. No. 18/524,620, filed Nov. 30, 2023 Notice of Allowance dated Sep. 12, 2024.

* cited by examiner

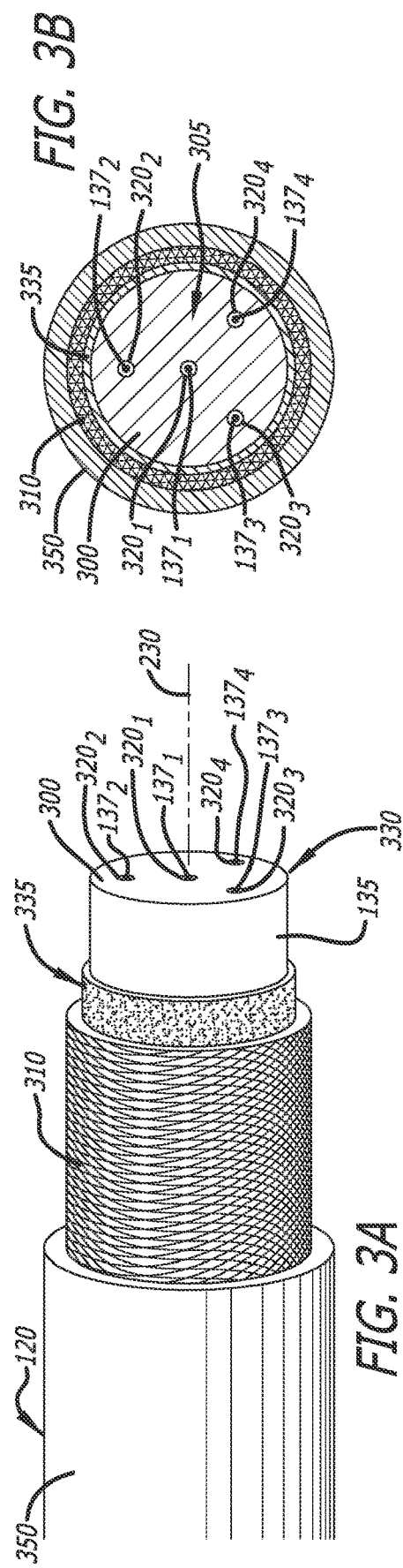
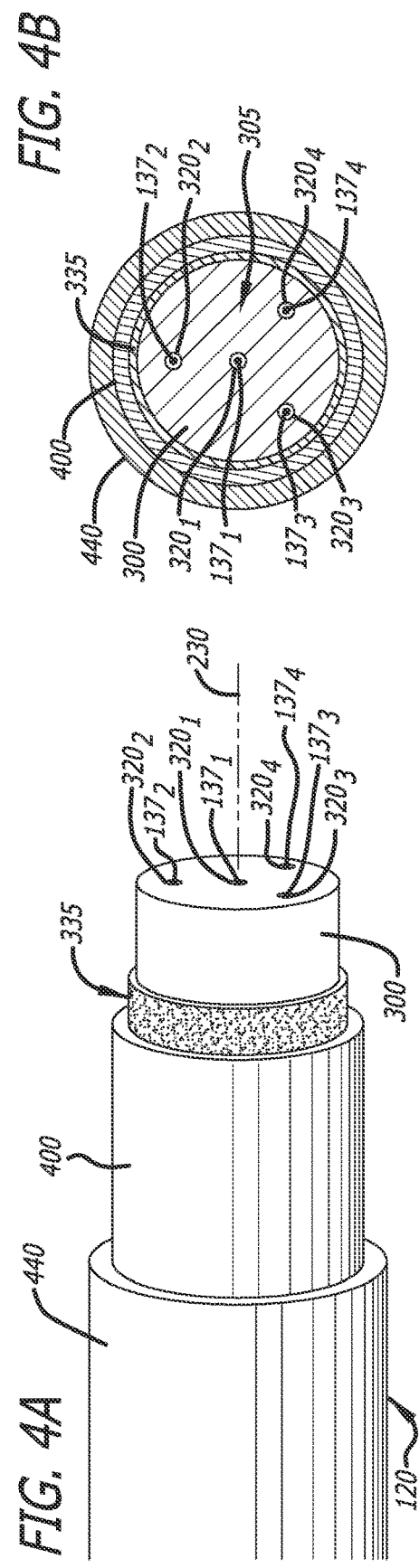

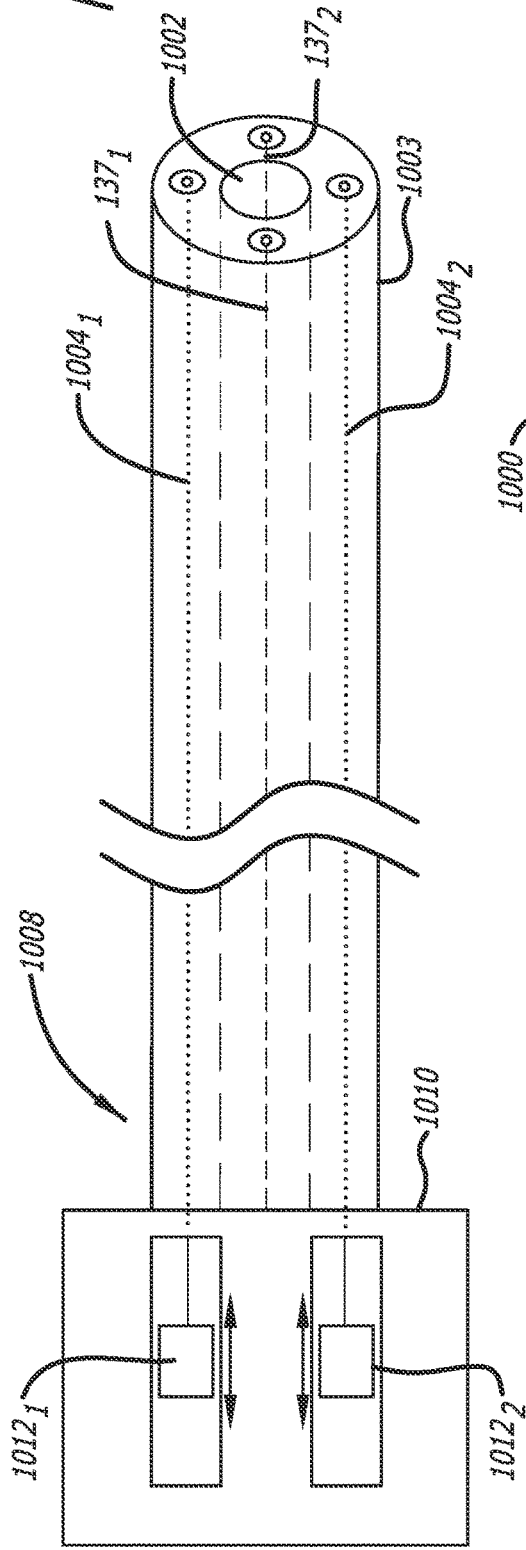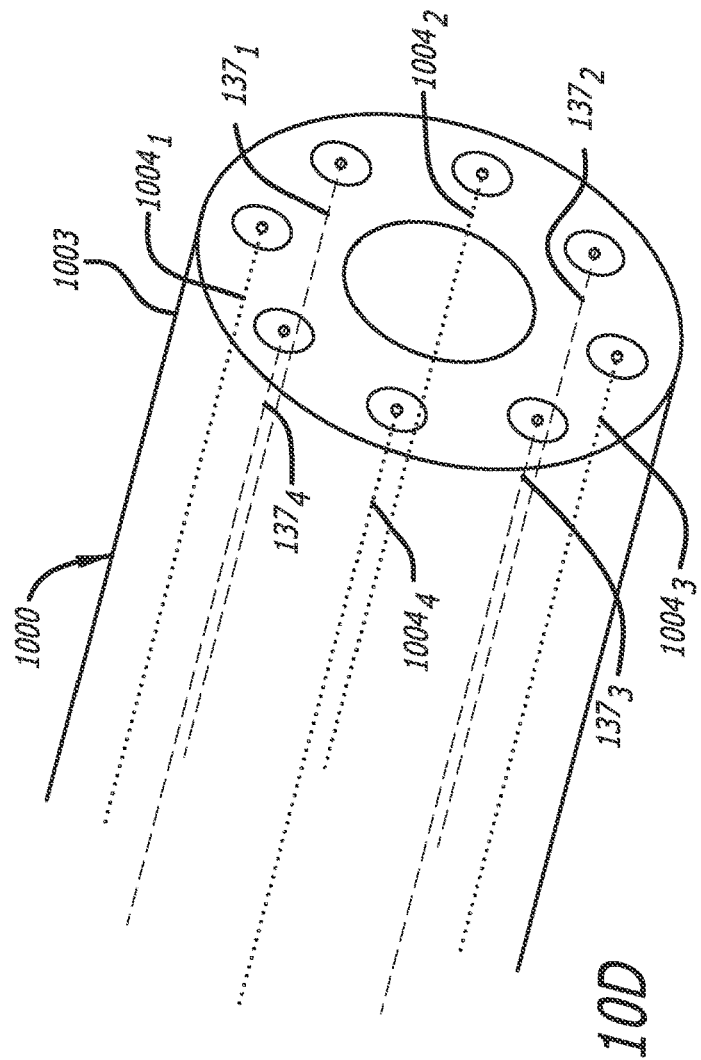
FIG. 10C
FIG. 10D

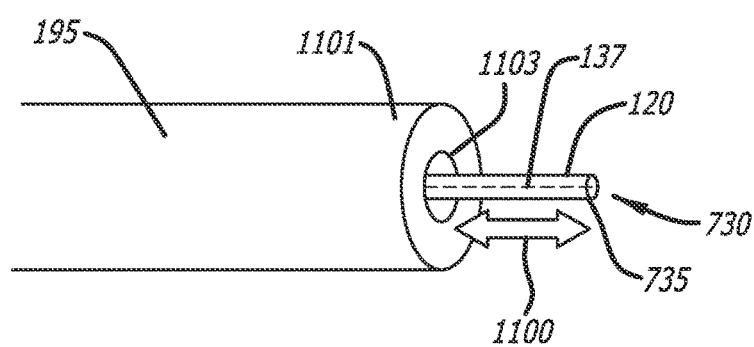
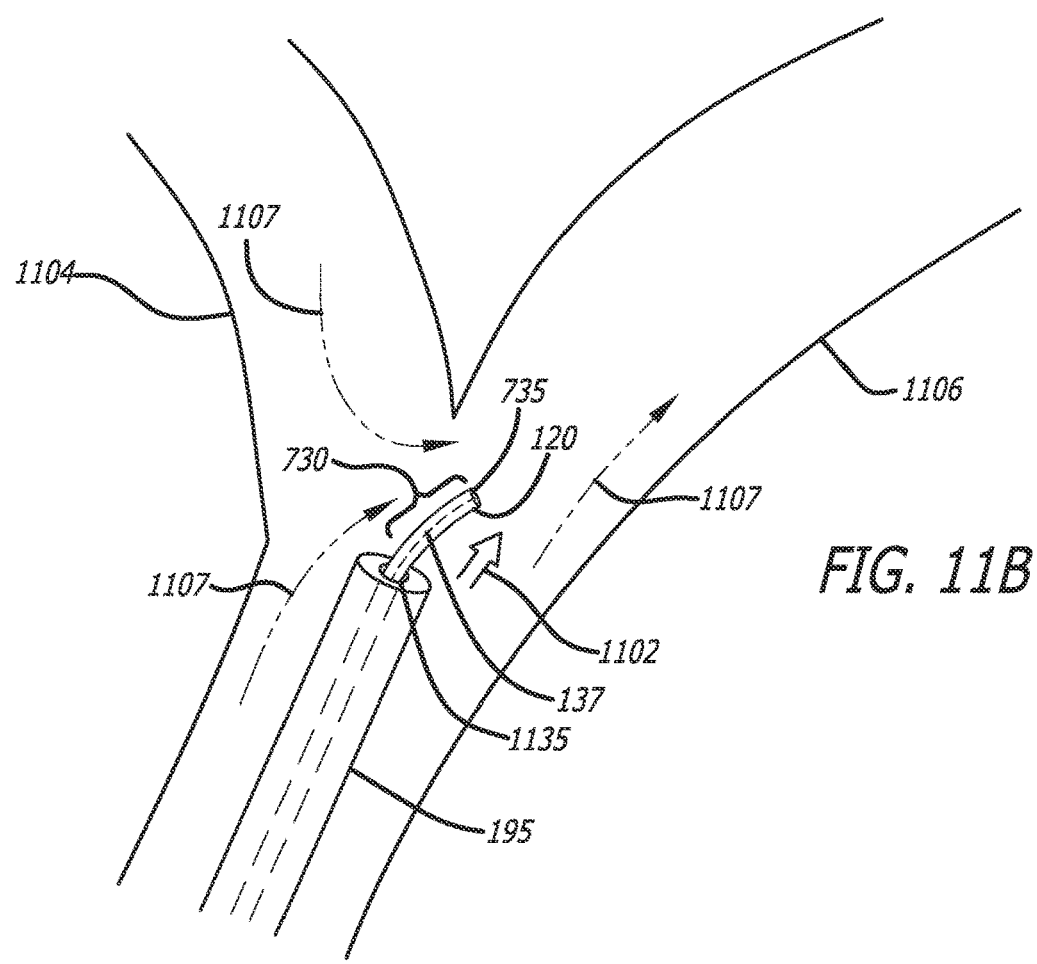
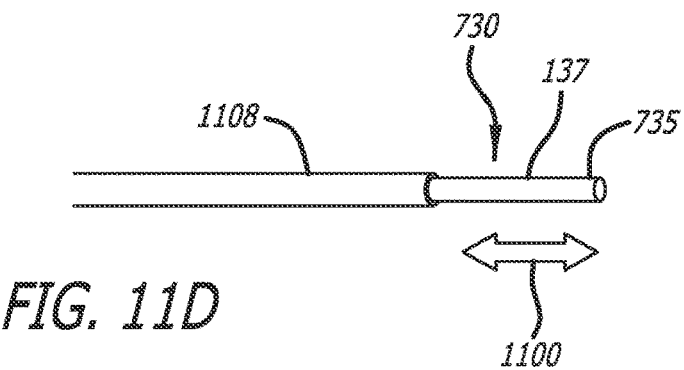

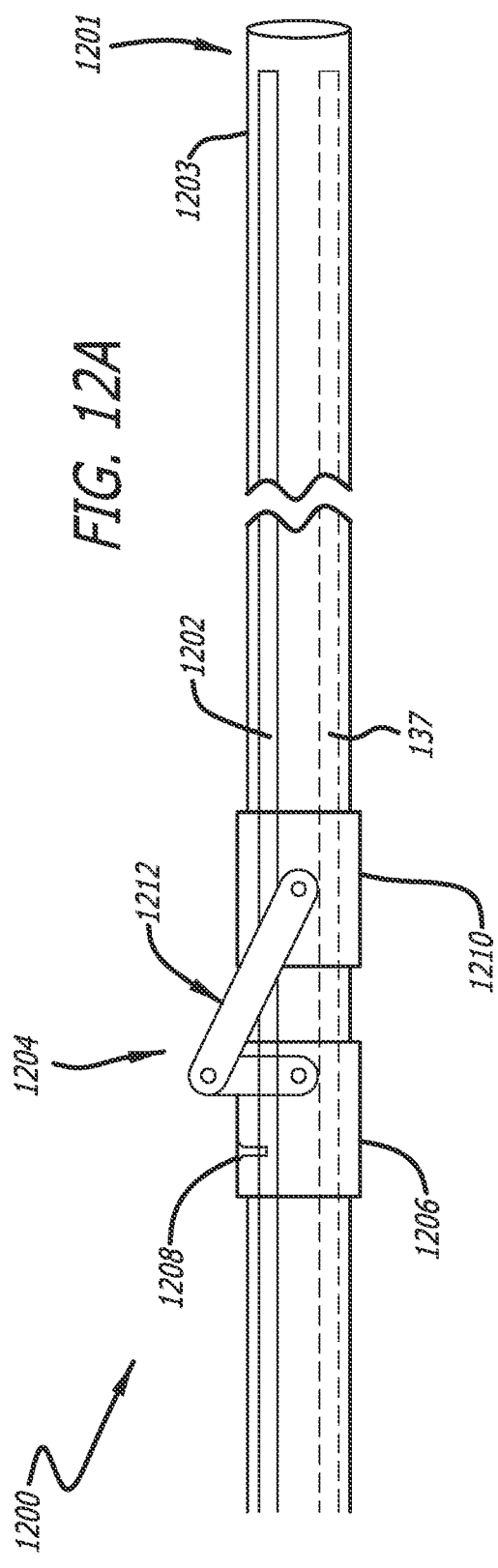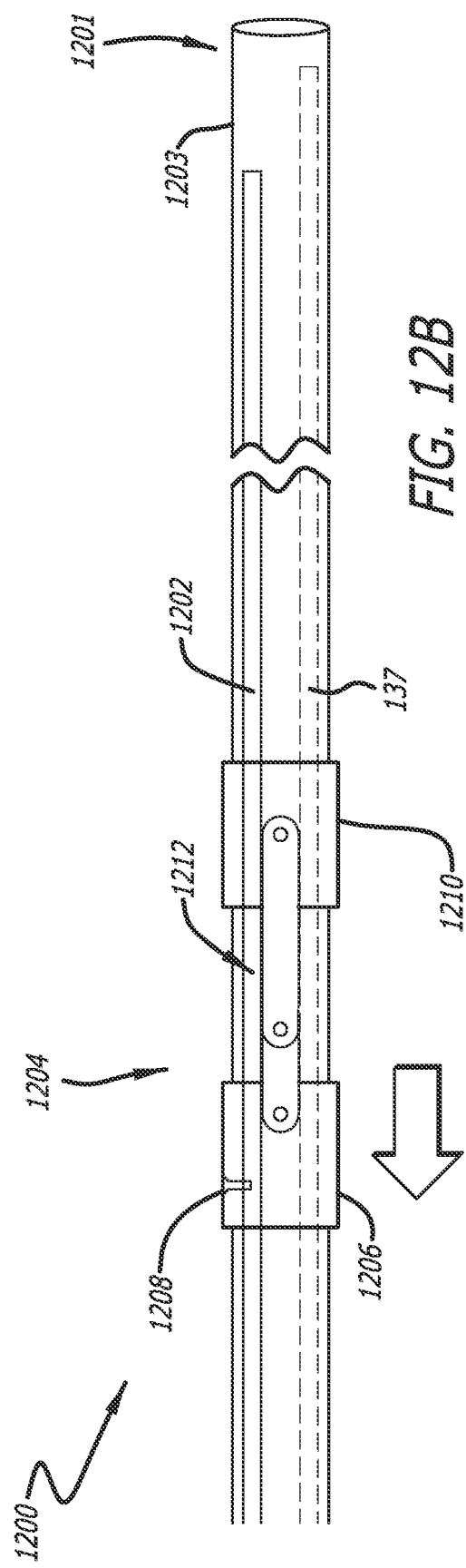

STEERABLE FIBER OPTIC SHAPE SENSING ENABLED ELONGATED MEDICAL INSTRUMENT

PRIORITY

This application claims the benefit of priority to U.S. Provisional Application No. 63/117,901, filed Nov. 24, 2020, and to U.S. Provisional Application No. 63/119,858, filed Dec. 1, 2020, each of which is incorporated by reference in its entirety into this application.

BACKGROUND

In the past, certain intravascular guidance of medical instruments, such as guidewires and catheters for example, have used fluoroscopic methods for tracking tips of the medical instruments and determining whether distal tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

More recently, electromagnetic tracking systems have been used involving stylets. Generally, electromagnetic tracking systems feature three components: a field generator, a sensor unit and control unit. The field generator uses several coils to generate a position-varying magnetic field, which is used to establish a coordinate space. Attached to the stylet, such as near a distal end (tip) of the stylet for example, the sensor unit includes small coils in which current is induced via the magnetic field. Based on the electrical properties of each coil, the position and orientation of the medical instrument may be determined within the coordinate space. The control unit controls the field generator and captures data from the sensor unit.

Although electromagnetic tracking systems avoid line-of-sight reliance in tracking the tip of a stylet while obviating radiation exposure and potentially harmful contrast media associated with fluoroscopic methods, electromagnetic tracking systems are prone to interference. More specifically, since electromagnetic tracking systems depend on the measurement of magnetic fields produced by the field generator, these systems are subject to electromagnetic field interference, which may be caused by the presence of many different types of consumer electronics such as cellular telephones. Additionally, electromagnetic tracking systems are subject to signal drop out, depend on an external sensor, and are defined to a limited depth range.

Disclosed herein is a system including a steerable medical instrument having disposed therein an optical fiber and methods performed thereby where the system is configured to provide confirmation of tip placement or tracking information using optical fiber technology. The medical instrument may be steerable via one of a plurality of steering mechanisms or methods, examples of which include, but are not limited or restricted to, (i) an elongated medical instrument having a predetermined shape (e.g., at a distal tip) where the elongated medical instrument may be rotatable facilitating steering, (ii) a shape or direction steering mechanism such as an external electro-magnet driven assembly or a micro-wire guided or driven assembly, and/or (iii) a variable stiffness assembly that enables adjustment of a stiffening member or sheath, adjustment of a catheter or tube relative to a fiber-enabled disposable (or vice versa), or includes a "a loose core" assembly. Further, some embodiments combine the fiber optic shape sensing functionality with one or more of intravascular electrocardiogram (ECG) monitoring, impedance/conductance sensing and blood flow directional detection.

Current shape sensing methods for the intravascular guidance of medical devices utilize integrated optical-fiber stylets having fiber Bragg grating ("FBG") sensors along their length for shape-sensing with the integrated optical-fiber stylets. Being integrated, the integrated optical-fiber stylets are limited to the medical devices into which they are integrated. Because such medical devices are single-use medical devices, the integrated optical-fiber stylets, too, are limited in their use. What is needed is a separate optical-fiber insert that can be used one or more times in any number of different medical devices, particularly those involved in a single medical procedure.

SUMMARY

Briefly summarized, embodiments disclosed herein are directed to systems, apparatus and methods for confirming tip placement or tracking information using a steerable, elongated medical instrument that is enabled with optical fiber technology. In some embodiments, the medical instrument includes one or more optical fiber cores, where each are configured with an array of sensors (reflective gratings), which are spatially distributed over a prescribed length of the core fiber to generally sense external strain and temperature on those regions of the core fiber occupied by the sensor. Each optical fiber core is configured to receive broadband light from a console during advancement through the vasculature of a patient, where the broadband light propagates along at least a partial distance of the optical fiber core toward the distal end. Given that each sensor positioned along the optical fiber core is configured to reflect light of a different, specific spectral width, the array of sensors enables distributed measurements throughout the prescribed length of the medical instrument. These distributed measurements may include wavelength shifts having a correlation with strain and/or temperature experienced by the sensor.

The reflected light from the sensors (reflective gratings) within an optical fiber core is returned from the medical instrument for processing by the console. The physical state of the medical instrument may be ascertained based on analytics of the wavelength shifts of the reflected light. For example, the strain caused through bending of the medical instrument and hence angular modification of the optical fiber core, causes different degrees of deformation. The different degrees of deformation alter the shape of the sensors (reflective grating) positioned on the optical fiber core, which may cause variations (shifts) in the wavelength of the reflected light from the sensors positioned on the optical fiber core. The optical fiber core may comprise a single optical fiber, or a plurality of optical fibers (in which case, the optical fiber core is referred to as a "multi-core optical fiber").

As used herein, the term "core fiber," generally refers to a single optical fiber core disposed within a medical instrument. Thus, discussion of a core fiber refers to single optical fiber core and discussion of a multi-core optical fiber refers to a plurality of core fibers. Various embodiments discussed below to detection of the health (and particularly the damage) that occurs in each of an optical fiber core of medical instrument including (i) a single core fiber, and (ii) a plurality of core fibers. It is noted that in addition to strain altering the shape of a sensor, ambient temperature variations may also alter the shape of a sensor, thereby causing variations (shifts) in the wavelength of the reflected light from the sensors positioned on the optical fiber core.

With respect to the steerability of the elongated medical instrument, steering of the elongated medical instrument may be accomplished in one or more of a plurality of steering mechanisms or methods. Enabling a clinician to steer an elongated medical instrument during advancement in a patient vasculature provides numerous advantages regardless of the steering mechanism or method. For example, steering an elongated medical instrument during such advancement decreases the likelihood that the elongated medical instrument deviates from a desired or intended path. Providing a fiber optic-enabled elongated medical instrument that is also steerable enables a clinician to steer the elongated medical instrument in accordance with the precise tip placement or tracking information obtained through the fiber optic shape sensing functionality. As briefly referenced above, there are multiple embodiments provided for in the disclosure with one embodiment including an elongated medical instrument that includes one or more fiber optical cores integrated therein with the elongated medical instrument having a predetermined shape, such as a curved at a distal portion. In such an embodiment, the elongated medical instrument may be rotated by the clinician in order to steer the advancement of the elongated medical instrument based on the curved distal portion.

A second set of embodiments disclosed herein may include a fiber optic-enabled elongated medical instrument having a shape or direction steering mechanism. For example, the shape or direction steering mechanism may include an external electro-magnet driven assembly, which may include a magnetic portion of the distal tip and an external electro-magnet. The external electro-magnet may be utilized to bias the distal tip in a particular direction thereby enabling the steering during advancement. Another alternative embodiment includes a micro-wire guided or driven assembly.

A second set of embodiments disclosed herein may include a variable stiffness assembly that enables adjustment of the positioning of one portion of the medical instrument relative to another (e.g., a "loose core assembly"), adjustment of the positioning of a stiffening member or sheath surrounding the medical instrument.

For example, the variable stiffness assembly may include a loose core assembly that includes a center portion of the medical instrument configured to be advanced or retracted relative to the remainder of the medical instrument (e.g., the portion of the medical instrument surrounding the adjustable center component). As will be discussed below, advancement of a center portion that has a reduced stiffness compared to the outer surrounding portion provides for a "floppy" tip, which is prone to follow a direction of blood flow or be biased by gravity. Thus, a clinician may steer advancement based on knowledge of blood flow and/or gravity.

Alternatively, the variable stiffness assembly may include a stiffening member or sheath surrounding the medical instrument, where the stiffening member or sheath has a greater stiffness than the medical instrument. Thus, advancing or retracting the stiffening member or sheath relative to the medical results in either a stiff or rigid distal tip or a floppy tip discussed above. In some embodiments, the medical instrument may be a disposable, fiber optic-enabled guidewire or stylet and the stiffening member may be a catheter where the disposable guidewire or stylet is inserted into the catheter. The catheter and/or the stylet disposable, fiber optic-enabled guidewire or stylet may be retracted or advanced relative to the other resulting in either a stiff or rigid distal tip or a floppy tip discussed above.

In particular, the reflected light is received by an optical receiver of the console, which is configured to translate the reflected light signals into reflection data, namely data in the form of electrical signals representative of the reflected light signals. The logic of the console is configured to determine a correlation between the reflection data and blood oxygen levels, where the logic may then correlation a blood oxygen level to a particular location of the distal tip of the optical fiber within the vasculature. In some embodiments, the site at which the optical fiber entered the vasculature may be utilized in determining the location within the vasculature. For instance, when two locations each closely correlate to the determined oxygen level, the logic of the console may select a particular location based on proximity to the entry site, and optionally knowledge of advancement of the distal tip of the optical fiber within the vasculature. For example, the logic of the console may select a location option based on oxygen levels based on proximity to the entry site, e.g., a location option within the shoulder may be selected over a location option in the leg when the entry site of the optical fiber is the cephalic vein of a patient's forearm. Other embodiments utilizing the reflection data are discussed below that may also assist a clinician in navigating advancement of the optical fiber (and corresponding medical instrument).

Specific embodiments of the disclosure include utilization of a medical instrument, such as a stylet, featuring a multi-core optical fiber and a conductive medium that collectively operate for tracking placement with a body of a patient of the stylet or another medical instrument (such as a catheter) in which the stylet is disposed. In lieu of a stylet, a guidewire may be utilized. For convenience, embodiments are generally discussed where the optical fiber core is disposed within a stylet; however, the disclosure is not intended to be so limited as the functionality involving detection of the health of an optical fiber core disclosed herein may be implemented regardless of the medical instrument in which the optical fiber core is disposed. In some embodiments, the optical fiber core may be integrated directly into a wall of the catheter.

In some embodiments, the optical fiber core of a stylet is configured to return information for use in identifying its physical state (e.g., shape length, shape, and/or form) of (i) a portion of the stylet (e.g., tip, segment of stylet, etc.) or a portion of a catheter inclusive of at least a portion of the stylet (e.g., tip, segment of catheter, etc.) or (ii) the entirety or a substantial portion of the stylet or catheter within the body of a patient (hereinafter, described as the "physical state of the stylet" or the "physical state of the catheter"). According to one embodiment of the disclosure, the returned information may be obtained from reflected light signals of different spectral widths, where each reflected light signal corresponds to a portion of broadband incident light propagating along a core of the multi-core optical fiber (core fiber) that is reflected back over the core fiber by a particular sensor located on the core fiber. One illustrative example of the returned information may pertain to a change in signal characteristics of the reflected light signal returned from the sensor, where wavelength shift is correlated to (mechanical) strain on the core fiber or a detected change in ambient temperature.

In some embodiments, the core fiber utilizes a plurality of sensors and each sensor is configured to reflect a different spectral range of the incident light (e.g., different light frequency range). Based on the type and degree of strain asserted on each core fiber, the sensors associated with that core fiber may alter (shift) the wavelength of the reflected light to convey the type and degree of stain on that core fiber at those locations of the stylet occupied by the sensors. The sensors are spatially distributed at various locations of the core fiber between a proximal end and a distal end of the stylet so that shape sensing of the stylet may be conducted based on analytics of the wavelength shifts. Herein, the shape sensing functionality is paired with the ability to simultaneously pass an electrical signal through the same member (stylet) through conductive medium included as part of the stylet.

Similarly, the sensors may alter (shift) the wavelength of the reflected light to convey sensed variations in ambient temperature. The alterations in response to detected variations in ambient temperature thereby provide for a temperature sensing functionality.

More specifically, in some embodiments each core fiber of the multi-core optical fiber is configured with an array of sensors, which are spatially distributed over a prescribed length of the core fiber to generally sense external strain on or variations in ambient temperature proximate those regions of the core fiber occupied by the sensor. Given that each sensor positioned along the same core fiber is configured to reflect light of a different, specific spectral width, the array of sensors enables distributed measurements throughout the prescribed length of the multi-core optical fiber. These distributed measurements may include wavelength shifts having a correlation with strain experienced and/or temperature variations detected by the sensor.

In more detail, each sensor may operate as a reflective grating such as a fiber Bragg grating (FBG), namely an intrinsic sensor corresponding to a permanent, periodic refractive index change inscribed into the core fiber. Stated differently, the sensor operates as a light reflective mirror for a specific spectral width (e.g., a specific wavelength or specific range of wavelengths). As a result, as broadband incident light is supplied by an optical light source and propagates through a particular core fiber, upon reaching a first sensor of the distributed array of sensors for that core fiber, light of a prescribed spectral width associated with the first sensor is reflected back to an optical receiver within a console, including a display and the optical light source. The remaining spectrum of the incident light continues propagation through the core fiber toward a distal end of the stylet. The remaining spectrum of the incident light may encounter other sensors from the distributed array of sensors, where each of these sensors is fabricated to reflect light with different specific spectral widths to provide distributed measurements, as described above.

During operation, multiple light reflections (also referred to as "reflected light signals") are returned to the console from each of the plurality of core fibers of the multi-core optical fiber. Each reflected light signal may be uniquely associated with a different spectral width. Information associated with the reflected light signals may be used to determine a three-dimensional representation of the physical state of the stylet within the body of a patient through detection of strain in response to emitted incident light. Herein, the core fibers are spatially separated with the cladding of the multi-mode optical fiber and each core fiber is configured to separately return light of different spectral widths (e.g., specific light wavelength or a range of light wavelengths) reflected from the distributed array of sensors fabricated in each of the core fibers.

During vasculature insertion and advancement of the catheter, the clinician may rely on the console to visualize a current physical state (e.g., shape) of a catheter guided by the stylet to avoid potential path deviations. As the periphery core fibers reside at spatially different locations within the cladding of the multi-mode optical fiber, changes in angular orientation (such as bending with respect to the center core fiber, etc.) of the stylet imposes different types (e.g., compression or tension) and degrees of strain on each of the periphery core fibers as well as the center core fiber. The different types and/or degree of strain may cause the sensors of the core fibers to apply different wavelength shifts, which can be measured to extrapolate the physical state of the stylet (catheter).

Embodiments of the disclosure may include a combination of one or more of the methodologies to confirm that an optical fiber within a body of implementation (e.g., an introducer wire, a guidewire, a stylet within a needle, a needle with fiber optic inlayed into the cannula, a stylet configured for use with a catheter, an optical fiber between a needle and a catheter, and/or an optical fiber integrated into a catheter) is located at a specified location with the vasculature based on oximetry readings determined from light reflected from one or more sensors disposed at the distal tip of the optical fiber.

Certain embodiments of the disclosure pertain to the utilization of fiber optic shape sensing, detection of oxygen levels and/or blood flow direction to track advancement of a medical instrument throughout the vasculature of a patient. For example, as noted above, each core fiber includes a plurality of reflective gratings disposed along its length, wherein each reflective grating receives broadband incident light and reflects light signals having a specific spectral width (e.g., a specific wavelength or specific range of wavelengths) that may be shifted based on an amount of strain applied to a length of the core fiber corresponding to the reflective grating. The incident light also be emitted from the distal tip of a core fiber into the vasculature such that the distal tip receives light reflected from the red blood cells, which propagates back to the console.

Some embodiments disclose a medical instrument system for inserting a medical instrument within a patient body, the system comprising the medical instrument comprising an optical fiber having one or more of core fibers, wherein a distal portion of the medical instrument is shaped with a predetermined curvature, and a console including one or more processors and a non-transitory computer-readable medium having stored thereon logic, when executed by the one or more processors, causes operations including providing an incident light signal to the optical fiber, receiving reflected light signals of different spectral widths of the incident light by the optical fiber, processing the reflected light signals associated with the optical fiber, and determining a location of a distal tip of the medical instrument within the patient body, and wherein the medical instrument is configured to be rotated around a longitudinal axis in order to direct the distal tip in a particular direction.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber.

In some embodiments, the optical fiber is a single-core optical fiber, and wherein the incident light is provided in pulses. In some embodiments, the optical fiber is a multi-core optical fiber including a plurality of core fibers. In some embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

Other embodiments disclose a method for placing a medical instrument into a body of a patient, the method comprising providing an incident light signal to an optical fiber disposed within the medical instrument, the optical fiber having one or more core fibers, wherein a distal portion of the medical instrument is shaped with a predetermined curvature, receiving reflected light signals of different spectral widths of the incident light by the optical fiber, processing the reflected light signals associated with the optical fiber and determining a location of a distal tip of the medical instrument within the patient body, wherein the medical instrument is configured to be rotated around a longitudinal axis in order to direct the distal tip in a particular direction.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In some embodiments, the optical fiber is a single-core optical fiber, and wherein the incident light is provided in pulses. In some embodiments, the optical fiber is a multi-core optical fiber including a plurality of core fibers.

In some embodiments, the method further comprises generating a display indicating the location of the distal tip of the optical fiber within the patient body. In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

Other embodiments disclose a medical instrument system for inserting a medical instrument within a patient body, the system comprising the medical instrument comprising an optical fiber having one or more of core fibers, wherein the medical instrument includes a distal tip that is magnetic, magnetized, metallic or ferrous, an external magnetic device configured for placement on the patient body, wherein a magnetic field of the external magnetic device attracts or repels the distal tip to steer the medical instrument within the patient body and a console including one or more processors and a non-transitory computer-readable medium having stored thereon logic, when executed by the one or more processors, causes operations including providing an incident light signal to the optical fiber, receiving reflected light signals of different spectral widths of the incident light by the optical fiber, processing the reflected light signals associated with the optical fiber, and determining a location of a distal tip of the medical instrument within the patient body.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In some embodiments, the optical fiber is a single-core optical fiber, and wherein the incident light is provided in pulses. In some embodiments, the optical fiber is a multi-core optical fiber including a plurality of core fibers. In some embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter. In some embodiments, the external magnetic device is an electromagnetic device.

Some embodiments disclose a method for placing a medical instrument into a body of a patient, the method comprising providing an incident light signal to an optical fiber disposed within the medical instrument, the optical fiber having one or more core fibers, wherein the medical instrument includes a distal tip that is magnetic, magnetized, metallic or ferrous, receiving reflected light signals of different spectral widths of the incident light by the optical fiber, processing the reflected light signals associated with the optical fiber and determining a location of a distal tip of the medical instrument within the patient body, wherein the medical instrument is configured to be steered by an attraction or repulsion of the distal tip to a magnetic field of an external magnetic device placed on the patient body.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In some embodiments, the optical fiber is a single-core optical fiber, and wherein the incident light is provided in pulses. In some embodiments, the optical fiber is a multi-core optical fiber including a plurality of core fibers. In some embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

In some embodiments, the external magnetic device is an electromagnetic device. Other embodiments disclose a medical instrument system for inserting a medical instrument within a patient body, the system comprising the medical instrument comprising an optical fiber having one or more of core fibers and a first tension cable that extends longitudinally from a proximal end of the medical instrument to a distal end of the medical instrument, wherein application of tension to a proximal end of the first tension cable causes formation of a curvature at the distal end of the medical instrument, a console including one or more processors and a non-transitory computer-readable medium having stored thereon logic, when executed by the one or more processors, causes operations including providing an incident light signal to the optical fiber, receiving reflected light signals of different spectral widths of the incident light by the optical fiber, processing the reflected light signals associated with the optical fiber, and determining a location of a distal tip of the medical instrument within the patient body.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In some embodiments, the optical fiber is a single-core optical fiber, and wherein the incident light is provided in pulses. In some embodiments, the optical fiber is a multi-core optical fiber including a plurality of core fibers. In some embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter. In some embodiments, the medical instrument is configured to be rotated around a longitudinal axis in order to direct the curvature in a particular direction.

Other embodiments disclose a method for placing a medical instrument into a body of a patient, the method comprising providing an incident light signal to an optical fiber disposed within the medical instrument, the optical fiber having one or more core fibers and a first tension cable that extends longitudinally from a proximal end of the medical instrument to a distal end of the medical instrument, wherein application of tension to a proximal end of the first tension cable causes formation of a curvature at the distal end of the medical instrument, receiving reflected light signals of different spectral widths of the incident light by the optical fiber, processing the reflected light signals associated with the optical fiber and determining a location of a distal tip of the medical instrument within the patient body.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In some embodiments, the optical fiber is a single-core optical fiber, and wherein the incident light is provided in pulses. In some embodiments, the optical fiber is a multi-core optical fiber including a plurality of core fibers. In some embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter. In some embodiments, the medical instrument is configured to be rotated around a longitudinal axis in order to direct the curvature in a particular direction.

Other embodiments disclose a medical assembly system for inserting a medical assembly within a patient body, the system comprising the medical assembly comprising a first medical instrument including a lumen, and a second medical instrument including an optical fiber having one or more of core fibers, the second medical instrument is configured to advance or retract within the lumen of the first medical instrument, wherein the first medical instrument has flexural stiffness that is greater than a flexural stiffness of the second medical instrument. The medical assembly includes a console including one or more processors and a non-transitory computer-readable medium having stored thereon logic, when executed by the one or more processors, causes operations including providing an incident light signal to the optical fiber, receiving reflected light signals of different spectral widths of the incident light by the optical fiber, processing the reflected light signals associated with the optical fiber, and determining a location of a distal tip of the medical instrument within the patient body and that a curvature is present in a distal tip of the medical assembly, wherein the curvature is formed from the second medical instrument advancing beyond a distal end of the first medical instrument.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In some embodiments, the optical fiber is a single-core optical fiber, and wherein the incident light is provided in pulses. In some embodiments, the optical fiber is a multi-core optical fiber including a plurality of core fibers. In some embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

Other embodiments disclose a method for placing a medical assembly into a body of a patient, the medical assembly including a first medical instrument and a second medical instrument, the method comprising providing an incident light signal to an optical fiber disposed within the second medical instrument, the optical fiber having one or more core fibers, the second medical instrument is configured to advance or retract within the lumen of the first medical instrument, and wherein the first medical instrument has flexural stiffness that is greater than a flexural stiffness of the second medical instrument, receiving reflected light signals of different spectral widths of the incident light by the optical fiber, processing the reflected light signals associated with the optical fiber and determining a location of a distal tip of the medical instrument within the patient body and that a curvature is present in a distal tip of the medical assembly, wherein the curvature is formed from the second medical instrument advancing beyond a distal end of the first medical instrument.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In some embodiments, the optical fiber is a single-core optical fiber, and wherein the incident light is provided in pulses. In some embodiments, the optical fiber is a multi-core optical fiber including a plurality of core fibers. In some embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

Other embodiments disclose a medical instrument system for inserting a medical instrument within a patient body, the system comprising the medical instrument comprising an optical fiber having one or more of core fibers, a stiffening stylet and an adjustment mechanism, wherein actuation of the adjustment mechanism moves the stiffening stylet in a proximal or distal direction, and wherein the stiffening stylet has flexural stiffness that is greater than a flexural stiffness of both of a cladding of the medical instrument and the optical fiber, a console including one or more processors and a non-transitory computer-readable medium having stored thereon logic, when executed by the one or more processors, causes operations including providing an incident light signal to the optical fiber, receiving reflected light signals of different spectral widths of the incident light by the optical fiber, processing the reflected light signals associated with the optical fiber, and determining a location of a distal tip of the medical instrument within the patient body.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In some embodiments, the optical fiber is a single-core optical fiber, and wherein the incident light is provided in pulses. In some embodiments, the optical fiber is a multi-core optical fiber including a plurality of core fibers.

In some embodiments, the logic, when executed by the one or more processors, causes further operations including generating a display indicating the location of the distal tip of the optical fiber within the patient body. In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

In some embodiments, the adjustment mechanism includes a proximal collar, a distal collar and a pair of hinged arms, wherein the proximal collar is coupled to the stiffening stylet, and wherein actuation of the adjustment mechanism includes movement of the proximal collar in the proximal or distal direction. In some embodiments, the distal collar remains stationary.

Other embodiments disclose a method for placing a medical instrument into a body of a patient, the method comprising providing an incident light signal to an optical fiber disposed within the medical instrument, the optical fiber having one or more core fibers a stiffening stylet and an adjustment mechanism, wherein actuation of the adjustment mechanism moves the stiffening stylet in a proximal or distal direction, and wherein the stiffening stylet has flexural stiffness that is greater than a flexural stiffness of both of a cladding of the medical instrument and the optical fiber, receiving reflected light signals of different spectral widths of the incident light by the optical fiber, processing the reflected light signals associated with the optical fiber and determining a location of a distal tip of the medical instrument within the patient body.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In some embodiments, the optical fiber is a single-core optical fiber, and wherein the incident light is provided in pulses.

In some embodiments, the optical fiber is a multi-core optical fiber including a plurality of core fibers. In some embodiments, the logic, when executed by the one or more processors, causes further operations including generating a display indicating the location of the distal tip of the optical fiber within the patient body. In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

In some embodiments, the adjustment mechanism includes a proximal collar, a distal collar, and a pair of hinged arms, wherein the proximal collar is coupled to the stiffening stylet, and wherein actuation of the adjustment mechanism includes movement of the proximal collar in the proximal or distal direction. In some embodiments, the distal collar remains stationary.

In some embodiments, the medical instrument is configured for insertion within a medical device, such as a catheter, for example. In further embodiments, the medical instrument is configured for reuse across multiple medical devices. In use, the medical instrument may be inserted within a first medical device, removed therefrom, subsequently inserted within a second medical device. In some embodiments, the medical instrument may be re-sterilized between uses.

In some embodiments, a method may include advancing the medical instrument along a vasculature of a first patient, removing the medical instrument from the first patient, sterilizing the medical instrument after removing the medical instrument from the first patient, and advancing the same medical instrument along a vasculature of a second patient.

In some embodiments, the medical instrument is configured for insertion within a medical device, such as within a lumen of the medical device. In some embodiments, the medical instrument is reusable across multiple medical devices. The medical instrument may include a disposable cover configured to cover the medical instrument for each use of the medical instrument. The medical instrument may include a film or coating over an outer jacket of the medical instrument, where the film or coating is configured to be replenishable for each use of the medical instrument.

In some embodiments, the medical instrument is configured to be sterilized by dry heat, moist heat optionally in combination with pressure, a biocide optionally in combination with pressure, radiation, or a combination thereof. The medical instrument may also be configured to be re-sterilized between uses of the medical instrument.

In some embodiments, the medical instrument includes electrical circuitry and componentry configured for electrocardiography, conductance measurements, or impedance measurements.

Also disclosed herein is a shape-sensing system for medical devices. The shape-sensing system includes, in some embodiments, an optical-fiber insert configured to load into a lumen of a medical device, an optical interrogator, and a console. The optical-fiber insert includes one or more cores and a number of functional layers around the one-or-more cores. The one-or-more cores are of drawn plastic or glass having a number of FBG sensors along at least a distal portion of the optical-fiber insert. The number of functional layers around the one-or-more cores include at least an outer jacket. The optical interrogator is configured to send input optical signals into the optical-fiber insert and receive FBG sensor-reflected optical signals from the optical-fiber insert. The console includes memory and one or more processors configured to convert the FBG sensor-reflected optical signals from the optical-fiber insert into plottable data by way of optical signal-converter logic for displaying a graphical representation of the optical-fiber insert including a shape of the optical-fiber insert and a location of the optical-fiber insert in a patient.

In some embodiments, the optical-fiber insert is an optical-fiber stylet, an optical-fiber guidewire, or an optical-fiber obturator.

In some embodiments, the optical-fiber insert is reusable.

In some embodiments, the shape-sensing system further includes a disposable cover. The cover is configured to cover the optical-fiber insert for each use of the optical-fiber insert.

In some embodiments, the optical-fiber insert includes a film or coating over the outer jacket. The film or coating is configured to be replenishable for each use of the optical-fiber insert.

In some embodiments, the optical-fiber insert is configured to be sterilizable by dry heat, moist heat optionally in combination with pressure, a biocide optionally in combination with pressure, radiation, or a combination thereof.

In some embodiments, the optical-fiber insert includes a quick-connect connector about a proximal end of the optical-fiber insert. The quick-connect connector is configured for quickly connecting to or disconnecting from a complementary quick-connect connector of the console.

In some embodiments, the console is configured to automatically instantiate one or more shape-sensing processes when the optical-fiber insert is connected to the console.

In some embodiments, the medical device is an intravascular medical device selected from a catheter, a needle, an introducer, a dilator, a tunneler, and a combination of two or more of the foregoing intravascular medical devices loaded into one another.

In some embodiments, the optical-fiber insert is configured to proximally load into the intravascular medical device.

In some embodiments, the optical-fiber insert is configured to load into either end of two ends of the tunneler.

In some embodiments, the shape-sensing system further includes an optical-fiber insert holder. The optical-fiber insert holder is configured to accept the optical-fiber insert through a through hole of the optical-fiber insert holder. The optical-fiber insert holder is also configured to hold the optical-fiber insert therein with friction and, thereby, prevent proximal movement of the optical-fiber insert while the optical-fiber insert is disposed in the medical device.

In some embodiments, the optical-fiber insert includes electrical circuitry and componentry. The electrical circuitry and componentry is configured for electrocardiography, conductance measurements, or impedance measurements.

In some embodiments, the optical interrogator is an integrated optical interrogator integrated into the console.

In some embodiments, the shape-sensing system further includes a display screen. The display screen is configured for displaying the graphical representation of the optical-fiber insert including the shape of the optical-fiber insert and the location of the optical-fiber insert in the patient.

Also disclosed herein is an optical-fiber insert configured to load into a lumen of a medical device. The optical-fiber insert includes, in some embodiments, one or more cores and a number of functional layers around the one-or-more cores. The one-or-more cores are of drawn plastic or glass having a number of FBG sensors along at least a distal portion of the optical-fiber insert. The FBG sensors are configured to reflect input optical signals from an optical interrogator back to the optical interrogator as FBG sensor-reflected optical signal. The number of functional layers around the one-or-more cores include at least an outer jacket.

In some embodiments, the optical-fiber insert is an optical-fiber stylet, an optical-fiber guidewire, or an optical-fiber obturator.

In some embodiments, the optical-fiber insert is reusable.

In some embodiments, the optical-fiber insert further includes a disposable cover. The cover is configured to cover the optical-fiber insert for each use of the optical-fiber insert.

In some embodiments, the optical-fiber insert includes a film or coating over the outer jacket. The film or coating is configured to be replenishable for each use of the optical-fiber insert.

In some embodiments, the optical-fiber insert is configured to be sterilizable by dry heat, moist heat optionally in combination with pressure, a biocide optionally in combination with pressure, radiation, or a combination thereof.

In some embodiments, the optical-fiber insert includes a quick-connect connector about a proximal end of the optical-fiber insert. The quick-connect connector is configured for quickly connecting to or disconnecting from a complementary quick-connect connector of a console.

In some embodiments, the medical device is an intravascular medical device selected from a catheter, a needle, an introducer, a dilator, a tunneler, and a combination of two or more of the foregoing intravascular medical devices loaded into one another.

In some embodiments, the optical-fiber insert is configured to proximally load into the intravascular medical device.

In some embodiments, the optical-fiber insert is configured to load into either end of two ends of the tunneler.

In some embodiments, the optical-fiber insert further includes an optical-fiber insert holder. The optical-fiber insert holder is configured to accept the optical-fiber insert through a through hole of the optical-fiber insert holder. The optical-fiber insert holder is also configured to hold the optical-fiber insert therein with friction and, thereby, prevent proximal movement of the optical-fiber insert while the optical-fiber insert is disposed in the medical device.

In some embodiments, the optical-fiber insert includes electrical circuitry and componentry. The electrical circuitry and componentry is configured for electrocardiography, conductance measurements, or impedance measurements.

Also disclosed herein is a method of an optical-fiber insert. The method includes, in some embodiments, a loading step, a connecting step, and an advancing step. The loading step includes loading the optical-fiber insert into an intravascular medical device. The optical-fiber insert includes one or more cores and a number of functional layers around the one-or-more cores. The one-or-more cores are of drawn plastic or glass having a number of FBG sensors along at least a distal portion of the optical-fiber insert configured for shape-sensing with the optical-fiber insert. The number of functional layers around the one-or-more cores includes at least an outer jacket. The connecting step includes connecting the optical-fiber insert to a console by way of connecting a quick-connect connector about a proximal end of the optical-fiber insert to a complementary quick-connect connector of a console. The advancing step includes advancing the optical-fiber insert through a vasculature of a patient independent of or together with the medical device.

In some embodiments, the optical-fiber insert is an optical-fiber stylet, an optical-fiber guidewire, or an optical-fiber obturator.

In some embodiments, the loading step includes loading the optical-fiber insert into a catheter, a needle, an introducer, a dilator, a tunneler, or a combination of two or more of the foregoing medical devices loaded into one another.

In some embodiments, the loading step occurs a number of times in a single medical procedure for a number of medical devices used in the medical procedure. The optical-fiber insert each time of the number of times the loading step occurs is a same optical-fiber insert.

In some embodiments, the connecting step includes automatically instantiating one or more shape-sensing processes of the console for shape-sensing with the optical-fiber insert. The one-or-more shape-sensing processes include sending input optical signals from an optical interrogator to the optical-fiber insert and receiving FBG sensor-reflected optical signals by the optical interrogator from the optical-fiber insert during the advancing step.

In some embodiments, the method further includes an instantiating step. The instantiating step includes instantiating one or more electrical tip-location processes of the console. The one-or-more electrical tip-location processes are configured to locate a distal tip of the optical-fiber insert by way of electrocardiography, conductance measurements, or impedance measurements using electrical circuitry and componentry of the optical-fiber insert configured therefor.

In some embodiments, the method further includes a ceasing step. The ceasing step includes ceasing to advance the optical-fiber insert through the vasculature of the patient upon reaching a target anatomical location as determined by the shape-sensing of the optical-fiber insert.

In some embodiments, the method further includes another inserting step and an adjusting step. The other inserting step includes inserting the optical-fiber insert through a through hole of an optical-fiber insert holder. The adjusting step includes adjusting a location of the optical-fiber insert holder over the optical-fiber insert. The optical-fiber insert holder is configured to hold the optical-fiber insert in the optical-fiber insert holder with friction and, thereby, prevent proximal movement of the optical-fiber through the medical device upon reaching the target anatomical location.

In some embodiments, the method further includes a covering step and a removing step. The covering step includes covering the optical-fiber insert with a disposable cover before the loading step. The removing step includes removing the cover from the optical-fiber insert when finished using the optical-fiber insert.

In some embodiments, the method further includes another removing step and a replenishing step. The other removing step includes removing a film or coating from the outer jacket of the optical-fiber insert when finished using the optical-fiber insert. The replenishing step includes replenishing the film or coating over the outer jacket before the loading step.

In some embodiments, the method further includes a sterilizing step. The sterilizing step includes sterilizing the optical-fiber insert by dry heat, moist heat optionally in combination with pressure, a biocide optionally in combination with pressure, radiation, or a combination thereof.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 3A is a first exemplary embodiment of the stylet of FIG. 1A supporting both an optical and electrical signaling in accordance with some embodiments;

FIG. 3B is a cross sectional view of the stylet of FIG. 3A in accordance with some embodiments;

FIG. 4A is a second exemplary embodiment of the stylet of FIG. 1B in accordance with some embodiments;

FIG. 4B is a cross sectional view of the stylet of FIG. 4A in accordance with some embodiments;

FIG. 10C is a second embodiment of a medical instrument including a plurality of optical fibers, a plurality of tension cables and a set of tension controls in accordance with some embodiments;

FIG. 10D is a third embodiment of a medical instrument including a plurality of optical fibers and a plurality of tension cables in accordance with some embodiments;

FIG. 11A is an illustration of a catheter having a stylet advancing therethrough where the stylet supports optical signaling in accordance with some embodiments;

FIG. 11B is a cross sectional perspective view of a vessel within a vasculature having the catheter and stylet assembly of FIG. 11A advancing within the vasculature based on a direction of blood flow in accordance with some embodiments;

FIG. 11D is an illustration of a sheathed fiber optic core where the fiber optic core is configured to advance or retract relative to the sheath in accordance with some embodiments;

FIGS. 12A-12B are illustrations of a medical instrument supporting optical signaling and including an adjustment stiffening stylet in accordance with some embodiments;

DETAILED DESCRIPTION

Figure 1A:
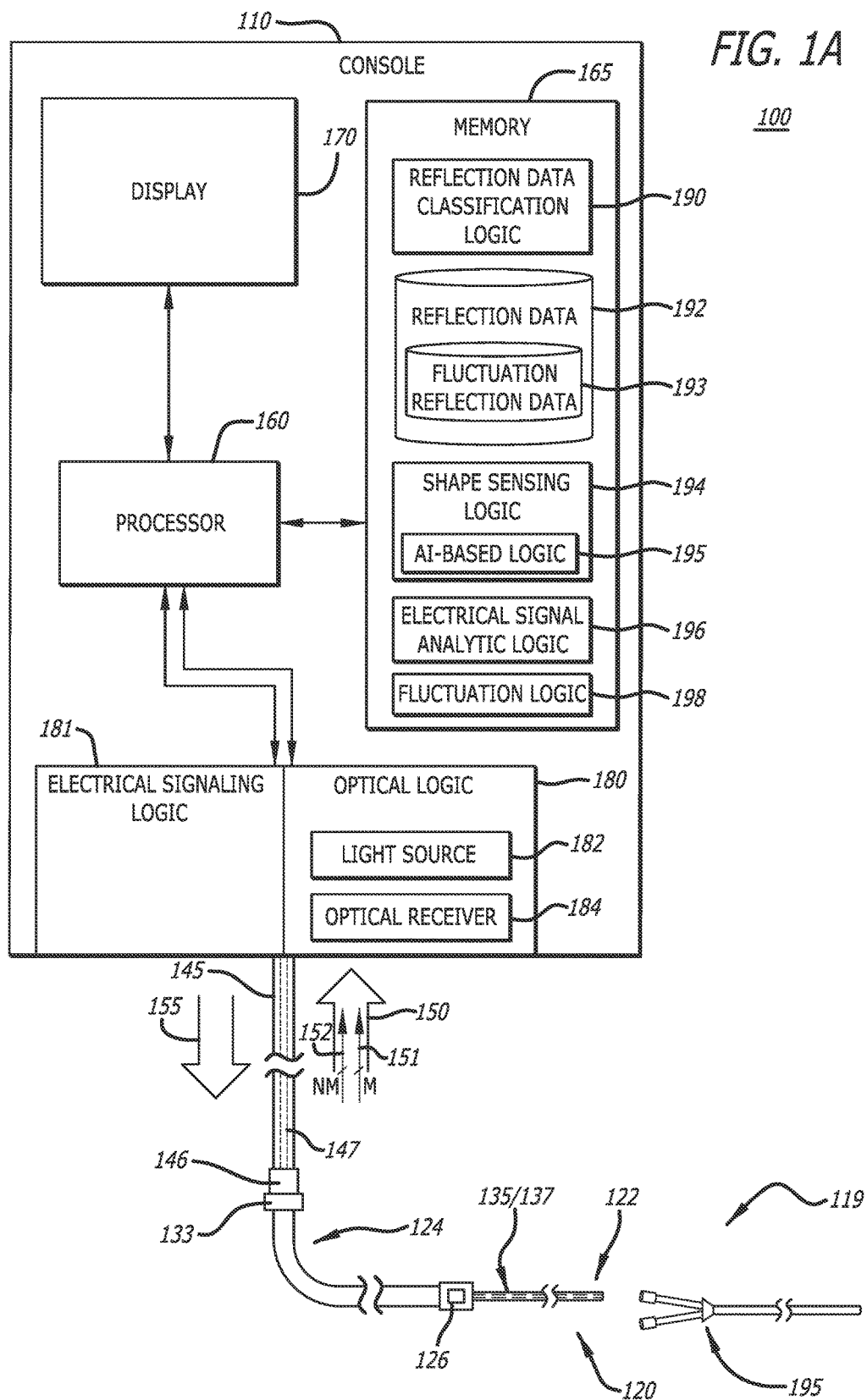
FIG. 1A is an illustrative embodiment of a medical instrument monitoring system including a medical instrument with optic shape sensing and fiber optic-based oximetry capabilities in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random-access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Referring to FIG. 1A, an illustrative embodiment of a medical instrument monitoring system including a medical instrument with optic shape sensing and fiber optic-based oximetry capabilities is shown in accordance with some embodiments. As shown, the system 100 generally includes a console 110 and a stylet assembly 119 communicatively coupled to the console 110. For this embodiment, the stylet assembly 119 includes an elongate probe (e.g., stylet) 120 on its distal end 122 and a console connector 133 on its proximal end 124, where the stylet 120 is configured to advance within a patient vasculature either through, or in conjunction with, a catheter 195. The console connector 133 enables the stylet assembly 119 to be operably connected to the console 110 via an interconnect 145 including one or more optical fibers 147 (hereinafter, "optical fiber(s)") and a conductive medium terminated by a single optical/electric connector 146 (or terminated by dual connectors). Herein, the connector 146 is configured to engage (mate) with the console connector 133 to allow for the propagation of light between the console 110 and the stylet assembly 119 as well as the propagation of electrical signals from the stylet 120 to the console 110.

An exemplary implementation of the console 110 includes a processor 160, a memory 165, a display 170 and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Pat. No. 10,992,078, the entire contents of which are incorporated by reference herein. The processor 160, with access to the memory 165 (e.g., non-volatile memory or non-transitory, computer-readable medium), is included to control functionality of the console 110 during operation. As shown, the display 170 may be a liquid crystal diode (LCD) display integrated into the console 110 and employed as a user interface to display information to the clinician, especially during a catheter placement procedure (e.g., cardiac catheterization). In another embodiment, the display 170 may be separate from the console 110. Although not shown, a user interface is configured to provide user control of the console 110.

For both embodiments, the content depicted by the display 170 may change according to which mode the stylet 120 is configured to operate: optical, TLS, ECG, or another modality. In TLS mode, the content rendered by the display 170 may constitute a two-dimensional (2D) or three-dimensional (3D) representation of the physical state (e.g., length, shape, form, and/or orientation) of the stylet 120 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below According to one embodiment of the disclosure, an activation control 126, included on the stylet assembly 119, may be used to set the stylet 120 into a desired operating mode and selectively alter operability of the display 170 by the clinician to assist in medical device placement. For example, based on the modality of the stylet 120, the display 170 of the console 110 can be employed for optical modality-based guidance during catheter advancement through the vasculature or TLS modality to determine the physical state (e.g., length, form, shape, orientation, etc.) of the stylet 120. In one embodiment, information from multiple modes, such as optical, TLS or ECG for example, may be displayed concurrently (e.g., at least partially overlapping in time).

Referring still to FIG. 1A, the optical logic 180 is configured to support operability of the stylet assembly 119 and enable the return of information to the console 110, which may be used to determine the physical state associated with the stylet 120 along with monitored electrical signals such as ECG signaling via an electrical signaling logic 181 that supports receipt and processing of the received electrical signals from the stylet 120 (e.g., ports, analog-to-digital conversion logic, etc.). The physical state of the stylet 120 may be based on changes in characteristics of the reflected light signals 150 received at the console 110 from the stylet 120. The characteristics may include shifts in wavelength caused by strain on certain regions of the core fibers integrated within an optical fiber core 135 positioned within or operating as the stylet 120, as shown below. As discussed herein, the optical fiber core 135 may be comprised of core fibers $137_1$-$137_M$ (M=1 for a single core, and M≥2 for a multi-core), where the core fibers $137_1$-$137_M$ may collectively be referred to as core fiber(s) 137. Unless otherwise specified or the instant embodiment requires an alternative interpretation, embodiments discussed herein will refer to a multi-core optical fiber 135. From information associated with the reflected light signals 150, the console 110 may determine (through computation or extrapolation of the wavelength shifts) the physical state of the stylet 120, and that of the catheter 195 configured to receive the stylet 120.

According to one embodiment of the disclosure, as shown in FIG. 1A, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the multi-core optical fiber core 135 within the stylet 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the multi-core optical fiber 135 deployed within the stylet 120, and (ii) translate the reflected light signals 150 into reflection data (from repository 192), namely data in the form of electrical signals representative of the reflected light signals including wavelength shifts caused by strain. The reflected light signals 150 associated with different spectral widths may include reflected light signals 151 provided from sensors positioned in the center core fiber (reference) of the multi-core optical fiber 135 and reflected light signals 152 provided from sensors positioned in the periphery core fibers of the multi-core optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the processor 160, which governs their operation. Also, the optical receiver 184 is operably coupled to provide the reflection data (from repository 192) to the memory 165 for storage and processing by reflection data classification logic 190. The reflection data classification logic 190 may be configured to: (i) identify which core fibers pertain to which of the received reflection data (from repository 192) and (ii) segregate the reflection data stored with a repository 192 provided from reflected light signals 150 pertaining to similar regions of the stylet 120 or spectral widths into analysis groups. The reflection data for each analysis group is made available to shape sensing logic 194 for analytics.

According to one embodiment of the disclosure, the shape sensing logic 194 is configured to compare wavelength shifts measured by sensors deployed in each periphery core fiber at the same measurement region of the stylet 120 (or same spectral width) to the wavelength shift at a center core fiber of the multi-core optical fiber 135 positioned along central axis and operating as a neutral axis of bending. From these analytics, the shape sensing logic 194 may determine the shape the core fibers have taken in 3D space and may further determine the current physical state of the catheter 195 in 3D space for rendering on the display 170.

According to one embodiment of the disclosure, the shape sensing logic 194 may generate a rendering of the current physical state of the stylet 120 (and potentially the catheter 195), based on heuristics or run-time analytics. For example, the shape sensing logic 194 may be configured in accordance with machine-learning techniques to access a data store (library) with pre-stored data (e.g., images, etc.) pertaining to different regions of the stylet 120 (or catheter 195) in which reflected light from core fibers have previously experienced similar or identical wavelength shifts. From the pre-stored data, the current physical state of the stylet 120 (or catheter 195) may be rendered. Alternatively, as another example, the shape sensing logic 194 may be configured to determine, during run-time, changes in the physical state of each region of the multi-core optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the multi-core optical fiber 135 to the wavelength shift generated by a sensor of the center core fiber at the same cross-sectional region. It is contemplated that other processes and procedures may be performed to utilize the wavelength shifts as measured by sensors along each of the core fibers within the multi-core optical fiber 135 to render appropriate changes in the physical state of the stylet 120 (and/or catheter 195), especially to enable guidance of the stylet 120, when positioned at a distal tip of the catheter 195, within the vasculature of the patient and at a desired destination within the body.

The console 110 may further include electrical signaling logic 181, which is positioned to receive one or more electrical signals from the stylet 120. The stylet 120 is configured to support both optical connectivity as well as electrical connectivity. The electrical signaling logic 181 receives the electrical signals (e.g., ECG signals) from the stylet 120 via the conductive medium. The electrical signals may be processed by electrical signal logic 196, executed by the processor 160, to determine ECG waveforms for display.

Additionally, the console 110 includes a fluctuation logic 198 that is configured to analyze at least a subset of the wavelength shifts measured by sensors deployed in each of the core fibers 137. In particular, the fluctuation logic 198 is configured to analyze wavelength shifts measured by sensors of core fibers 137, where such corresponds to an analysis of the fluctuation of the distal tip of the stylet 120 (or "tip fluctuation analysis"). In some embodiments, the fluctuation logic 198 analyzes the wavelength shifts measured by sensors at a distal end of the core fibers 137. The tip fluctuation analysis includes at least a correlation of detected movements of the distal tip of the stylet 120 (or other medical device or instrument) with experiential knowledge comprising previously detected movements (fluctuations), and optionally, other current measurements such as ECG signals. The experiential knowledge may include previously detected movements in various locations within the vasculature (e.g., SVC, Inferior Vena Cava (IVC), right atrium, azygos vein, other blood vessels such as arteries and veins) under normal, healthy conditions and in the presence of defects (e.g., vessel constriction, vasospasm, vessel occlusion, etc.). Thus, the tip fluctuation analysis may result in a confirmation of tip location and/or detection of a defect affecting a blood vessel.

It should be noted that the fluctuation logic 198 need not perform the same analyses as the shape sensing logic 194. For instance, the shape sensing logic 194 determines a 3D shape of the stylet 120 by comparing wavelength shifts in outer core fibers of a multi-core optical fiber to a center, reference core fiber. The fluctuation logic 198 may instead correlate the wavelength shifts to previously measured wavelength shifts and optionally other current measurements without distinguishing between wavelength shifts of outer core fibers and a center, reference core fiber as the tip fluctuation analysis need not consider direction or shape within a 3D space.

In some embodiments, e.g., those directed at tip location confirmation, the analysis of the fluctuation logic 198 may utilize electrical signals (e.g., ECG signals) measured by the electrical signaling logic 181. For example, the fluctuation logic 198 may compare the movements of a subsection of the stylet 120 (e.g., the distal tip) with electrical signals indicating impulses of the heart (e.g., the heartbeat). Such a comparison may reveal whether the distal tip is within the SVC or the right atrium based on how closely the movements correspond to a rhythmic heartbeat.

In various embodiments, a display and/or alert may be generated based on the fluctuation analysis. For instance, the fluctuation logic 198 may generate a graphic illustrating the detected fluctuation compared to previously detected tip fluctuations and/or the anatomical movements of the patient body such as rhythmic pulses of the heart and/or expanding and contracting of the lungs. In one embodiment, such a graphic may include a dynamic visualization of the present medical device moving in accordance with the detected fluctuations adjacent to a secondary medical device moving in accordance with previously detected tip fluctuations. In some embodiments, the location of a subsection of the medical device may be obtained from the shape sensing logic 194 and the dynamic visualization may be location-specific (e.g., such that the previously detected fluctuations illustrate expected fluctuations for the current location of the subsection). In alternative embodiments, the dynamic visualization may illustrate a comparison of the dynamic movements of the subsection to one or more subsections moving in accordance with previously detected fluctuations of one or more defects affecting the blood vessel.

According to one embodiment of the disclosure, the fluctuation logic 198 may determine whether movements of one or more subsections of the stylet 120 indicate a location of a particular subsection of the stylet 120 or a defect affecting a blood vessel and, as a result, of the catheter 195, based on heuristics or run-time analytics. For example, the fluctuation logic 198 may be configured in accordance with machine-learning techniques to access a data store (library) with pre-stored data (e.g., experiential knowledge of previously detected tip fluctuation data, etc.) pertaining to different regions (subsections) of the stylet 120. Specifically, such an embodiment may include processing of a machine-learning model trained using the experiential knowledge, where the detected fluctuations serve as input to the trained model and processing of the trained model results in a determination as to how closely the detected fluctuations correlate to one or more locations within the vasculature of the patient and/or one or more defects affecting a blood vessel.

In some embodiments, the fluctuation logic 198 may be configured to determine, during run-time, whether movements of one or more subsections of the stylet 120 (and the catheter 195) indicate a location of a particular subsection of the stylet 120 or a defect affecting a blood vessel, based on at least (i) resultant wavelength shifts experienced by the core fibers 137 within the one or more subsections, and (ii) the correlation of these wavelength shifts generated by sensors positioned along different core fibers at the same cross-sectional region of the stylet 120 (or the catheter 195) to previously detected wavelength shifts generated by corresponding sensors in a core fiber at the same cross-sectional region. It is contemplated that other processes and procedures may be performed to utilize the wavelength shifts as measured by sensors along each of the core fibers 137 to render appropriate movements in the distal tip of the stylet 120 and/or the catheter 195.

Figure 1B:
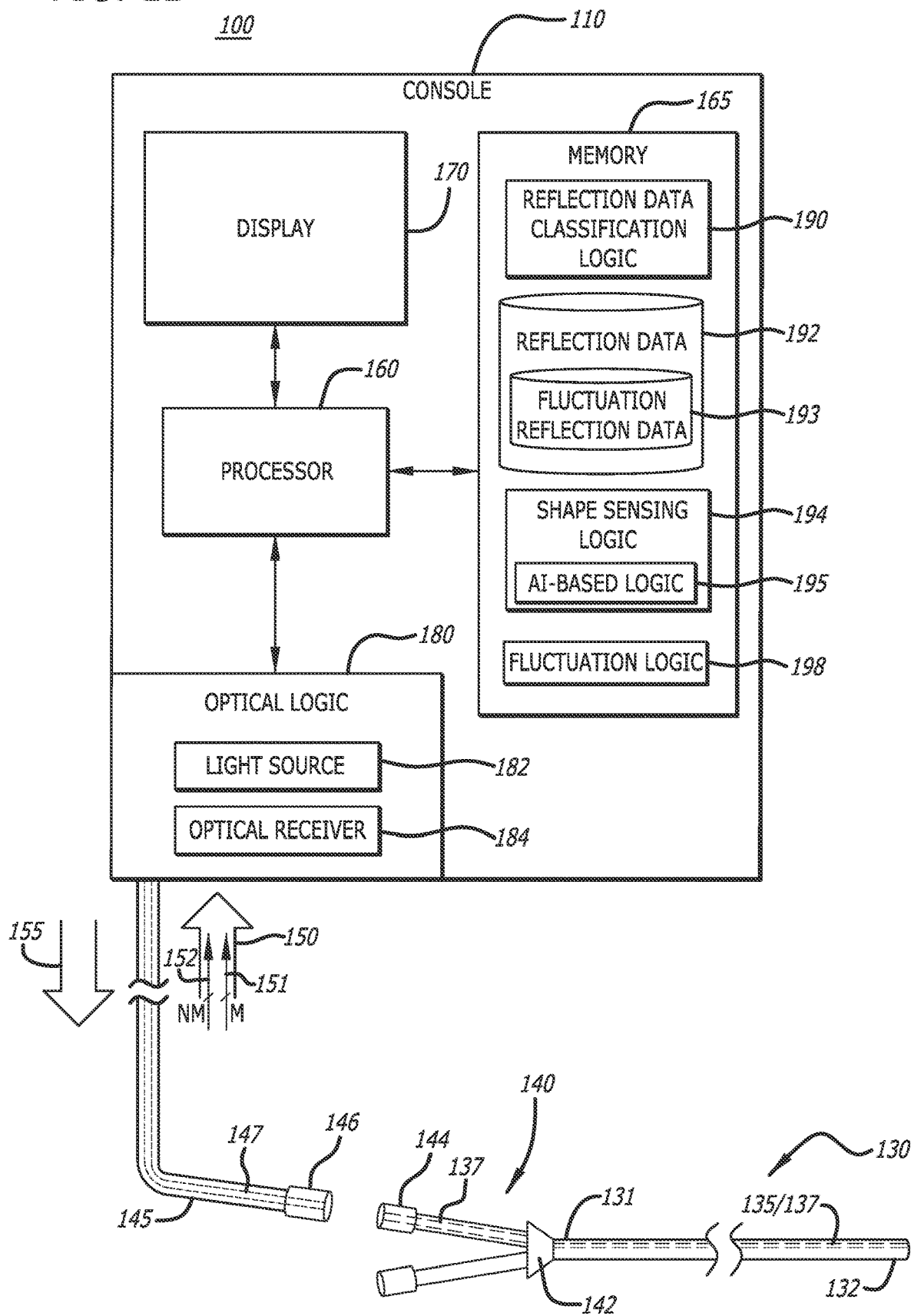
FIG. 1B is an alternative illustrative embodiment of the medical instrument monitoring system 100 in accordance with some embodiments.

Referring to FIG. 1B, an alternative exemplary embodiment of a medical instrument monitoring system 100 is shown. Herein, the medical instrument monitoring system 100 features a console 110 and a medical instrument 130 communicatively coupled to the console 110. For this embodiment, the medical instrument 130 corresponds to a catheter, which features an integrated tubing with two or more lumen extending between a proximal end 131 and a distal end 132 of the integrated tubing. The integrated tubing (sometimes referred to as "catheter tubing") is in communication with one or more extension legs 140 via a bifurcation hub 142. An optical-based catheter connector 144 may be included on a proximal end of at least one of the extension legs 140 to enable the catheter 130 to operably connect to the console 110 via an interconnect 145 or another suitable component. Herein, the interconnect 145 may include a connector 146 that, when coupled to the optical-based catheter connector 144, establishes optical connectivity between one or more optical fibers 147 (hereinafter, "optical fiber(s)") included as part of the interconnect 145 and core fibers 137 deployed within the catheter 130 and integrated into the tubing. Alternatively, a different combination of connectors, including one or more adapters, may be used to optically connect the optical fiber(s) 147 to the core fibers 137 within the catheter 130. The core fibers 137 deployed within the catheter 130 as illustrated in FIG. 1B include the same characteristics and perform the same functionalities as the core fibers 137 deployed within the stylet 120 of FIG. 1A.

The optical logic 180 is configured to support graphical rendering of the catheter 130, most notably the integrated tubing of the catheter 130, based on characteristics of the reflected light signals 150 received from the catheter 130. The characteristics may include shifts in wavelength caused by strain on certain regions of the core fibers 137 integrated within (or along) a wall of the integrated tubing, which may be used to determine (through computation or extrapolation of the wavelength shifts) the physical state of the catheter 130, notably its integrated tubing or a portion of the integrated tubing such as a tip or distal end of the tubing to read fluctuations (real-time movement) of the tip (or distal end).

More specifically, the optical logic 180 includes a light source 182. The light source 182 is configured to transmit the broadband incident light 155 for propagation over the optical fiber(s) 147 included in the interconnect 145, which are optically connected to multiple core fibers 137 within the catheter tubing. Herein, the optical receiver 184 is configured to: (i) receive returned optical signals, namely reflected light signals 150 received from optical fiber-based reflective gratings (sensors) fabricated within each of the core fibers 137 deployed within the catheter 130, and (ii) translate the reflected light signals 150 into reflection data (from repository 192), namely data in the form of electrical signals representative of the reflected light signals including wavelength shifts caused by strain. The reflected light signals 150 associated with different spectral widths include reflected light signals 151 provided from sensors positioned in the center core fiber (reference) of the catheter 130 and reflected light signals 152 provided from sensors positioned in the outer core fibers of the catheter 130, as described below.

As noted above, the shape sensing logic 194 is configured to compare wavelength shifts measured by sensors deployed in each outer core fiber at the same measurement region of the catheter (or same spectral width) to the wavelength shift at the center core fiber positioned along central axis and operating as a neutral axis of bending. From these analytics, the shape sensing logic 190 may determine the shape the core fibers have taken in 3D space and may further determine the current physical state of the catheter 130 in 3D space for rendering on the display 170.

According to one embodiment of the disclosure, the shape sensing logic 194 may generate a rendering of the current physical state of the catheter 130, especially the integrated tubing, based on heuristics or run-time analytics. For example, the shape sensing logic 194 may be configured in accordance with machine-learning techniques to access a data store (library) with pre-stored data (e.g., images, etc.) pertaining to different regions of the catheter 130 in which the core fibers 137 experienced similar or identical wavelength shifts. From the pre-stored data, the current physical state of the catheter 130 may be rendered. Alternatively, as another example, the shape sensing logic 194 may be configured to determine, during run-time, changes in the physical state of each region of the catheter 130, notably the tubing, based on at least (i) resultant wavelength shifts experienced by the core fibers 137 and (ii) the relationship of these wavelength shifts generated by sensors positioned along different outer core fibers at the same cross-sectional region of the catheter 130 to the wavelength shift generated by a sensor of the center core fiber at the same cross-sectional region. It is contemplated that other processes and procedures may be performed to utilize the wavelength shifts as measured by sensors along each of the core fibers 137 to render appropriate changes in the physical state of the catheter 130.

Figure 2:
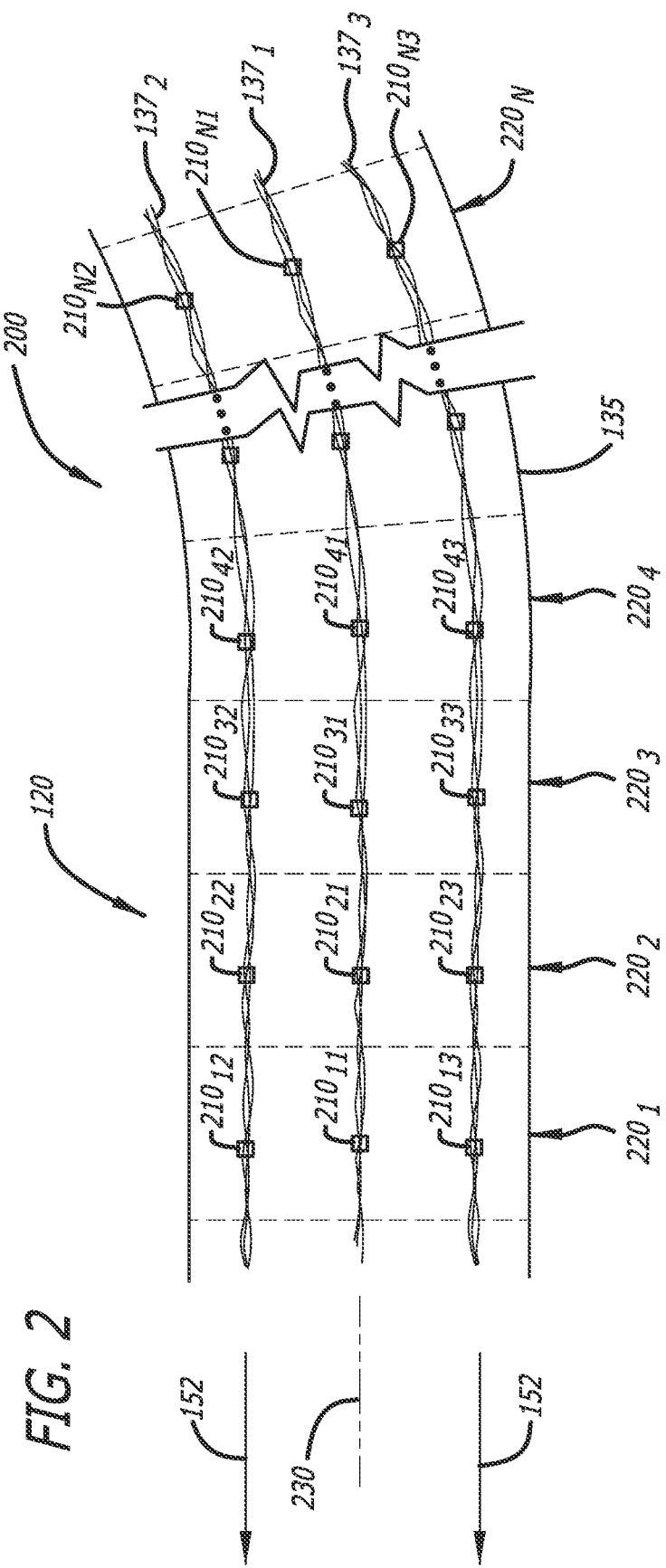
FIG. 2 is an exemplary embodiment of a structure of a section of the multi-core optical fiber included within the stylet 120 of FIG. 1A in accordance with some embodiments.

Referring to FIG. 2, an exemplary embodiment of a structure of a section of the multi-core optical fiber included within the stylet 120 of FIG. 1A is shown in accordance with some embodiments. The multi-core optical fiber section 200 of the multi-core optical fiber 135 depicts certain core fibers $137_1$-$137_M$ (M≥2, M=4 as shown, see FIG. 3A) along with the spatial relationship between sensors (e.g., reflective gratings) $210_{11}$-$210_{NM}$ (N≥2; M≥2) present within the core fibers $137_1$-$137_M$, respectively. As noted above, the core fibers $137_1$-$137_M$ may be collectively referred to as "the core fibers 137."

As shown, the section 200 is subdivided into a plurality of cross-sectional regions $220_1$-$220_N$, where each cross-sectional region $220_1$-$220_N$ corresponds to reflective gratings $210_{11}$-$210_{14}$ ... $210_{N1}$-$210_{N4}$. Some or all of the cross-sectional regions $220_1$ ... $220_N$ may be static (e.g., prescribed length) or may be dynamic (e.g., vary in size among the regions $220_1$ ... $220_N$). A first core fiber $137_1$ is positioned substantially along a center (neutral) axis 230 while core fiber $137_2$ may be oriented within the cladding of the multi-core optical fiber 135, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$. As examples, FIGS. 3A-4B provides illustrations of such.

Referencing the first core fiber $137_1$ as an illustrative example, when the stylet 120 is operative, each of the reflective gratings $210_1$-$210_N$ reflects light for a different spectral width. As shown, each of the gratings $210_{1i}$-$210_{Ni}$ (1≤i≤M) is associated with a different, specific spectral width, which would be represented by different center frequencies of $f_1$ ... $f_N$, where neighboring spectral widths reflected by neighboring gratings are non-overlapping according to one embodiment of the disclosure.

Herein, positioned in different core fibers $137_2$-$137_3$ but along at the same cross-sectional regions 220-$220_N$ of the multi-core optical fiber 135, the gratings $210_{12}$-$210_{N2}$ and $210_{13}$-$210_{N3}$ are configured to reflect incoming light at same (or substantially similar) center frequency. As a result, the reflected light returns information that allows for a determination of the physical state of the optical fibers 137 (and the stylet 120) based on wavelength shifts measured from the returned, reflected light. In particular, strain (e.g., compression or tension) applied to the multi-core optical fiber 135 (e.g., at least core fibers $137_2$-$137_3$) results in wavelength shifts associated with the returned, reflected light. Based on different locations, the core fibers $137_1$-$137_4$ experience different types and degree of strain based on angular path changes as the stylet 120 advances in the patient.

For example, with respect to the multi-core optical fiber section 200 of FIG. 2, in response to angular (e.g., radial) movement of the stylet 120 is in the left-veering direction, the fourth core fiber $137_4$ (see FIG. 3A) of the multi-core optical fiber 135 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fibers $137_2$ and $137_3$ will exhibit different changes in wavelength. The differences in wavelength shift of the reflected light signals 150 can be used to extrapolate the physical configuration of the stylet 120 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the multi-core optical fiber 135. These degrees of wavelength change may be used to extrapolate the physical state of the stylet 120. The reflected light signals 150 are reflected back to the console 110 via individual paths over a particular core fiber $137_1$-$137_M$.

Referring to FIG. 3A, a first exemplary embodiment of the stylet of FIG. 1A supporting both an optical and electrical signaling is shown in accordance with some embodiments. Herein, the stylet 120 features a centrally located multi-core optical fiber 135, which includes a cladding 300 and a plurality of core fibers $137_1$-$137_M$ (M≥2; M=4) residing within a corresponding plurality of lumens $320_1$-$320_M$. While the multi-core optical fiber 135 is illustrated within four (4) core fibers $137_1$-$137_4$, a greater number of core fibers $137_1$-$137_M$ (M≥4) may be deployed to provide a more detailed three-dimensional sensing of the physical state (e.g., shape, etc.) of the multi-core optical fiber 135 and the stylet 120 deploying the optical fiber 135.

For this embodiment of the disclosure, the multi-core optical fiber 135 is encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the stylet 120, as a greater spacing may provide a lesser rigidity, and thereby, a more pliable stylet 120.

According to this embodiment of the disclosure, as shown in FIGS. 3A-3B, the core fibers $137_1$-$137_4$ include (i) a central core fiber $137_1$ and (ii) a plurality of periphery core fibers $137_2$-$137_4$, which are maintained within lumens $320_1$-$320_4$ formed in the cladding 300. According to one embodiment of the disclosure, one or more of the lumens $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the multi-core optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_2$-$320_4$ each formed within different areas of the cladding 300 radiating from the first neutral axis 230. In general, the core fibers $137_2$-$137_4$, exclusive of the central core fiber $137_1$, may be positioned at different areas within a cross-sectional area 305 of the cladding 300 to provide sufficient separation to enable three-dimensional sensing of the multi-core optical fiber 135 based on changes in wavelength of incident light propagating through the core fibers $137_2$-$137_4$ and reflected back to the console for analysis.

For example, where the cladding 300 features a circular cross-sectional area 305 as shown in FIG. 3B, the core fibers $137_2$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3A-3B, operating as the conductive medium for the stylet 120, the braided tubing 310 provides mechanical integrity to the multi-core optical fiber 135 and operates as a conductive pathway for electrical signals. For example, the braided tubing 310 may be exposed to a distal tip of the stylet 120. The cladding 300 and the braided tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both for the cladding 300 and the braided tubing 310, as shown.

Referring to FIG. 4A, a second exemplary embodiment of the stylet of FIG. 1A is shown in accordance with some embodiments. Referring now to FIG. 4A, a second exemplary embodiment of the stylet 120 of FIG. 1A supporting both an optical and electrical signaling is shown. Herein, the stylet 120 features the multi-core optical fiber 135 described above and shown in FIG. 3A, which includes the cladding 300 and the first plurality of core fibers $137_1$-$137_M$ (M≥3; M=4 for embodiment) residing within the corresponding plurality of lumens $320_1$-$320_M$. For this embodiment of the disclosure, the multi-core optical fiber 135 includes the central core fiber $137_1$ residing within the first lumen $320_1$ formed along the first neutral axis 230 and the second plurality of core fibers $137_2$-$137_4$ residing within corresponding lumens $320_2$-$320_4$ positioned in different segments within the cross-sectional area 305 of the cladding 300. Herein, the multi-core optical fiber 135 is encapsulated within a conductive tubing 400. The conductive tubing 400 may feature a "hollow" conductive cylindrical member concentrically encapsulating the multi-core optical fiber 135.

Referring to FIGS. 4A-4B, operating as a conductive medium for the stylet 120 in the transfer of electrical signals (e.g., ECG signals) to the console, the conductive tubing 400 may be exposed up to a tip 410 of the stylet 120. For this embodiment of the disclosure, a conductive epoxy 420 (e.g., metal-based epoxy such as a silver epoxy) may be affixed to the tip 410 and similarly joined with a termination/connection point created at a proximal end 430 of the stylet 120. The cladding 300 and the conductive tubing 400, which is positioned concentrically surrounding a circumference of the cladding 300, are contained within the same insulating layer 440. The insulating layer 440 may be a protective conduit encapsulating both for the cladding 300 and the conductive tubing 400, as shown.

Figure 5A:
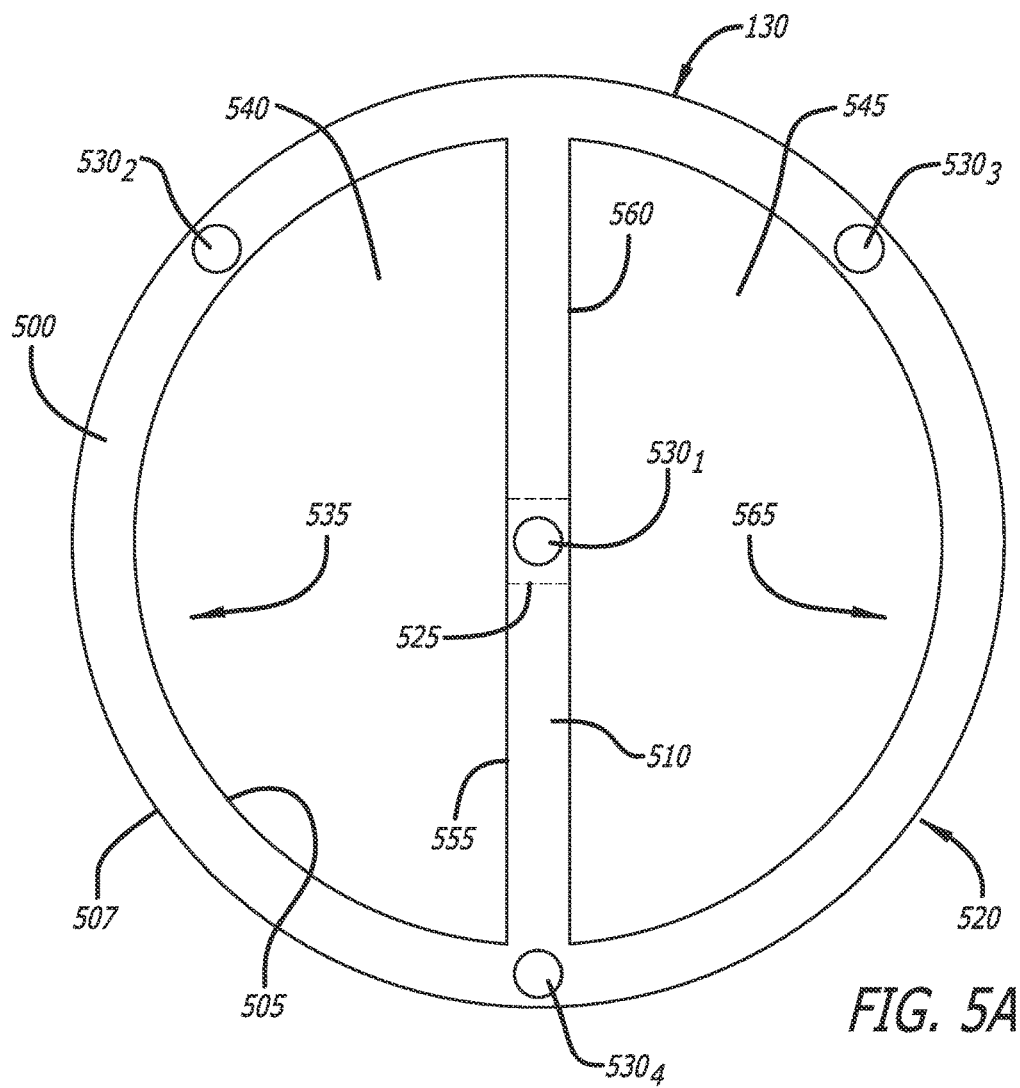
FIG. 5A is an elevation view of a first illustrative embodiment of a catheter including integrated tubing, a diametrically disposed septum, and micro-lumens formed within the tubing and septum in accordance with some embodiments.

Referring to FIG. 5A, an elevation view of a first illustrative embodiment of a catheter including integrated tubing, a diametrically disposed septum, and micro-lumens formed within the tubing and septum is shown in accordance with some embodiments. Herein, the catheter 130 includes integrated tubing, the diametrically disposed septum 510, and the plurality of micro-lumens $530_1$-$530_4$ which, for this embodiment, are fabricated to reside within the wall 500 of the integrated tubing of the catheter 130 and within the septum 510. In particular, the septum 510 separates a single lumen, formed by the inner surface 505 of the wall 500 of the catheter 130, into multiple lumens, namely two lumens 540 and 545 as shown. Herein, the first lumen 540 is formed between a first arc-shaped portion 535 of the inner surface 505 of the wall 500 forming the catheter 130 and a first outer surface 555 of the septum 510 extending longitudinally within the catheter 130. The second lumen 545 is formed between a second arc-shaped portion 565 of the inner surface 505 of the wall 500 forming the catheter 130 and a second outer surfaces 560 of the septum 510.

According to one embodiment of the disclosure, the two lumens 540 and 545 have approximately the same volume. However, the septum 510 need not separate the tubing into two equal lumens. For example, instead of the septum 510 extending vertically (12 o'clock to 6 o'clock) from a front-facing, cross-sectional perspective of the tubing, the septum 510 could extend horizontally (3 o'clock to 9 o'clock), diagonally (1 o'clock to 7 o'clock; 10 o'clock to 4 o'clock) or angularly (2 o'clock to 10 o'clock). In the later configuration, each of the lumens 540 and 545 of the catheter 130 would have a different volume.

With respect to the plurality of micro-lumens $530_1$-$530_4$, the first micro-lumen $530_1$ is fabricated within the septum 510 at or near the cross-sectional center 525 of the integrated tubing. For this embodiment, three micro-lumens $530_2$-$530_4$ are fabricated to reside within the wall 500 of the catheter 130. In particular, a second micro-lumen $530_2$ is fabricated within the wall 500 of the catheter 130, namely between the inner surface 505 and outer surface 507 of the first arc-shaped portion 535 of the wall 500. Similarly, the third micro-lumen $530_3$ is also fabricated within the wall 500 of the catheter 130, namely between the inner and outer surfaces 505/507 of the second arc-shaped portion 555 of the wall 500. The fourth micro-lumen $530_4$ is also fabricated within the inner and outer surfaces 505/507 of the wall 500 that are aligned with the septum 510.

According to one embodiment of the disclosure, as shown in FIG. 5A, the micro-lumens $530_2$-$530_4$ are positioned in accordance with a "top-left" (10 o'clock), "top-right" (2 o'clock) and "bottom" (6 o'clock) layout from a front-facing, cross-sectional perspective. Of course, the micro-lumens $530_2$-$530_4$ may be positioned differently, provided that the micro-lumens $530_2$-$530_4$ are spatially separated along the circumference 520 of the catheter 130 to ensure a more robust collection of reflected light signals from the outer core fibers $570_2$-$570_4$ when installed. For example, two or more of micro-lumens (e.g., micro-lumens $530_2$ and $530_4$) may be positioned at different quadrants along the circumference 520 of the catheter wall 500.

Figure 5B:
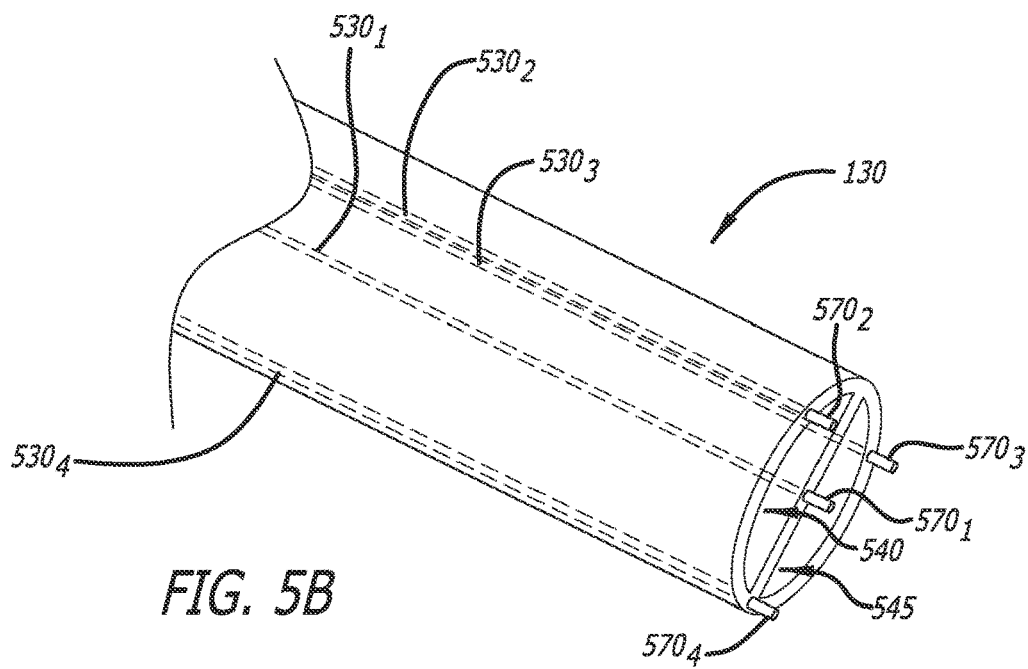
FIG. 5B is a perspective view of the first illustrative embodiment of the catheter of FIG. 5A including core fibers installed within the micro-lumens in accordance with some embodiments.

Referring to FIG. 5B, a perspective view of the first illustrative embodiment of the catheter of FIG. 5A including core fibers installed within the micro-lumens is shown in accordance with some embodiments. According to one embodiment of the disclosure, the second plurality of micro-lumens $530_2$-$530_4$ are sized to retain corresponding outer core fibers $570_2$-$570_4$, where the diameter of each of the second plurality of micro-lumens $530_2$-$530_4$ may be sized just larger than the diameters of the outer core fibers $570_2$-$570_4$. The size differences between a diameter of a single core fiber and a diameter of any of the micro-lumen $530_1$-$530_4$ may range between 0.001 micrometers (μm) and 1000 μm, for example. As a result, the cross-sectional areas of the outer core fibers $570_2$-$570_4$ would be less than the cross-sectional areas of the corresponding micro-lumens $530_2$-$530_4$. A "larger" micro-lumen (e.g., micro-lumen $530_2$) may better isolate external strain being applied to the outer core fiber $570_2$ from strain directly applied to the catheter 130 itself. Similarly, the first micro-lumen $530_1$ may be sized to retain the center core fiber $570_1$, where the diameter of the first micro-lumen $530_1$ may be sized just larger than the diameter of the center core fiber $570_1$.

As an alternative embodiment of the disclosure, one or more of the micro-lumens $530_1$-$530_4$ may be sized with a diameter that exceeds the diameter of the corresponding one or more core fibers $570_1$-$570_4$. However, at least one of the micro-lumens $530_1$-$530_4$ is sized to fixedly retain their corresponding core fiber (e.g., core fiber retained with no spacing between its lateral surface and the interior wall surface of its corresponding micro-lumen). As yet another alternative embodiment of the disclosure, all the micro-lumens $530_1$-$530_4$ are sized with a diameter to fixedly retain the core fibers $570_1$-$570_4$.

Figure 6A:
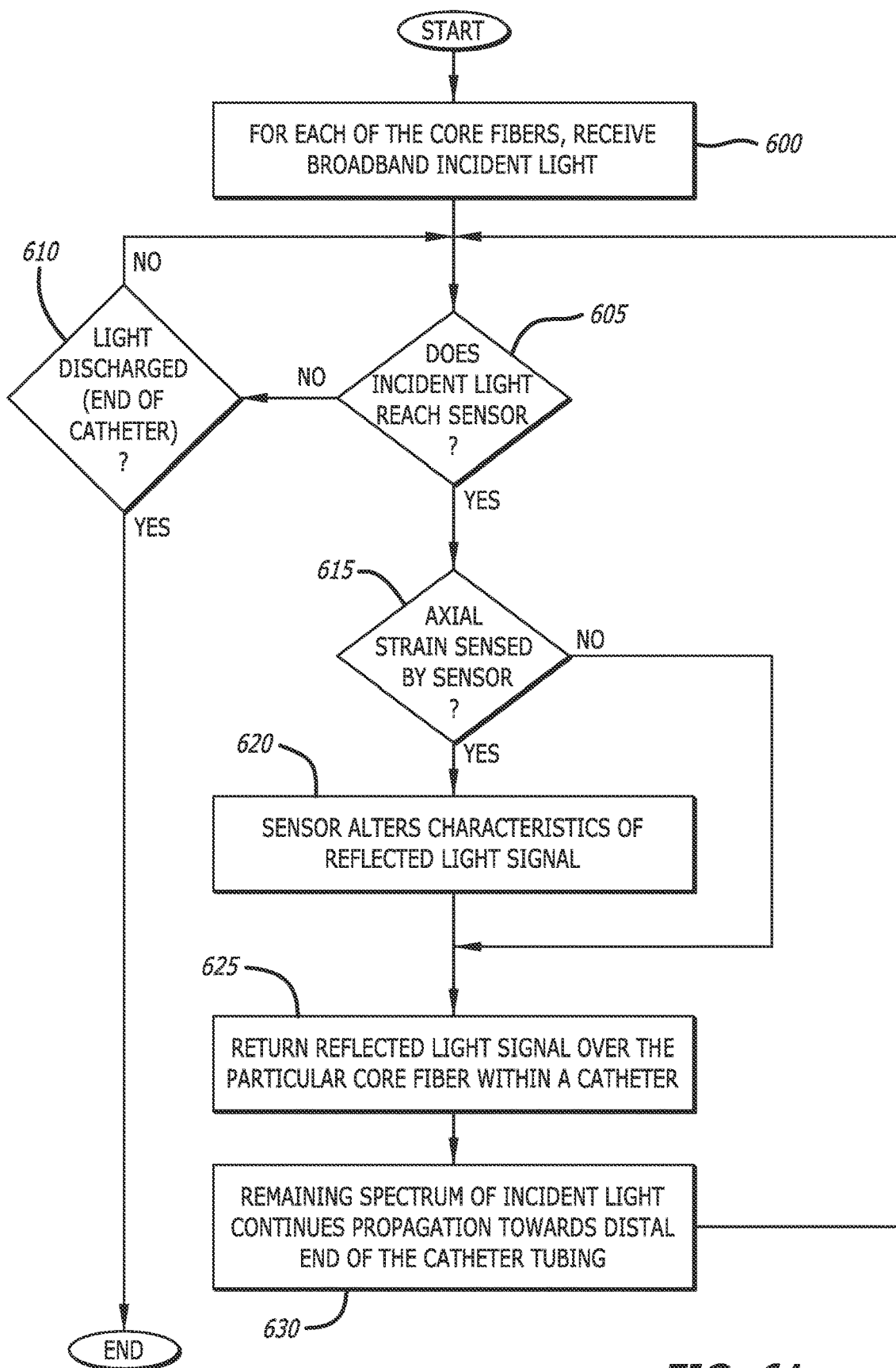
FIGS. 6A-6B are flowcharts of the methods of operations conducted by the medical instrument monitoring system of FIGS. 1A-1B to achieve optic 3D shape sensing in accordance with some embodiments.
Figure 6B:
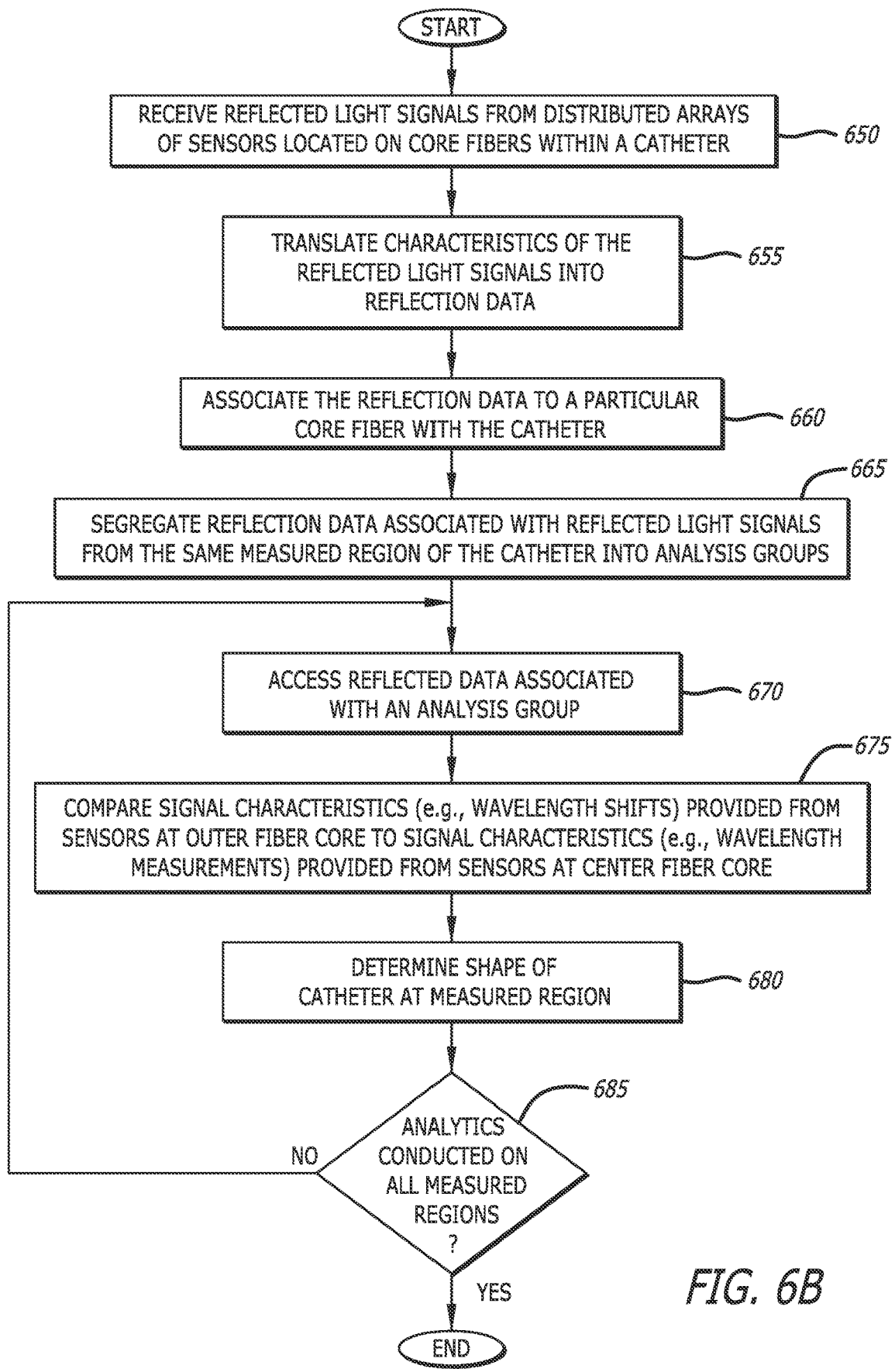

Referring to FIGS. 6A-6B, flowcharts of methods of operations conducted by the medical instrument monitoring system of FIGS. 1A-1B to achieve optic 3D shape sensing are shown in accordance with some embodiments. Herein, the catheter includes at least one septum spanning across a diameter of the tubing wall and continuing longitudinally to subdivide the tubing wall. The medial portion of the septum is fabricated with a first micro-lumen, where the first micro-lumen is coaxial with the central axis of the catheter tubing. The first micro-lumen is configured to retain a center core fiber. Two or more micro-lumen, other than the first micro-lumen, are positioned at different locations circumferentially spaced along the wall of the catheter tubing. For example, two or more of the second plurality of micro-lumens may be positioned at different quadrants along the circumference of the catheter wall.

Furthermore, each core fiber includes a plurality of sensors spatially distributed along its length between at least the proximal and distal ends of the catheter tubing. This array of sensors is distributed to position sensors at different regions of the core fiber to enable distributed measurements of strain throughout the entire length or a selected portion of the catheter tubing. These distributed measurements may be conveyed through reflected light of different spectral widths (e.g., specific wavelength or specific wavelength ranges) that undergoes certain wavelength shifts based on the type and degree of strain.

According to one embodiment of the disclosure, as shown in FIG. 6A, for each core fiber, broadband incident light is supplied to propagate through a particular core fiber (block 600). Unless discharged, upon the incident light reaching a sensor of a distributed array of sensors measuring strain on a particular core fiber, light of a prescribed spectral width associated with the first sensor is to be reflected back to an optical receiver within a console (blocks 605-610). Herein, the sensor alters characteristics of the reflected light signal to identify the type and degree of strain on the particular core fiber as measured by the first sensor (blocks 615-620). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the catheter tubing (blocks 625-630). The remaining spectrum of the incident light may encounter other sensors of the distributed array of sensors, where each of these sensors would operate as set forth in blocks 605-630 until the last sensor of the distributed array of sensors returns the reflected light signal associated with its assigned spectral width and the remaining spectrum is discharged as illumination.

Referring now to FIG. 6B, during operation, multiple reflected light signals are returned to the console from each of the plurality of core fibers residing within the corresponding plurality of micro-lumens formed within a catheter, such as the catheter of FIG. 1B. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 650-655). The reflection data classification logic is configured to identify which core fibers pertain to which reflection data and segregate reflection data provided from reflected light signals pertaining to a particular measurement region (or similar spectral width) into analysis groups (block 660-665).

Each analysis group of reflection data is provided to shape sensing logic for analytics (block 670). Herein, the shape sensing logic compares wavelength shifts at each outer core fiber with the wavelength shift at the center core fiber positioned along central axis and operating as a neutral axis of bending (block 675). From these analytics, on all analytic groups (e.g., reflected light signals from sensors in all or most of the core fibers), the shape sensing logic may determine the shape the core fibers have taken in three-dimensional space, from which the shape sensing logic can determine the current physical state of the catheter in three-dimension space (blocks 680-685).

Figure 7:
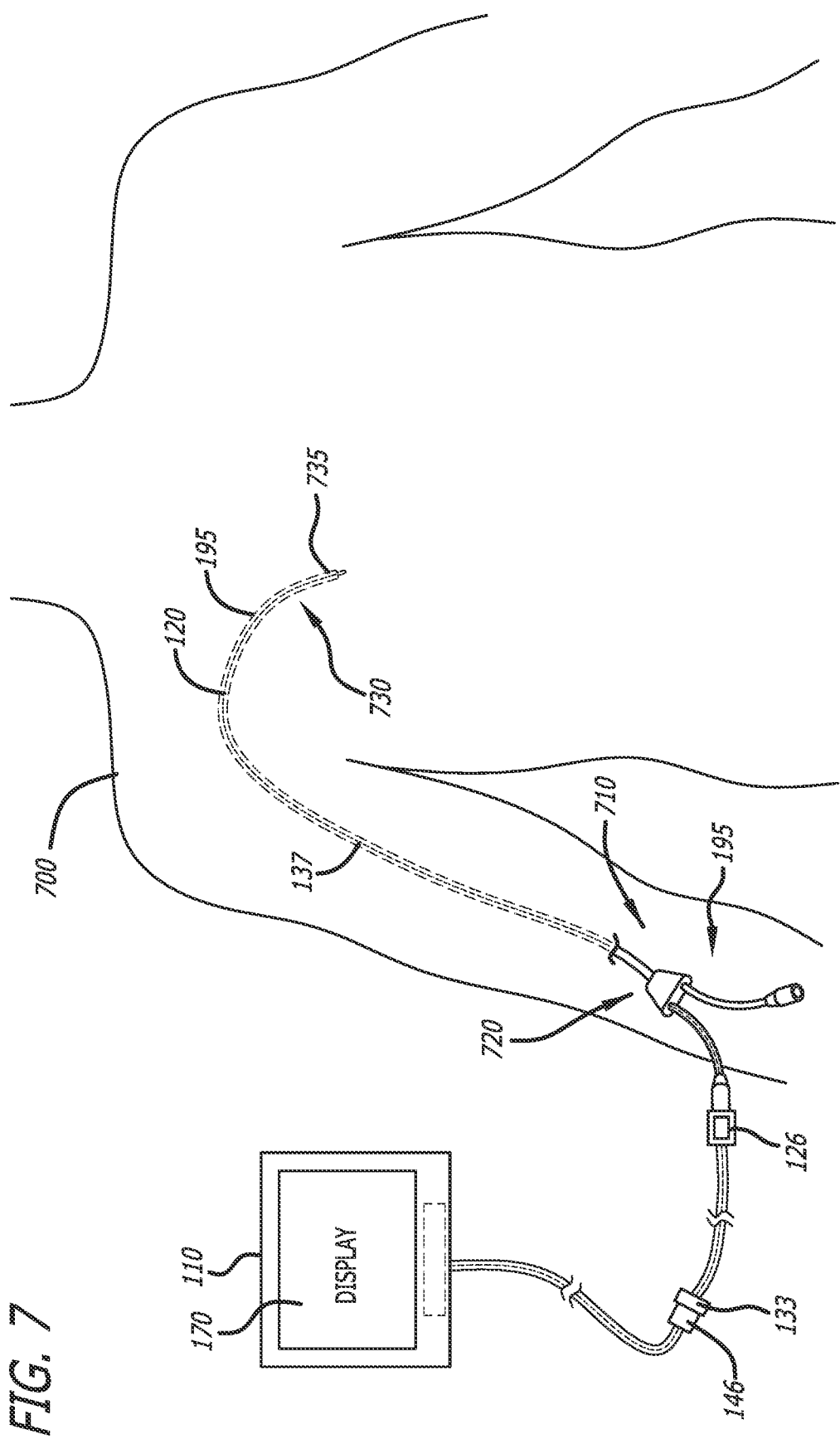
FIG. 7 is an exemplary embodiment of the medical instrument monitoring system of FIG. 1A during operation and insertion of the catheter into a patient in accordance with some embodiments.

Referring to FIG. 7, an exemplary embodiment of the medical instrument monitoring system of FIG. 1A during operation and insertion of the catheter into a patient are shown in accordance with some embodiments. Herein, the catheter 195 generally includes integrated tubing with a proximal portion 720 that generally remains exterior to the patient 700 and a distal portion 730 that generally resides within the patient vasculature after placement is complete, where the catheter 195 enters the vasculature at insertion site 710. The stylet 120 may be advanced through the catheter 195 to a desired position within the patient vasculature such that a distal end (or tip) 735 of the stylet 120 (and hence a distal end of the catheter 195) is proximate the patient's heart, such as in the lower one-third (⅓) portion of the Superior Vena Cava ("SVC") for example. For this embodiment, various instruments may be placed at the distal end 735 of the stylet 120 and/or the catheter 195 to measure pressure of blood in a certain heart chamber and in the blood vessels, view an interior of blood vessels, or the like.

The console connector 133 enables the stylet 120 to be operably connected to the console 110 via the interconnect 145 (FIG. 1A). Herein, the connector 146 is configured to engage (mate) with the console connector 133 to allow for the propagation of light between the console 110 and the stylet assembly 119 (particularly the stylet 120) as well as the propagation of electrical signals from the stylet 120 to the console 110

During advancement of the stylet 120, the distal tip 735 typically fluctuates due to, among other factors, blood flow and blood pressure within the blood vessel. These fluctuations may be movements by a distal portion of the stylet 120 in any direction. Typically, the movements are relatively minor compared to the overall advancement of the stylet 120 (and the catheter 195); however, such movements are detectable by the sensors of the core fibers integrated into the stylet 120.

The fluctuations may vary based on the blood vessel in which the stylet 120 (and catheter 195) is advancing due to one or more of the physical properties of the blood vessel, the location of the blood vessel (and its proximity to the patient's heart), and any defects affecting the blood vessel (e.g., vessel constriction, vasospasm, occlusion, etc.). As will be discussed in further detail below, the volume of the blood vessel may affect the fluctuations (e.g., a larger diameter may provide for greater fluctuation). Similarly, the turbulence of the blood flow generally affects the fluctuations (e.g., higher turbulence typically equates to greater fluctuation). Relatedly, the proximity of the distal tip 735 to the patient's heart may affect the fluctuations due to the turbulent blood flow emanating from the right atrium of the heart and flowing through the SVC. The blood pressure within the blood vessel may also affect tip fluctuations. Further, various defects may affect the fluctuations of the distal tip 735 and cause fluctuations that vary from those expected when the stylet 120 is advancing through a healthy blood vessel.

Figure 8:
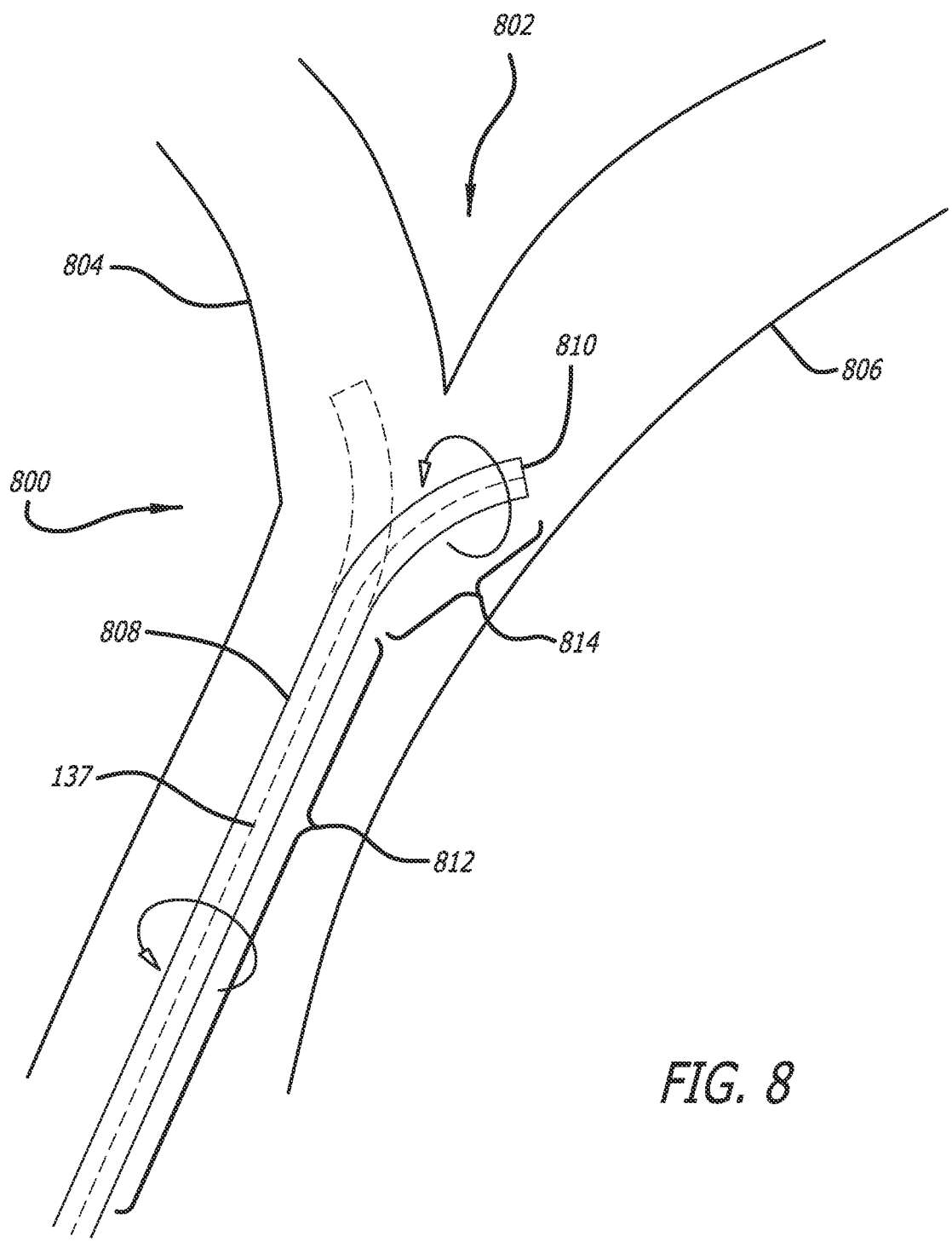
FIG. 8 is a cross sectional perspective view of a vessel within a vasculature having a medical instrument advancing therein where the medical instrument includes a predetermined shape and an optical fiber in accordance with some embodiments.

Referring to FIG. 8, a cross sectional perspective view of a vessel within a vasculature having a medical instrument advancing therein where the medical instrument includes a predetermined shape and supports optical signaling is shown in accordance with some embodiments. According to some embodiments, the medical instrument 808, e.g., a catheter, includes one or more optical fiber cores 137 ("optical fiber core") as discussed above and is illustrated as advancing through the vessel 800, and particularly at a junction 802 in which the vessel 800 includes branches 804-806. During advancement of the medical instrument 808, a clinician will desire to follow a particular branch 804 or 806 in order to continue advancement of the medical instrument 808 to a target location. Thus, the ability to steer the medical instrument 808 toward one of the branches 804 or 806 in integral in advancing the medical instrument 808, and particularly, the distal tip 810, to the target location, e.g., the lower one-third (⅓) portion of the SVC.

FIG. 8 provides one embodiment in which the medical instrument 808 is configured to be steered by a clinician in order to advance through a patient vasculature in a particular manner. In particular, the medical instrument 808 includes a proximal portion 812 and a curved distal portion 814 that has a predetermined, and often permanent, curvature relative to the proximal portion 812. As the medical instrument 808 is advanced through the patient vasculature, the clinician may be informed of a location of the distal tip 810 through at least optical signaling discussed above in which the fiber optical core 137 provides reflected light signals to the console 110, which processes the light signals to determine a positioning of at least the distal tip 810 within the patient vasculature. Such processing may involve determination of a physical state of the medical instrument 808 based on analytics of the wavelength shifts of the reflected light, as discussed above. Thus, with knowledge of the positioning of the distal tip 810 and of the human anatomy, the clinician may, for example, desire to advance the medical instrument 808 toward the branch 806 of the vessel 800. The medical instrument 808 is rotatable at the proximal end by the clinician, which results in a corresponding rotation of the curved distal portion 814, where rotation is illustrated by arrows in FIG. 8. As illustrated, the rotation of the medical instrument 808 by the clinician results in the curved distal portion 814 being directed into a particular direction, e.g., toward the branch 806, which enables the clinician to advance the medical instrument 808 toward the target location.

Figure 9A:
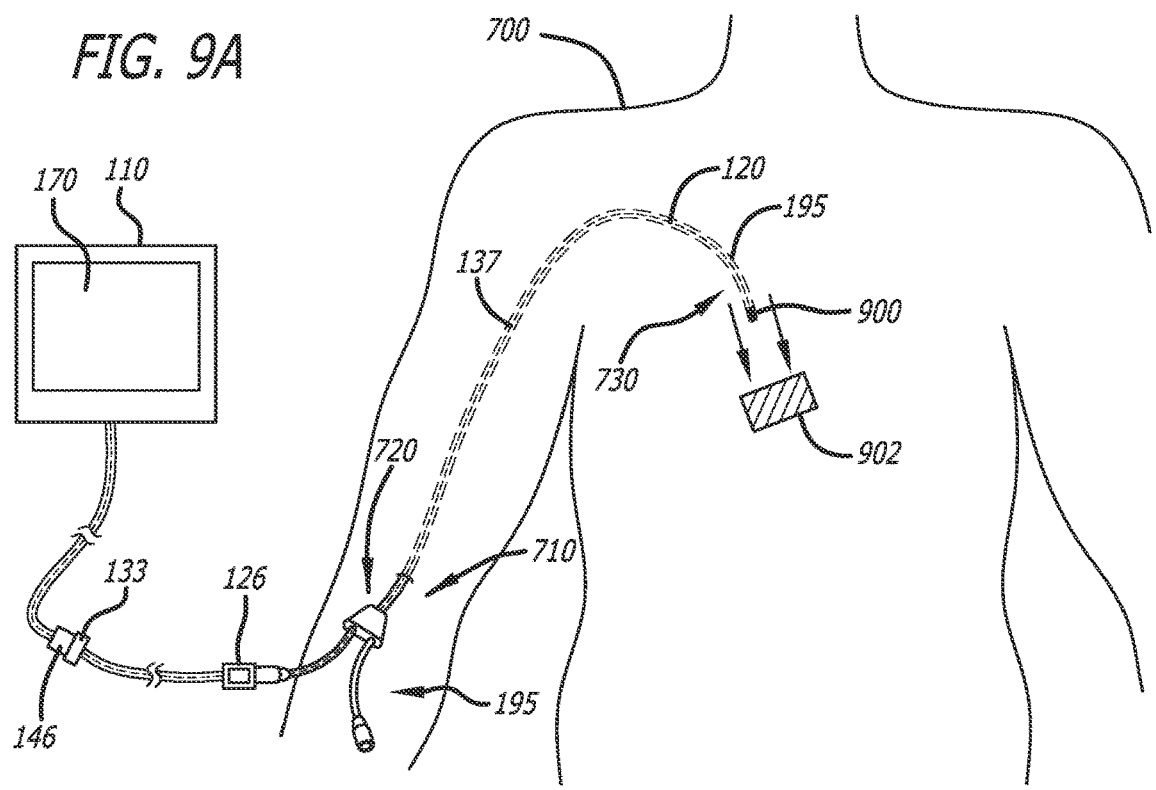
FIG. 9A is an exemplary embodiment of the medical instrument monitoring system of FIG. 1A during operation and advancement of a medical instrument within a patient vasculature in a first direction where the medical instrument includes a magnetic distal tip and an optical fiber in accordance with some embodiments.

Referring to FIG. 9A, an exemplary embodiment of the medical instrument monitoring system of FIG. 1A during operation and advancement of a medical instrument within a patient vasculature in a first direction where the medical instrument includes a magnetic distal tip, and an optical fiber is shown in accordance with some embodiments. The embodiment of FIGS. 9A-9B build off of the embodiment illustrated in FIG. 7. For example, as illustrated in each of FIGS. 7 and 9A-9B, the catheter 195 generally includes the integrated tubing of the catheter 195 with a proximal portion 720 that generally remains exterior to the patient 700 and a distal portion 730 that generally resides within the patient vasculature after placement is complete. The (integrated) catheter tubing of the catheter 195 may be advanced to a desired position within the patient vasculature such as a distal end (or tip) 735 of the catheter tubing of the catheter 195 is proximate the patient's heart, such as in the lower one-third (⅓) portion of the SVC, for example.

Figure 9B:
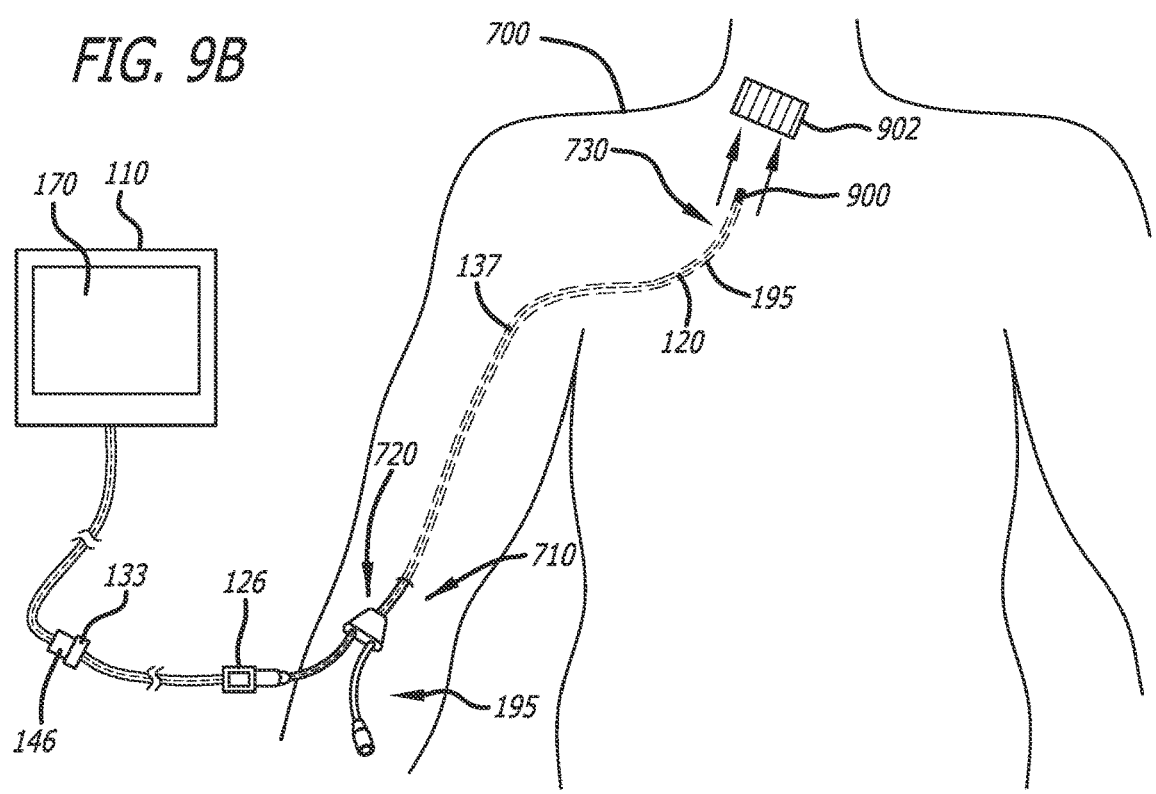
FIG. 9B is an exemplary embodiment of the medical instrument monitoring system of FIG. 1A during operation and advancement of the medical instrument of FIG. 9A within the patient vasculature in a second direction in accordance with some embodiments.

Various instruments may be placed at the distal end 735 of the stylet 120 (and/or the catheter 195 to measure pressure of blood in a certain heart chamber and in the blood vessels, view an interior of blood vessels, or the like. As illustrated in FIGS. 9A-9B, the catheter 195 includes a distal tip 900 that is that is magnetic, magnetized, metallic or ferrous and is steerable by an external magnetic device 902. In some embodiments, the external magnetic device 902 includes an electromagnet (or alternatively, a permanent magnet). As is understood in the art, the electromagnet 902 may include wire wound into a coil, that upon receipt of current, generates a magnetic field. In some embodiments, the wire of the electromagnet may be wound around a magnetic core (e.g., a ferromagnetic or ferrimagnetic material, which may include iron).

Depending on the configuration of the electromagnet 902 and the distal tip 900 (e.g., with respect to the direction of the flow of current through the electromagnet 902 and the polarity of the distal tip 900), the electromagnet 902 may either attract the distal tip 900 (as shown in FIGS. 9A-9B) or repel the distal tip 900 (not shown). Either embodiment, whether the electromagnet 902 attracts or repels the distal tip 900, may be utilized to steer the distal tip 900 of the catheter 195.

As illustrated in FIG. 9A, the distal tip 900 is being attracted to the external magnetic device 902, which is being controlled (e.g., moved, placed or positioned) by a clinician, not shown. Thus, the clinician may steer the catheter 195, e.g., to the SVC of the patient, by attracting the distal tip 900 such that during advancement of the catheter 195 through the patient vasculature, the distal tip 900 advances toward particular vessel pathways (e.g., branch 806 of FIG. 8) that lead to the target location, e.g., the SVC, based on the magnetic attraction between the distal tip 900 and the magnetic device 902.

Referring to now FIG. 9B, an exemplary embodiment of the medical instrument monitoring system of FIG. 1A during operation and advancement of the medical instrument of FIG. 9A within the patient vasculature in a second direction is shown in accordance with some embodiments. The illustration of FIG. 9B show the distal tip 900 being attracted to the external magnetic device 902, which is positioned near the patient's neck. Thus, in the illustration of FIG. 9B, the clinician may be steering the catheter 195 toward a carotid artery of the patient.

Figure 10A:
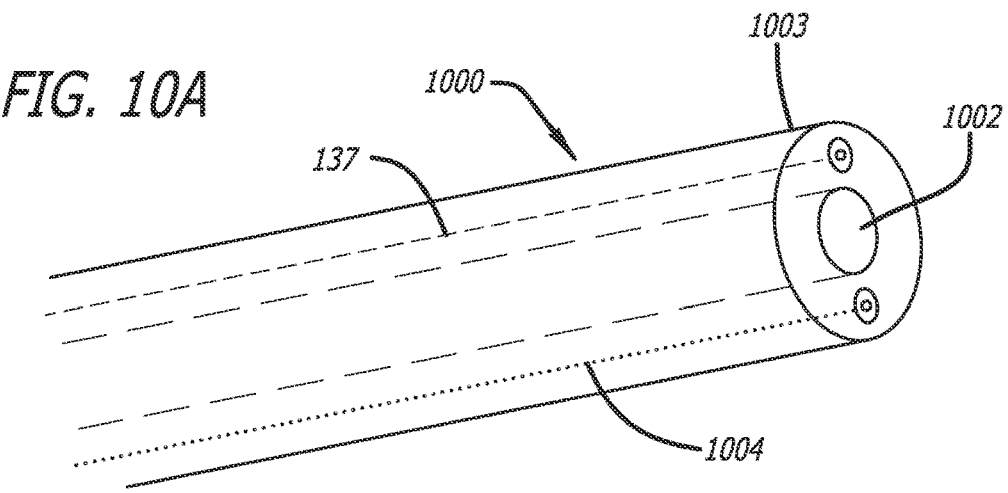
FIG. 10A is an exemplary embodiment of a medical instrument including an optical fiber and a tension cable in accordance with some embodiments.

Referring to now FIG. 10A, an exemplary embodiment of a medical instrument including an optical fiber and a tension cable is shown in accordance with some embodiments. The medical instrument 1000, e.g., a catheter, is shown to include a lumen 1002, a tension cable 1004 and a fiber optic core 137. In the particular embodiment shown, the tension cable 1004 is disposed opposite the fiber optic core 137 relative to the lumen 1002. As will be discussed in further detail with respect to at least FIGS. 10B-10F, the tension cable 1004 (or tension cables as in FIGS. 10C-10D and 10F) may be adjusted by a clinician, which causes movement of the distal tip 1003 of the catheter 1000. The movement of the distal tip 1003 results in formation of a curvature at a distal portion of the catheter 1000. Thus, by adjusting the tension cable 1004 to create a curvature of the distal portion of the catheter 1000, the clinician may steer the catheter 1000 during advancement as discussed above with respect to FIG. 8.

In particular, adjusting the tension cable 1004 may include pulling the tension cable 1004 in a proximal direction. The tension applied to tension cable 1004, is attached to the distal tip 1003 of the catheter 1000, results in the formation of a curvature at the distal end. Thus, the clinician can direct the distal tip 1003 toward a particular blood vessel, e.g., a junction where two or more blood vessel branches split into separate directions. In the embodiment of FIG. 10A in which there is only a single tension cable 1004, the clinician may rotate the catheter 1000 to direct the distal tip 1003 in the desired direction once a curvature has been formed at the distal end.

The catheter 1000 may be formed of material that is biased to return to a straight orientation (as opposed to a curved distal end) when there is no tension applied to the tension cable 1004. Thus, the clinician may release the tension applied to the tension cable 1004 causing the distal end of the catheter 1000 to return to a straightened orientation.

As an example, the clinician may determine a positioning of the catheter 1000 within the patient vasculature based on processing of reflected light received by the console 100 of FIGS. 1A-1B and based on the knowledge of the human anatomy, desire to advance the catheter 1000 through a particular pathway (e.g., series of one or more blood vessels). By adjusting the tension cable 1004 thereby creating a curvature at the distal portion of the catheter 1000, the clinician may steer the catheter 1000, which may include rotating the catheter 1000, as discussed above.

Figure 10B:
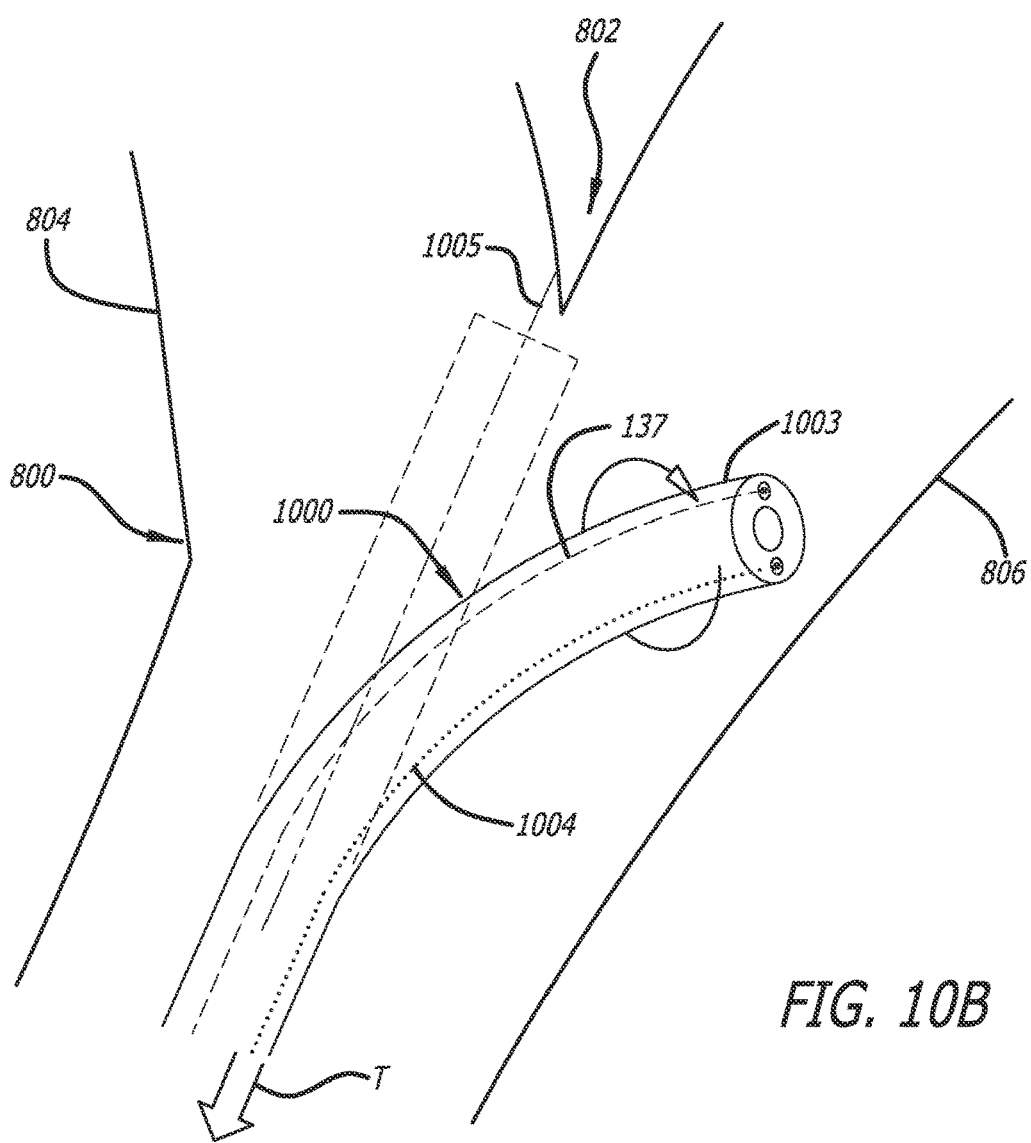
FIG. 10B is a cross sectional perspective view of a vessel within a vasculature having the medical instrument of FIG. 10A advancing therein in accordance with some embodiments.

Referring to FIG. 10B, a cross sectional perspective view of a vessel within a vasculature having the medical instrument of FIG. 10A advancing therein is shown in accordance with some embodiments. FIG. 10B provides an illustration of the example discussed above. In particular, tension T is applied to the tension cable 1004 in the proximal direction, causing the distal end of the catheter 1000 to deform from a first position being a straight orientation lacking a curvature relative to a center axis 1005 to a second position having a curvature. The first position is shown via dashed lines.

Thus, by applying the tension T, the clinician causes the deformation in the distal end of the catheter 1000 resulting in the curvature illustrated. The clinician may then rotate the catheter 1000 as needed in order to direct the distal tip 1003 in the desired direction, e.g., toward a desired blood vessel branch. As is understood by one skilled in the art, the amount of curvature is at least dependent in part on the amount of tension T applied to the tension cable 1004.

Referring to FIG. 10C, a second embodiment of a medical instrument including a plurality of optical fibers, a plurality of tension cables and a set of tension controls is shown in accordance with some embodiments. The medical instrument 1000 as illustrated in FIG. 10C includes a lumen 1002, a plurality of tension cables $1004_1$-$1004_i$ (i≥1, where i=2 in this embodiment) and a plurality of fiber optic cores $137_1$-$137_j$ (j≥1, where j=2 in this embodiment). Each of the tension cables $1004_1$-$1004_i$ and fiber optic cores $137_1$-$137_j$ may be integrated into the wall of the catheter 1000. The tension cables $1004_1$-$1004_2$ are disposed opposite each other relative to the lumen 1002 such that a clinician may apply tension in a proximal direction to either of tension cables $1004_1$-$1004_2$ in order to cause formation of a curvature in either direction such that less rotation of the catheter 1000 is needed in order to direct the distal tip 1003 toward a particular direction. As will be discussed in FIG. 10D, additional tension cables may be utilized to further reduce, or eliminate, the need to rotate the catheter 1000.

Additionally, the embodiment of FIG. 10C illustrates a control box 1010 coupled to the proximal end 1008 of the catheter 1000. The control box 1010 provides one embodiment in which a clinician may control (apply or release) tension of the tension cables $1004_1$-$1004_2$. For example, each of the tension controls $1012_1$-$1012_2$ correspond to one of the tension cables $1004_1$-$1004_2$ such that movement of a tension control $1012_1$-$1012_2$ results in application or release of tension to the corresponding tension cable $1004_1$-$1004_2$.

Referring to FIG. 10D, an exemplary embodiment of a third medical instrument including a plurality of optical fibers and a plurality of tension cables is shown in accordance with some embodiments. As noted above, the embodiment of FIG. 10D illustrates the catheter 1000 including a plurality of tension cables $1004_1$-$1004_i$ (i≥1, where i=4 in this embodiment) and a plurality of fiber optic cores $137_1$-$137_j$ (j≥1, where j=4 in this embodiment). The positioning of the tension cables $1004_1$-$1004_4$ may be positioned substantially equidistant from each other as measured along a perimeter of the cladding of the catheter 1000, such as at "top" (12 o'clock), "right" (3 o'clock) "bottom" (6 o'clock) and "left" (9 o'clock) locations as shown. Such positioning of the tension cables $1004_1$-$1004_4$ allows for a clinician to adjust the tension applied to one or more of the tension cables $1004_1$-$1004_4$ in order to direct the distal tip 1003 in any particular direction without the need to rotate the catheter 1000.

Figure 10E:
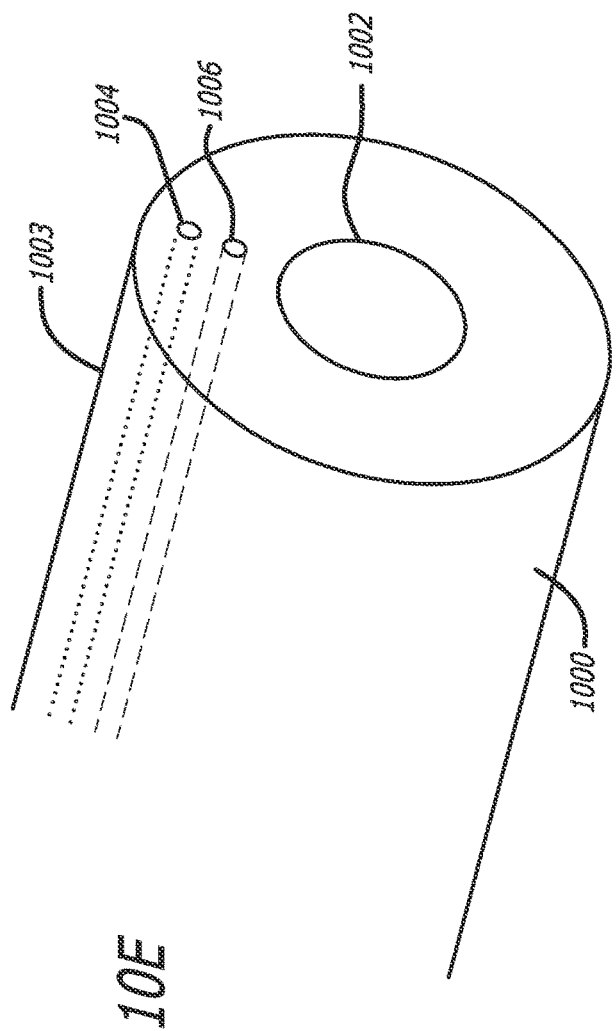
FIG. 10E is a fourth embodiment of a medical instrument including an optical fiber and a tension cable within a lumen in accordance with some embodiments.

Referring to FIG. 10E, a fourth embodiment of a medical instrument including an optical fiber and a tension cable within a lumen is shown in accordance with some embodiments. FIG. 10E provides an illustration of yet another embodiment in which a catheter 1000 includes a tension cable 1004 and a fiber optic core 137. Although illustrated with only one tension cable 1004 and one fiber optic core 137, some embodiments may include a plurality of one or more of each. As shown, the tension cable 1004 and the fiber optic core 137 are disposed within the cladding of the catheter 1000 immediately adjacent to each other.

Figure 10F:
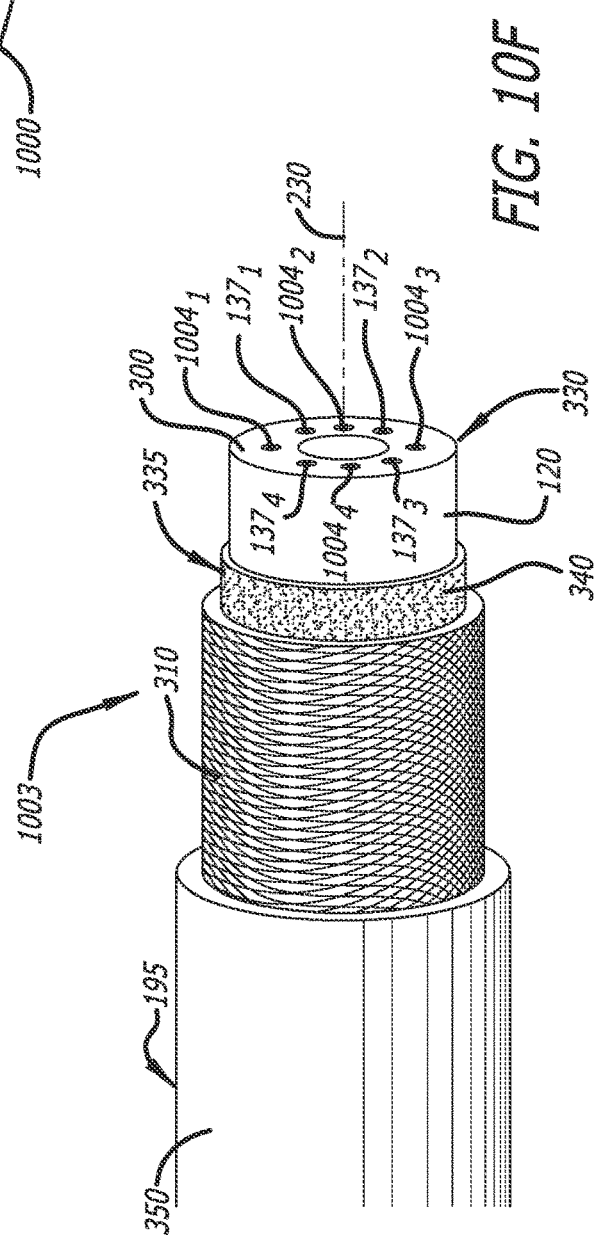
FIG. 10F is an exemplary embodiment of the stylet of FIG. 1A supporting an optical and electrical signaling and a plurality of tension cables in accordance with some embodiments.

Referring to FIG. 10F, an exemplary embodiment of the stylet of FIG. 1A supporting an optical and electrical signaling and a plurality of tension cables is shown in accordance with some embodiments. Herein, the embodiment illustrated in FIG. 10F is similar to the embodiment of the stylet 120 illustrated in FIG. 3A and features a centrally located multi-core optical fiber 137, which includes a cladding 300 and a plurality of core fibers $137_1$-$137_M$(M≥2; M=4) residing within a corresponding plurality of lumens $320_1$-$320_M$. As in FIG. 3A, the stylet 120 of FIG. 10F includes the multi-core optical fiber 137 having four (4) core fibers $137_1$-$137_4$, a greater number of core fibers $137_1$-$137_M$ (M≥4) may be deployed to provide a more detailed three-dimensional sensing of the physical state (e.g., shape, etc.) of the multi-core optical fiber 137 and the stylet 120 deploying the optical fiber 137, a greater number of core fibers $137_1$-$137_M$ (M≥4) may be deployed.

In addition to the components discussed above with respect to FIGS. 3A-3B, the stylet 120 of FIG. 10F includes a plurality of tension cables $1004_1$-$1004_4$, although an alternative number of tension cables may be utilized.

Referring to FIG. 11A, an illustration of an assembly including a catheter having a stylet advancing therethrough where the stylet supports optical signaling is shown in accordance with some embodiments. The catheter 195 includes a lumen 1103 through which the stylet 120 advances where the stylet 120 includes fiber optic core 137. In such an embodiment, the fiber optic core 137 receives incident light from a light source, e.g., in a console such as the console 100 of FIG. 1A, and reflects light back to the console 100 for processing. The reflected light signals including wavelength shifts caused by strain experienced by the fiber optic core 137. As discussed above, analysis of the strain enables a determination of the positioning of the fiber optic core 137 (and the catheter 195) within the patient vasculature.

As also discussed above, it is advantageous for a clinician to be able to steer the catheter 195 during advancement in the patient vasculature. One method for steering the catheter 195 is illustrated in FIGS. 11A-11B in which the positioning of the stylet 120 is adjustable within the catheter 195. In particular, the stylet 120 may be advanced or retracted relative to the catheter 195 (as indicated by the arrow 1100). In some embodiments, the stylet 120 has a flexural stiffness that is less than the flexural stiffness of a combination of the stylet 120 and the catheter 195. In one embodiment, the catheter 195 is configured with a greater flexural stiffness than the stylet 120. Regardless, advancement of the stylet 120 beyond the distal end 1101 of the catheter 195 results in a distal tip of the assembly being more flexible than when the stylet 120 is not advanced beyond the distal end 1101. In some embodiments, the catheter 195 may have a greater flexural stiffness than both the cladding (e.g., outer material) of the stylet 120 and the fiber optic core 137 located therein.

Flexural stiffness is understood as the product of the elastic modulus (E) of a material and the area moment of inertia (I) where the flexural stiffness (EI) has the SI units of Newtons (N)·meters² (m²) or N·m² (a function of Young's Modulus (GPa)). In the case of a solid circular cross-section, (I) is defined by the following Equation 1 where (d) is the diameter of the circular cross-section.

$$I = \frac{\pi}{64}d^4 \qquad \text{Equation 1}$$

Referring to now FIG. 11B, a cross sectional perspective view of a vessel within a vasculature having the assembly of FIG. 11A advancing within the vasculature based on a direction of blood flow is shown in accordance with some embodiments. As the stylet 120 is advanced beyond the distal end 1101 of the catheter 195 (indicated by arrow 1102), the flexible nature of the stylet 120 enables the assembly to be steered in a particular direction. In one embodiment, blood flow 1107 within the vasculature may steer the assembly by contacting the stylet 120 and causing a curvature within a distal portion 730 of the stylet 120. Thus, the distal portion 730, including the distal tip 735, are directed in the same direction as the blood flow 1107, as shown in FIG. 11B.

In an alternative embodiment, gravity may cause a similar effect as the blood flow 1107 shown in FIG. 11B. Specifically, based the positioning of the patient and knowledge of the positioning of distal tip 735 of the stylet 120 (e.g., from optic signaling), a clinician may advance the stylet 120 beyond the distal end 1101 of the catheter 195 in order to enable gravity to cause a curvature in the distal portion 730 of the stylet 120. As the assembly is advanced, the assembly will proceed along the vasculature pathway as directed by the distal portion 730 of the stylet 120.

Figure 11C:
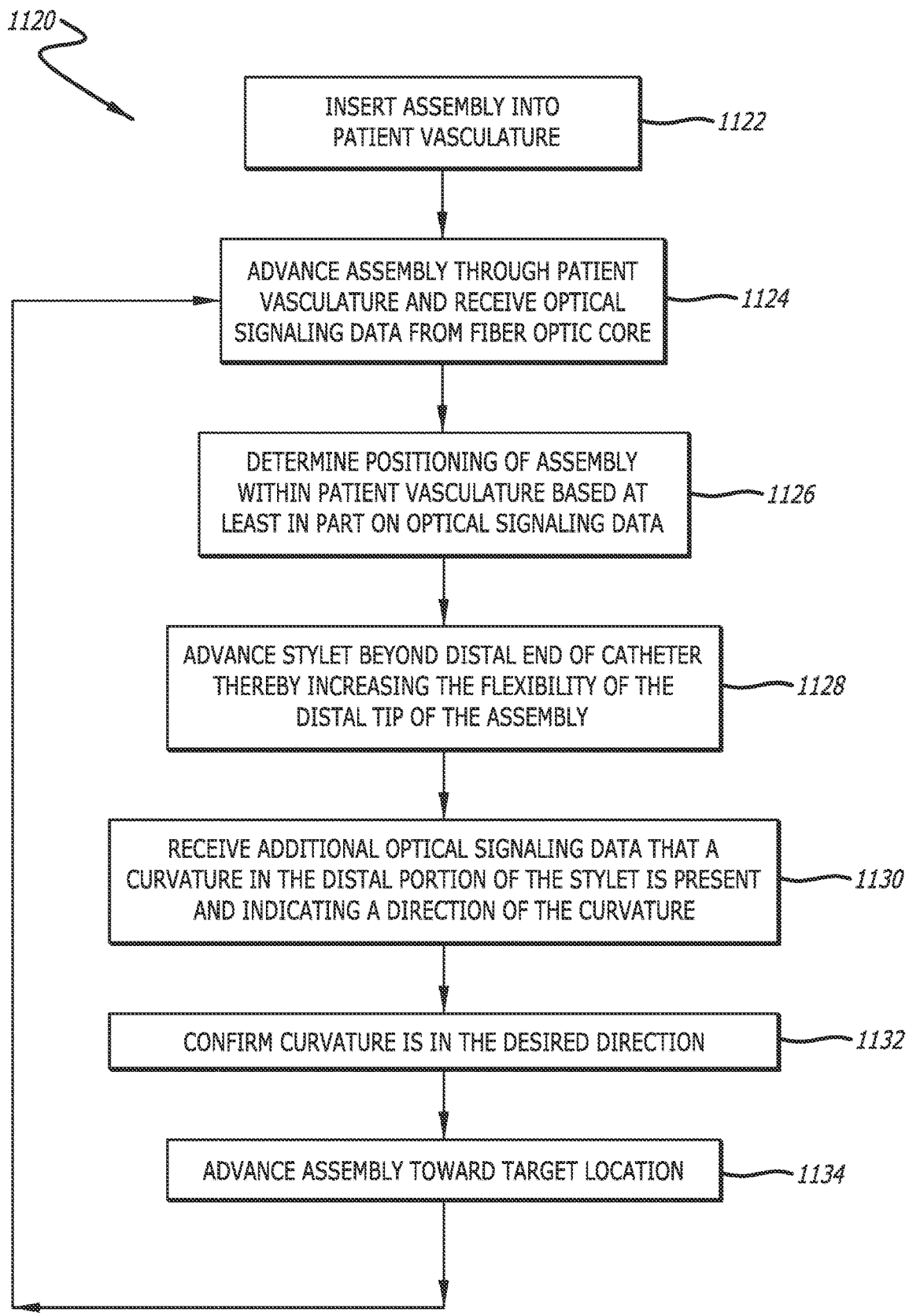
FIG. 11C is a flowchart of an exemplary methodology of steering the assembly of FIG. 11A in accordance with some embodiments.

Referring to FIG. 11C, a flowchart of an exemplary methodology of steering the assembly of FIG. 11A is shown in accordance with some embodiments. Each block illustrated in FIG. 11C represents an operation performed in the method 1120, which is initiated when the assembly of FIGS. 11A-11B, including the catheter 195 and the styler 120, is inserted into a patient vasculature (block 1122). According to one embodiment, the assembly is advanced through the patient vasculature and optical signaling data (e.g., reflect incident light) is received at a console, e.g., the console 100 of FIG. 1A (block 1124).

Following receipt of the optical signaling data, logic of the console 100 may determine a positioning of the assembly within the patient vasculature based at least in on part on the optical signaling data, as discussed above (block 1126). The stylet 120 may then be advanced beyond the distal end 1101 of the catheter 195, thereby increasing the flexibility of the distal tip of the assembly (block 1128). Specifically, in such embodiments, as the stylet 120 is more flexible than a combination of the stylet 120 and the catheter 195, advancing (or retracting) the stylet 120 beyond the distal end 1101 allows for adjustment of the stiffness of the distal tip of the assembly.

Following advancement of the stylet 120, the console 100 receive additional optical signaling data indicating that a curvature is a distal portion of the stylet is present, and further indicates a direction (or orientation) of the curvature relative to the patient vasculature (block 1195). Based on the additional optical signaling data, a clinician may confirm the curvature is in the desired direction, e.g., toward a vessel pathway leading to a target location, and advance the assembly accordingly (blocks 1132-1134). Alternatively, the logic of the console 100 may confirm the curvature is positioned in the correct direction in order to advance the assembly toward the target location (e.g., a vessel pathway may be predetermined and the logic of the console 100 may identify particular pathways via machine learning and confirm that the curvature of the distal tip of the assembly is directed appropriately so that advancement of the assembly will result in advancement along the identified pathway).

Referring to FIG. 11D, an illustration of a sheathed fiber optic core where the fiber optic core is configured to advance or retract relative to the sheath is shown in accordance with some embodiments. FIG. 11D illustrates an assembly including a sheath 1108 encasing the fiber optic core 137. In a similar manner as the embodiment discussed above with respect to FIGS. 11A-11C, the fiber optic core 137 may advance or retract relative to the sheath 1108 in order to create a more flexible distal tip of the assembly as compared to when the fiber optic core 137 is not extended beyond the distal tip of the sheath 1108. The flexible nature of the fiber optic core 137 as compared to a combination of the sheath 1108 and the fiber optic core 137 results in a distal tip of the assembly that may be deformed by either blood flow and/or gravity, as discussed above. In some embodiments, the fiber optic core 137 has a flexural stiffness that is less than the flexural stiffness of a combination of the fiber optic core 137 and the sheath 1108. In some embodiments, the sheath 1108 may have a greater flexural stiffness than the fiber optic core 137 located therein.

Referring to FIGS. 12A-12B, illustrations of a medical instrument supporting optical signaling and including an adjustment stiffening stylet are shown in accordance with some embodiments. FIGS. 12A-12B illustrate a medical instrument 1200, e.g., a catheter, guidewire, stylet, etc., that includes a cladding or outer casing 1203, which has integrated therein one or more optical fiber cores 137 ("optical fiber core") and a stiffening stylet 1202. It should be understood that the stiffening stylet 1202 has a greater flexural stiffness than both the cladding 1203 of the medical instrument 1200 and the fiber optic core 137 located therein.

The medical instrument 1200 further includes a stiffening stylet adjustment mechanism ("adjustment mechanism") 1204 that includes a proximal collar 1206, a distal collar 1210 and a set of hinged arms 1212. The proximal collar 1206 couples to the stiffening stylet 1202 via a connection point 1208. In some embodiments, the distal collar 1210 may be permanently coupled to a position on the catheter 1200, e.g., the distal collar 1210 would remain stationary during actuation of the adjustment mechanism. In some embodiments, the distal collar 1210 need not be present such that the distal component of the hinged arms 1212 couples directly to the medical instrument 1200.

Actuation of the adjustment mechanism 1204 may result in the movement of the proximal collar 1206 (e.g., back and forth, proximally and distally) with respect to the catheter 1200 and the distal collar 1210. As the stiffening stylet 1202 is coupled to the proximal collar 1206, movement thereof results in a corresponding movement of the stiffening stylet 1202. As shown in FIG. 12A, the adjustment mechanism 1204 is in a first configuration in which the proximal collar 1206 is in a first position (e.g., a distal position) and the stiffening stylet 1202 is extended toward the distal tip 1201 of the medical instrument 1200. In some embodiments, the adjustment mechanism 1204 is disposed external to the patient. Additionally, in various embodiments, the adjustment mechanism 1204 may be mechanically, manually or electromechanically actuated by the user.

FIG. 12B illustrates the adjustment mechanism 1204 in a second configuration in which the proximal collar 1206 is in a second position (e.g., a proximal position). As the proximal collar 1206 has moved from the distal position to the proximal position, the positioning of the stiffening stylet 1202 has also been adjusted such that it is no longer extended as far toward the distal tip 1201 of the medical instrument 1200 as shown in FIG. 12A. Thus, operation of the adjustment mechanism 1204 to move the proximal collar 1206 between the first and second positions results in adjusting the stiffness at the distal tip 1201 of the medical instrument 1200. In particular, the stiffening stylet 1202 has a greater level of stiffness than the cladding 1203 of the medical instrument 1200 and the fiber optic core 137. Thus, when the proximal collar 1206 is in the first (distal) position and the stiffening stylet 1202 is extended toward the distal tip 1201 as shown in FIG. 12A, the distal tip 1201 has a greater stiffness than when the proximal collar 1206 is in the second (proximal) position and the stiffening stylet 1202 is retracted as shown in FIG. 12B. The advantages of utilizing a medical instrument including a distal tip (or distal portion/end) having variable (or adjustable) stiffness are discussed above and apply equally to the embodiment of FIGS. 12A-12B.

FIGS. 13-20 illustrate first and second shape-sensing systems that can, in certain respects, resemble components of the medical instrument monitoring systems described in connection with FIGS. 1A-12B. It will be appreciated that all the illustrated embodiments may have analogous features. As such, relevant disclosure set forth above regarding similarly identified features thus may not be repeated hereafter. Moreover, specific features of the medical instrument monitoring system 100 and related components shown in FIGS. 1A-12B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the shape-sensing systems of FIGS. 13-20. Any suitable combination of the features, and variations of the same, described with respect to the medical instrument monitoring system 100 and components illustrated in FIGS. 1A-12B can be employed with the shape-sensing systems and components of FIGS. 13-20, and vice versa.

Figure 14:
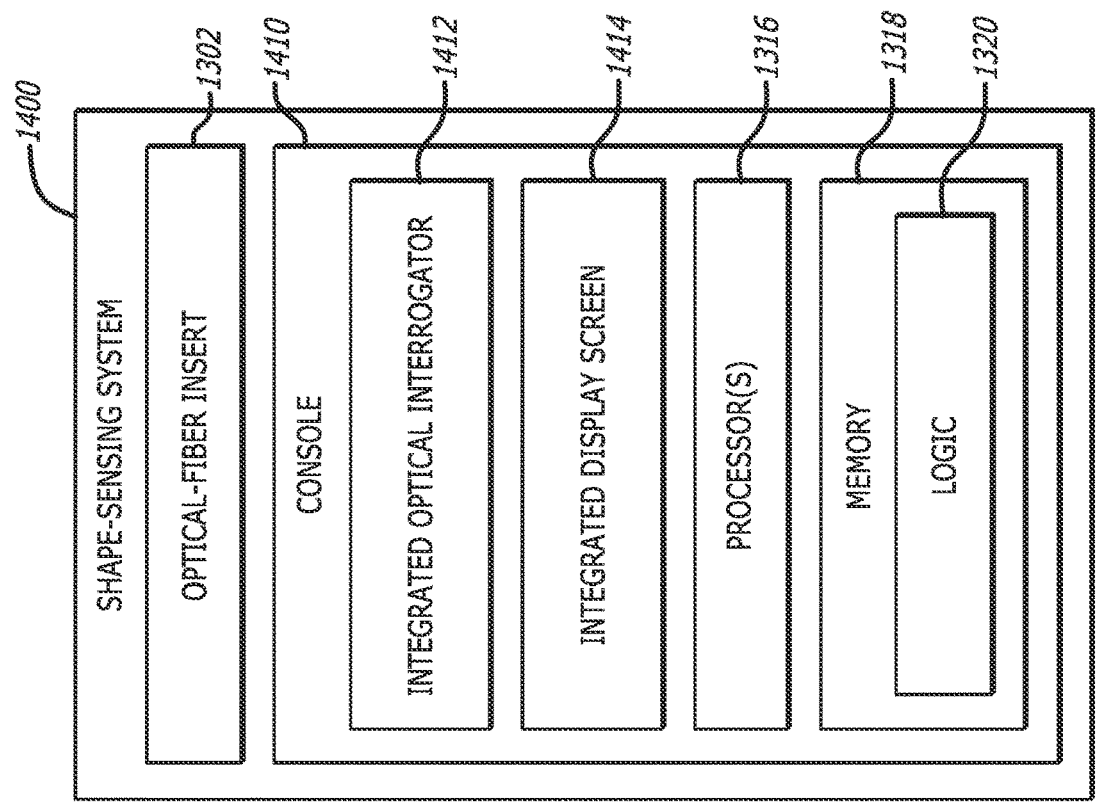
FIG. 14 is a block diagram of a second shape-sensing system including the optical-fiber insert in accordance with some embodiments.
Figure 13:
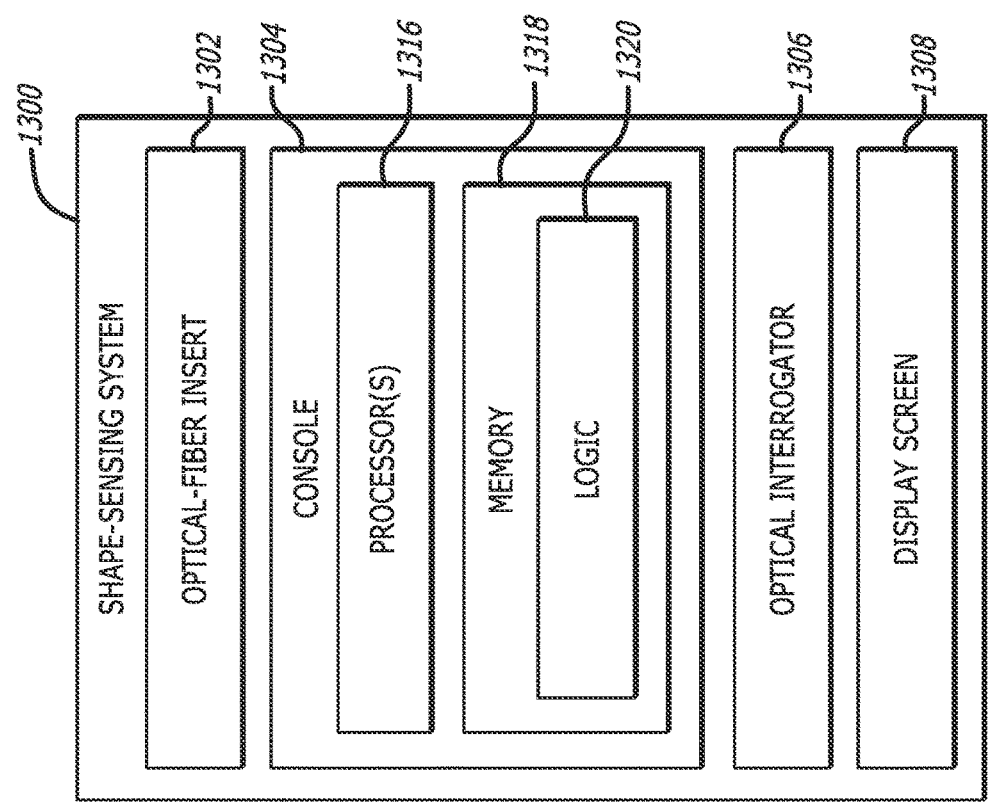
FIG. 13 is a block diagram of a first shape-sensing system including an optical-fiber insert in accordance with some embodiments.
Figure 15:
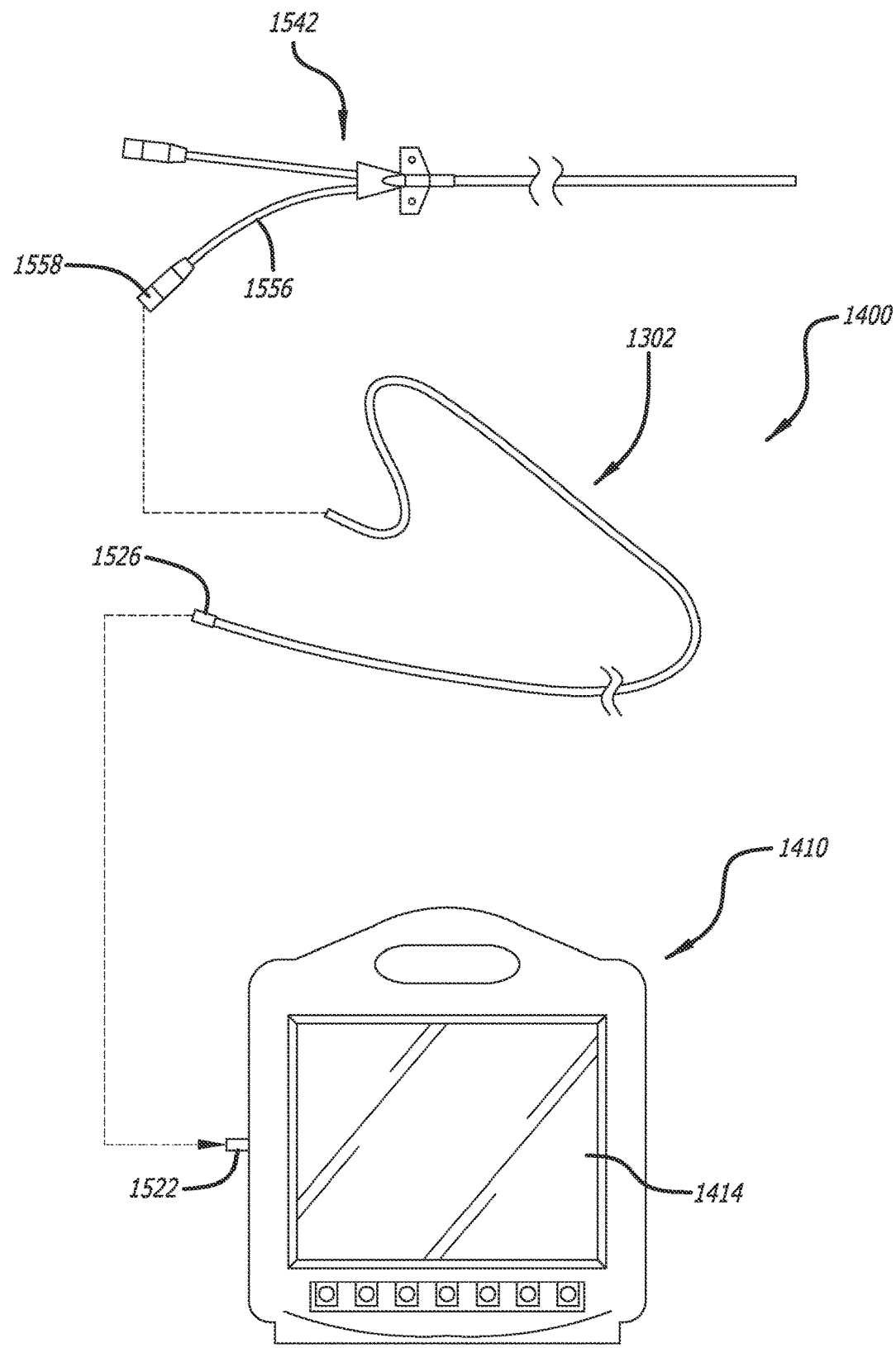
FIG. 15 illustrates the second shape-sensing system with a catheter in accordance with some embodiments.
Figure 20:
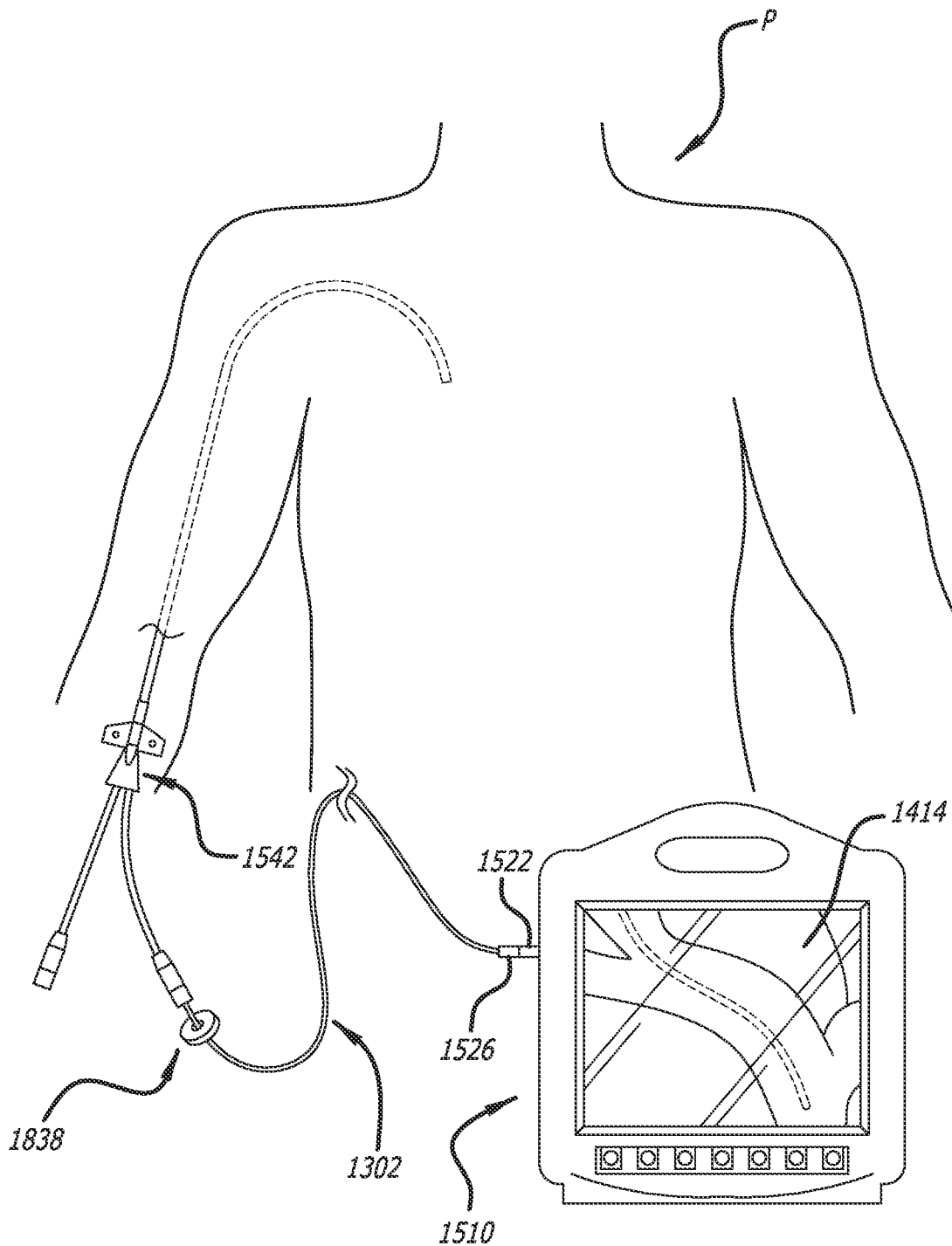
FIG. 20 illustrates the second shape-sensing system with the catheter in use on a patient during a medical procedure in accordance with some embodiments.

FIG. 13 is a block diagram of a first shape-sensing system 1300 including an optical-fiber insert 1302 in accordance with some embodiments. FIG. 14 is a block diagram of a second shape-sensing system 1400 including the optical-fiber insert 1302 in accordance with some embodiments. FIG. 15 illustrates the second shape-sensing system 1400 with the catheter 1542 in accordance with some embodiments. FIG. 20 illustrates the second shape-sensing system 1400 with the catheter 1542 in use on a patient P during a medical procedure in accordance with some embodiments.

As shown, the shape-sensing system 1300 includes the optical-fiber insert 1302, a console 1304, a stand-alone optical interrogator 1306, and a stand-alone display screen 1308, such as a stand-alone monitor. The shape-sensing system 1400 includes the optical-fiber insert 1302, a console 1410, an integrated optical interrogator 1412, and an integrated display screen 1414, wherein both the integrated optical interrogator 1412 and the integrated display screen 1414 are integrated into the console 1410. However, shape-sensing systems are not limited to the shape-sensing systems 1300 and 1400. For example, instead of the stand-alone optical interrogator 1306 or the stand-alone display screen 1308, the shape-sensing system 1300 can respectively include either the integrated optical interrogator 1412 or the integrated display screen 1414.

While the optical-fiber insert 1302 is part of the shape-sensing system 1300 or 1400, description for the optical-fiber insert 1302 as well as the optical-fiber insert holder 1838 of the system 1300 or 1400 is set forth in a separate section below.

Each console of the consoles 1304 and 1410 includes one or more processors 1316 and memory 1318 including logic 1320 such as optical signal-converter logic. The optical signal-converter logic is configured to convert FBG sensor-reflected optical signals from the optical-fiber insert 1302 into plottable data for displaying a graphical representation of the optical-fiber insert 1302 on the display screen 1308 or 1414 including a shape of the optical-fiber insert 1302 and a location of the optical-fiber insert 1302 within a patient such the patient P of FIG. 20. The optical signal-convertor logic can also be configured to convert the reflected optical signals from the optical-fiber insert 1302 into plottable data for a number of plots of the plottable data such as a plot of curvature vs. arc length, a plot of torsion vs. arc length, a plot of angle vs. arc length, a plot of position vs. time, or a plot of curvature vs. time. Such plots can also be displayed on the display screen 1308 or 1414 independent of or together with the graphical representation of the optical-fiber insert 1302 and the location of the optical-fiber insert 1302 within the patient P.

Each console of the consoles 1304 and 1410 also includes a connector 1522. The connector 1522 can be configured as a quick-connect connector complementary to the quick-connect connector of the optical-fiber insert 1302 set forth below for quickly connecting the optical-fiber insert 1302 to the console 1304 or 1410 or disconnecting the optical-fiber insert 1302 from the console 1304 or 1410. Advantageously, the console 1304 or 1410 can be configured to automatically instantiate one or more shape-sensing processes for shape-sensing with the optical-fiber insert 1302 when the optical-fiber insert 1302 is connected to the console 1304 or 1410. The one-or-more shape-sensing processes include sending input optical signals from the optical interrogator 1306 or 1412 to the optical-fiber insert 1302 and receiving FBG sensor-reflected optical signals by the optical interrogator 1306 or 1412 from the optical-fiber insert 1302.

Each console of the consoles 1304 and 1410 can also be configured for electrocardiography, conductance measurements, or impedance measurements with the optical-fiber insert 1302 when the optical-fiber insert 1302 is configured with electrical circuitry and componentry for the electrocardiography, the conductance measurements, or the impedance measurements. Indeed, the console 1304 or 1410 can be configured to automatically instantiate one or more electrical tip-location processes configured to locate a distal tip of the optical-fiber insert 1302 by way of the electrocardiography, the conductance measurements, or the impedance measurements if such electrical circuitry and componentry of the optical-fiber insert 1302 is detected by the console 1304 or 1410. Like the optical signal-converter logic, the logic 1320 can include electrical signal-converter logic configured to convert electrical signals from the optical-fiber insert 1302 into plottable data for displaying an electrocardiogram, a plot of conductance, or a plot of impedance on the display screen 1308 or 1414.

The optical interrogator 1302 or 1412 is configured to send input optical signals into the optical-fiber insert 1302 and receive the FBG sensor-reflected optical signals from the optical-fiber insert 1302.

Notably, medical devices such as those in FIGS. 19A-19E are not generally considered part of the shape-sensing system 1300 or 1400 because the foregoing medical devices are single-use medical devices. The shape-sensing system 1300 or 1400 and the optical-fiber insert 1302 thereof is preferably configured for multiple uses.

Optical-Fiber Inserts

Figure 16:
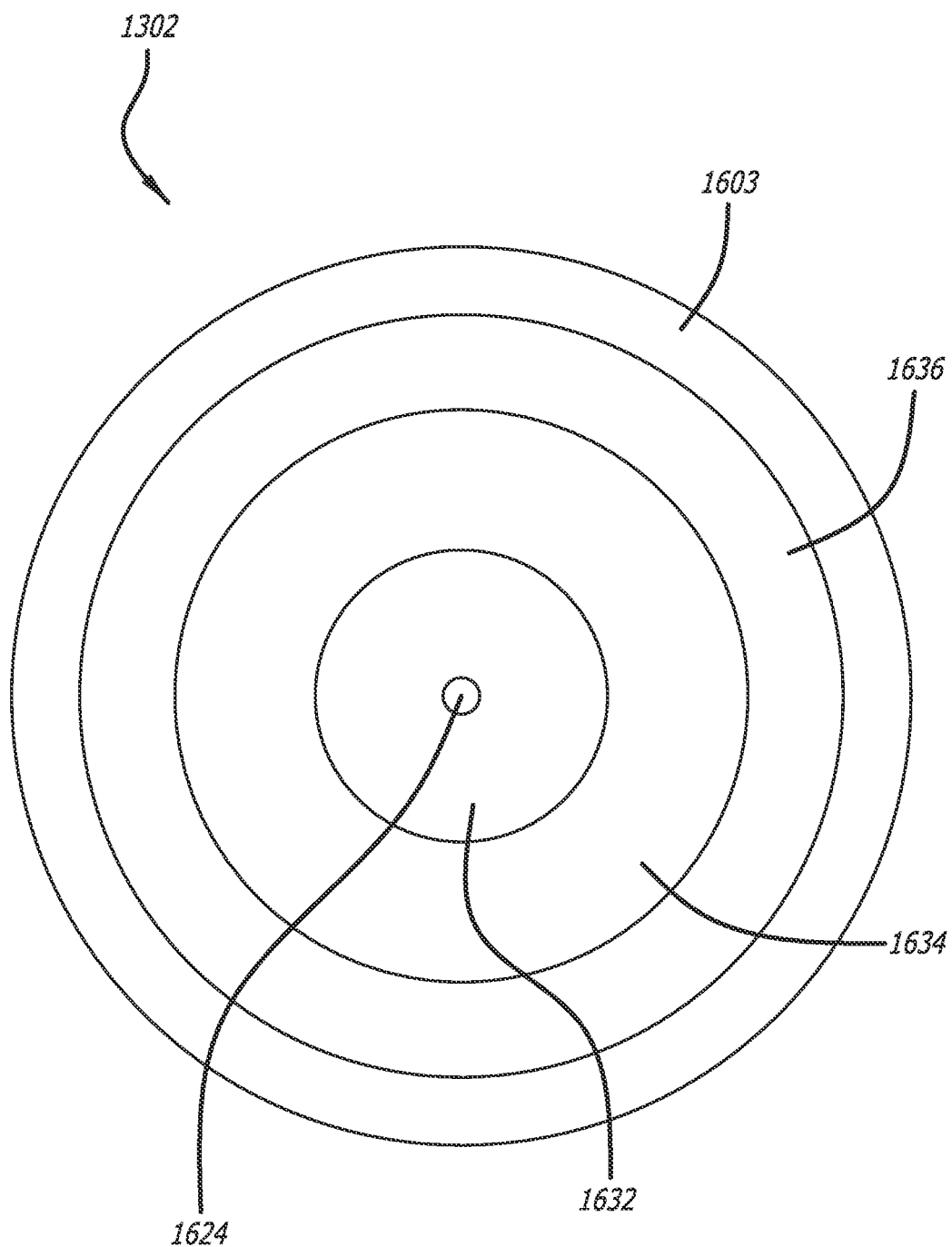
FIG. 16 illustrates a transverse cross-section of the optical-fiber insert in accordance with some embodiments.
Figure 17:
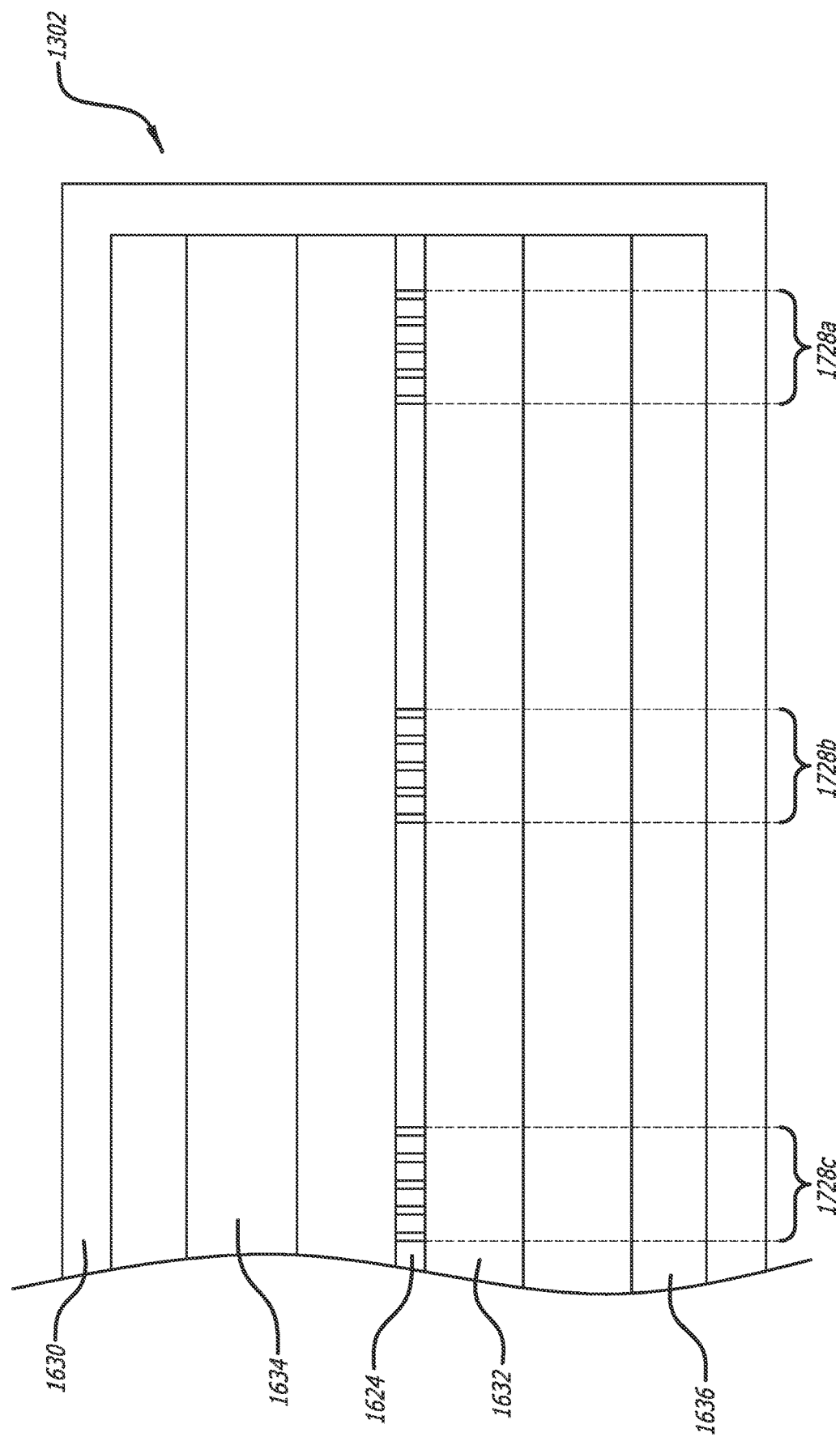
FIG. 17 illustrates a longitudinal cross-section of a distal portion of the optical-fiber insert in accordance with some embodiments.

FIGS. 15 and 20 illustrate the optical-fiber insert 1302 in the context of the shape-sensing system 1400 in accordance with some embodiments. FIG. 16 illustrates a transverse cross-section of the optical-fiber insert 1302 in accordance with some embodiments. FIG. 17 illustrates a longitudinal cross-section of a distal portion of the optical-fiber insert 1302 including a distal end in accordance with some embodiments.

As shown, the optical-fiber insert 1302 is an elongate medical device such as an optical-fiber stylet, an optical-fiber guidewire, or an optical-fiber obturator configured to load into a lumen of another medical device such as an intravascular medical device, for example, the catheter 1542. The optical-fiber insert 1302 includes one or more cores 1624, a number of functional layers around the one-or-more cores 1624, optional electrical circuitry and componentry, and a connector 1526 for connecting the optical-fiber insert 1302 to the console 1304 or 1410.

The one-or-more cores 1624 are of drawn plastic or glass having a number of FBG sensors 1628a, 1628b, 1628c, . . . , 1628n disposed along at least the distal portion of the optical-fiber insert 1302 configured for shape-sensing with the shape-sensing system 1300 or 1400. The FBG sensors 1628a, 1628b, 1628c, . . . , 1628n include periodic variations in refractive index of the one-or-more cores 1624 of the optical-fiber insert 1302, thereby forming wavelength-specific reflectors configured to reflect input optical signals sent into the optical-fiber insert 1302 by the optical interrogator 1306 or 1412 back to the optical interrogator 1306 or 1412 as FBG sensor-reflected optical signals. FIG. 17 illustrates, in particular, a last three FBG sensors 1628a, 1628b, and 1628c in the distal portion of the optical-fiber insert 1302, which FBG sensors 1628a, 1628b, and 1628c may be particularly useful in identifying distinctive changes in curvature of the optical-fiber insert 1302. This is because the last three FBG sensors 1628a, 1628b, and 1628c may directly experience a physical change in the curvature of the optical-fiber insert 1302 when the distal tip of the optical-fiber insert 1302 is advanced into a target anatomical location of a patient such as a superior vena cava ("SVC").

The number of functional layers surrounding the one-or-more cores 1624 include at least an outer jacket 1630, which can be made of a plastic. In addition, the number of functional layers can include a cladding 1632, a coating 1634, a layer of strengthening fibers 1636, or combination thereof between the one-or-more cores 1624 and the outer jacket 1630. For example, the number of functional layers can include the cladding 1632 over the one-or-more cores 1624, which can be made of a plastic or glass having a lower refractive index than that of the one-or-more cores 1624 to promote total internal reflection in the one-or-more cores 1624. Continuing with the example, the number of functional layers can include the coating 1634 over the cladding 1632, which can be made of a plastic (e.g., silicone) to protect light-reflecting layers (e.g., the one-or-more cores 1624, the cladding 1632, etc.) of the optical-fiber insert 1302. Further continuing with the example, the number of functional layers can include the layer of strengthening fibers 1636 over the coating 1634, which can be made of poly (p-phenylene terephthalamide) to further protect at least the light-reflecting layers of the optical-fiber insert 1302.

When present, the electrical circuitry and componentry of the optical-fiber insert 1302 is configured for the electrocardiography, the conductance measurements, or the impedance measurements set forth above with respect to the consoles 1304 and 1410.

The connector 1526 for connecting the optical-fiber insert 1302 to the console 1304 or 1410 can be configured as a quick-connect connector about a proximal end of the optical-fiber insert 1302. Such a quick-connect connector is configured for quickly connecting to or disconnecting from the complementary quick-connect connector of the console 1304 or 1410 set forth above.

The optical-fiber insert 1302 can be configured to be reusable. More specifically, in use, the optical-fiber insert 1302 may be inserted with a lumen of a first medical device, removed therefrom and subsequently inserted with a lumen of a second medical device. In use, the optical-fiber insert 1302 may be advanced along a vasculature of a first patient, re-sterilized thereafter, and subsequently advanced along a vasculature of a second patient.

The outer jacket 1630 and the connector 1526 can have sufficient physical and chemical integrity for sterilization (including re-sterilization between uses) by dry heat, moist heat optionally in combination with pressure (e.g., by an autoclave), a biocide (e.g., hydrogen peroxide, ethylene oxide, etc.) optionally in combination with pressure, radiation (e.g., ultraviolet radiation), or a combination thereof. Additionally, or alternatively, the optical-fiber insert 1302 can include a film or coating over the outer jacket 1630. Such a film or coating can be configured for removal after using the optical-fiber insert 1302 and subsequent reapplication or replenishment before using the optical-fiber insert 1302 again. Further additionally or alternatively, the optical-fiber insert 1302 can include a disposable cover configured to cover the optical-fiber insert 1302, wherein a new cover can be used on the optical-fiber insert 1302 for each new use of the optical-fiber insert 1302.

Figure 18:
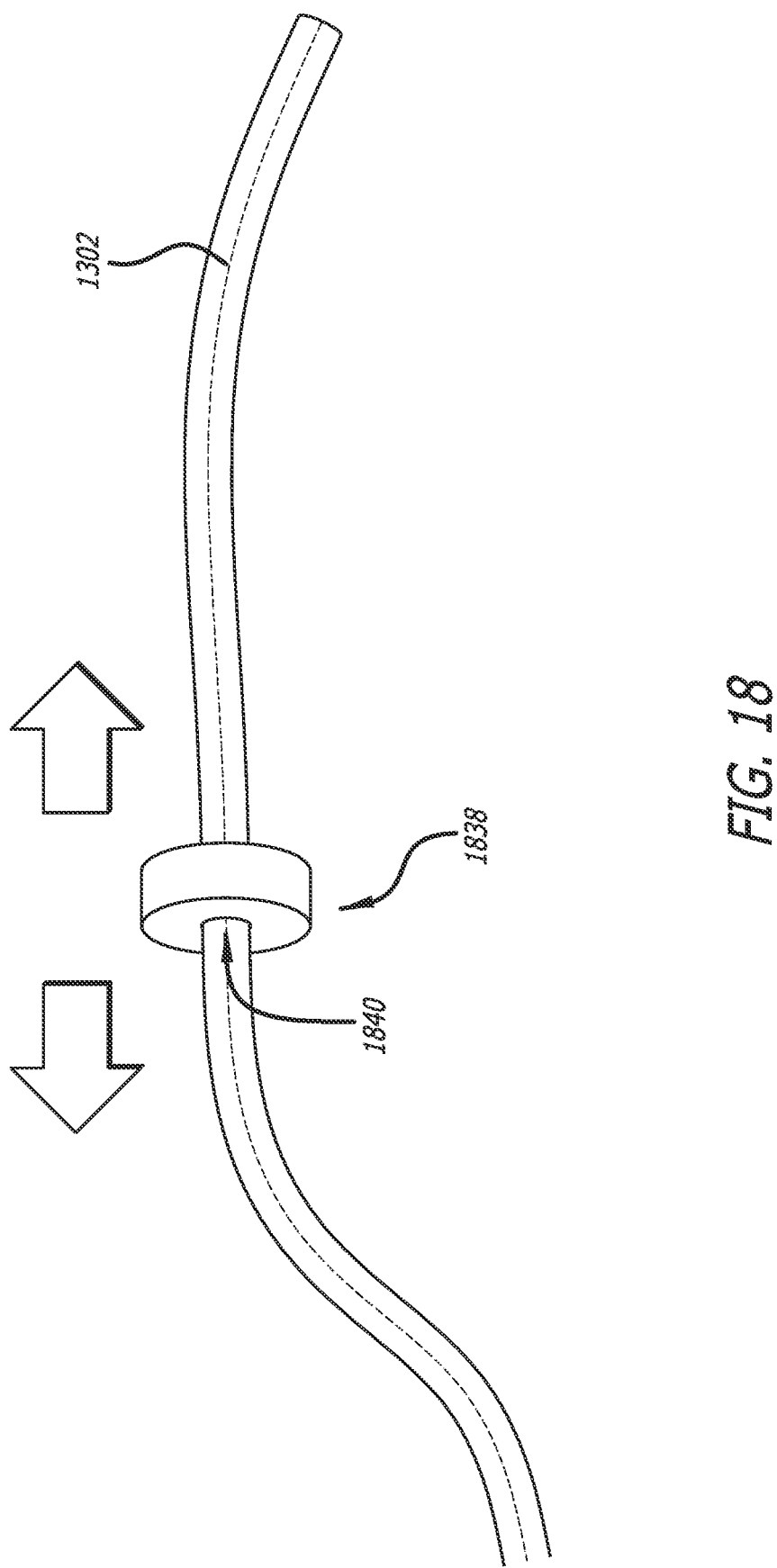
FIG. 18 illustrates an optical-fiber insert holder in accordance with some embodiments.

FIG. 18 illustrates an optical-fiber insert holder 1838 in accordance with some embodiments. As shown, the optical-fiber insert 1302 may further include the optical-fiber insert holder 1838. The optical-fiber insert holder 1838 is configured to accept the optical-fiber insert 1302 through a through hole 1840 of the optical-fiber insert holder 1838, which through hole 1840 is configured to hold the optical-fiber insert 1302 therein with friction and, thereby, prevent at least proximal movement of the optical-fiber insert 1302 while the optical-fiber insert 1302 is disposed in a medical device such as one of those in FIGS. 19A-19E. Indeed, the optical-fiber insert holder 1838 being too large to fit into a lumen of a medical device such as one of those in FIGS. 19A-19E effectively prevents the proximal movement of the optical-fiber insert 1302 while the optical-fiber insert 1302 is disposed in the medical device. However, the optical-fiber insert holder 1838 can be configured to couple to a Luer connector of the medical device or the like to prevent proximal movement of the optical-fiber insert 1302 as well.

Medical Devices

Figure 19A:
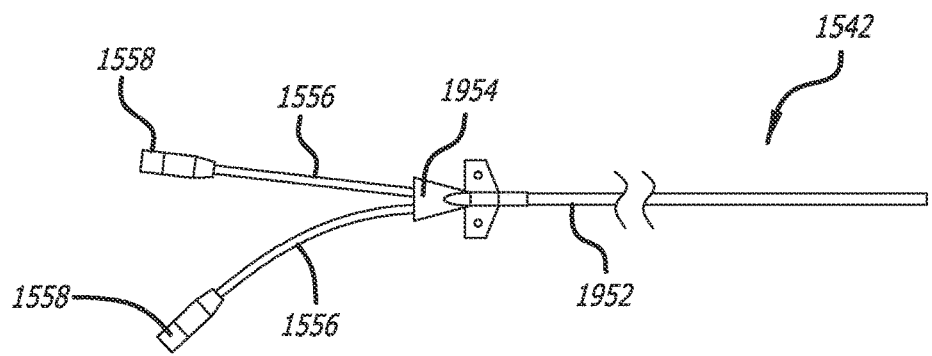
FIG. 19A illustrates a catheter into which the optical-fiber is configured to insert in accordance with some embodiments.
Figure 19B:
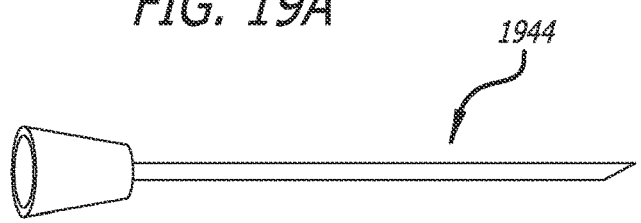
FIG. 19B illustrates a needle into which the optical-fiber is configured to insert in accordance with some embodiments.
Figure 19C:
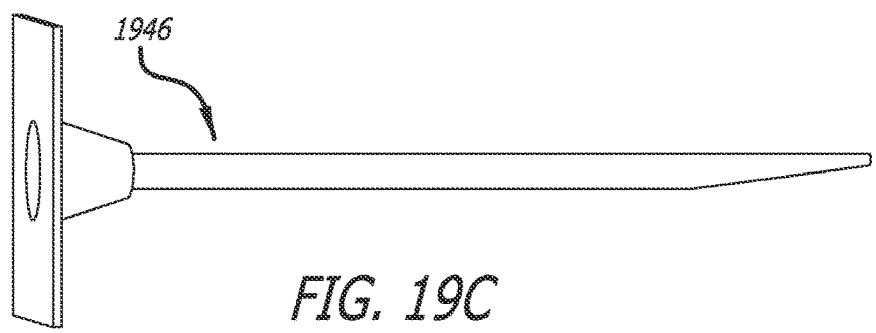
FIG. 19C illustrates an introducer into which the optical-fiber is configured to insert in accordance with some embodiments.
Figure 19D:
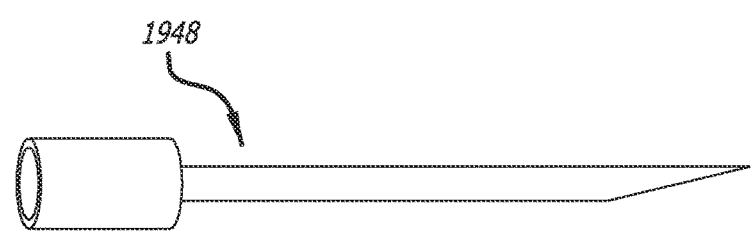
FIG. 19D illustrates a dilator into which the optical-fiber is configured to insert in accordance with some embodiments.
Figure 19E:
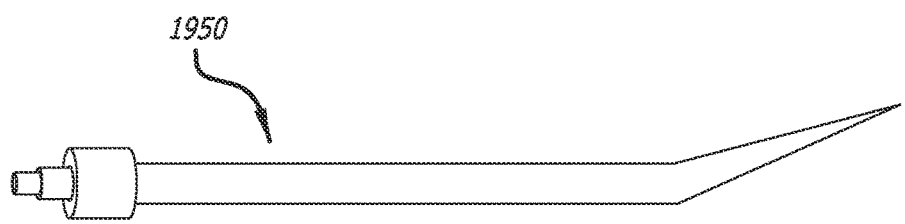
FIG. 19E illustrates a tunneler into which the optical-fiber is configured to insert in accordance with some embodiments.

FIGS. 19A-19E illustrate various medical devices into which the optical-fiber insert 1302 is configured to insert in accordance with some embodiments. The medical device can be an intravascular medical device selected from a catheter 1542 such as a peripherally inserted central catheter ("PICC") as shown in FIG. 19A, a needle 1944 as shown in FIG. 19B, an introducer 1946 as shown in FIG. 19C, a dilator 1948 as shown in FIG. 19D, a tunneler 1950 as shown in FIG. 19E, and a combination of two or more of the foregoing intravascular medical devices loaded into one another. No matter the medical device, the optical-fiber insert 1302 is configured to proximally load into the medical device. However, if the medical device is the tunneler 1950, the optical-fiber insert 1302 is configured to bidirectionally load into either end of two ends of the tunneler 1950.

With the catheter 1542 as an example of the medical device, the catheter 1542 includes a catheter tube 1952, a bifurcated hub 1954, two extension legs 1556, and two Luer connectors 1558 operably connected in the foregoing order. The catheter tube 1952 includes two catheter-tube lumens, the bifurcated hub 1954 has two hub lumens correspondingly fluidly connected to the two catheter-tube lumens, and each extension leg of the two extension legs 1556 has an extension-leg lumen fluidly connected to a hub lumen of the two hub lumens, thereby providing two catheter lumens. As shown in FIGS. 15 and 20, the optical-fiber insert 1302 is configured to proximally load into a lumen of the two catheter lumens by way of a Luer connector of the two Luer connector 1558 of the catheter 1542.

Methods

Methods of the shape-sensing systems 1300 or 1400 or any optical-fiber inserts disclosed herein include at least a method of using the optical-fiber insert 1302. Such a method can include a loading step, a connecting step, and an advancing step.

The loading step includes loading the optical-fiber insert 1302 into an intravascular medical device. Since the medical device can be the catheter 1542, the needle 1944, the introducer 1946, the dilator 1948, or the tunneler 1950, the loading step can include loading the optical-fiber insert 1302 into the catheter 1542, the needle 1944, the introducer 1946, the dilator 1948, the tunneler 1950, or a combination of two or more of the foregoing medical devices loaded into one another. The loading step can occur multiple times during a single medical procedure for a number of medical devices used in the medical procedure, wherein the optical-fiber insert 1302 is a same optical-fiber insert each time of the number of times the loading step occurs.

The connecting step includes connecting the optical-fiber insert 1302 to the console 1304 or 1410 by way of connecting the connector 1526 about the proximal end of the optical-fiber insert 1302 to the complementary connector 1522 of the console 1304 or 1410. Because each connector of the connectors 1522 and 1526 can be a quick-connect connector, the connecting step can include connecting the optical-fiber insert 1302 to the console 1304 or 1410 by way of connecting a quick-connect connector of the optical-fiber insert 1302 to a complementary quick-connect connector of the console 1304 or 1410.

The connecting step can also include automatically instantiating one or more shape-sensing processes of the console 1304 or 1410 for shape-sensing with the optical-fiber insert 1302. The one-or-more shape-sensing processes include sending input optical signals from the optical interrogator 1306 or 1412 to the optical-fiber insert 1302 and receiving FBG sensor-reflected optical signals by the optical interrogator 1306 or 1412 from the optical-fiber insert 1302 during the advancing step.

The connecting step can also include automatically instantiating one or more electrical tip-location processes of the console 1304 or 1410. The one-or-more electrical tip-location processes are configured to locate the distal tip of the optical-fiber insert 1302 by way of electrocardiography, conductance measurements, or impedance measurements using the optional electrical circuitry and componentry of the optical-fiber insert 1302.

The advancing step includes advancing the optical-fiber insert 1302 through a vasculature of a patient independent of or together with the medical device.

The method can further include a sterilizing step. The sterilizing step includes sterilizing the optical-fiber insert 1302 by dry heat, moist heat optionally in combination with pressure, a biocide optionally in combination with pressure, radiation, or a combination thereof before the loading step.

The method can further include a covering step and a removing step. The covering step includes covering the optical-fiber insert 1302 with the disposable cover before the loading step. The removing step includes removing the cover from the optical-fiber insert 1302 when finished using the optical-fiber insert 1302.

The method further can further another but different removing step and a replenishing step. The other removing step includes removing the film or coating from the outer jacket 1630 of the optical-fiber insert 1302 when finished using the optical-fiber insert 1302. The replenishing step includes replenishing the film or coating over the outer jacket 1630 before the loading step.

The method can further include another inserting step and an adjusting step. The other inserting step includes inserting the optical-fiber insert 1302 through the through hole 1840 of the optical-fiber insert holder 1838. The adjusting step includes adjusting a location of the optical-fiber insert holder 1838 over the optical-fiber insert 1302. The optical-fiber insert holder 1838 is configured to hold the optical-fiber insert 1302 in the optical-fiber insert holder 1838 with friction and, thereby, prevent at least proximal movement (i.e., further advancement) of the optical-fiber insert 1302 through the medical device upon reaching a target anatomical location.

The method can further include a ceasing step. The ceasing step includes ceasing to advance the optical-fiber insert 1302 through the vasculature of the patient upon reaching the target anatomical location as determined by the shape-sensing of the optical-fiber insert 1302.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical instrument system for inserting a medical instrument within a patient body, the system comprising:
   the medical instrument comprising an optical fiber having one or more core fibers;
   a stiffening stylet;
   an adjustment mechanism including a proximal collar, a distal collar, and a pair of hinged arms, wherein the proximal collar is coupled to the stiffening stylet, wherein:
      actuation of the adjustment mechanism moves the proximal collar in (i) a proximal direction which moves the stiffening stylet in the proximal direction relative to a distal tip of the medical instrument, or (ii) a distal direction which moves the stiffening stylet in the distal direction relative to the distal tip of the medical instrument; and
   a console including one or more processors and a non-transitory computer-readable medium having stored thereon logic, when executed by the one or more processors, causes operations including:
      providing an incident light signal to the optical fiber,
      receiving reflected light signals of different spectral widths of the incident light signal by the optical fiber,
      processing the reflected light signals associated with the optical fiber, and
      determining a location of the distal tip of the medical instrument within the patient body,
   wherein the medical instrument is configured to be manipulated in order to direct the distal tip in a particular direction.

2. The system of claim 1, wherein:
   a distal portion of the medical instrument is shaped with a predetermined curvature, and
   manipulating the medical instrument includes rotating the medical instrument around a longitudinal axis of the medical instrument in order to direct the distal tip in the particular direction.

3. The system of claim 1, wherein each of the one or more core fibers includes a plurality of sensors distributed along a longitudinal length of a corresponding core fiber and each sensor of the plurality of sensors is configured to (i) reflect a particular light signal of a different spectral width based on received incident light, and (ii) change a characteristic of the reflected particular light signal for use in determining a physical state of the optical fiber.

4. The system of claim 1, wherein the optical fiber is a single-core optical fiber, and wherein the incident light signal is provided in pulses.

5. The system of claim 1, wherein the optical fiber is a multi-core optical fiber including a plurality of the one or more core fibers.

6. The system of claim 1, wherein the logic, when executed by the one or more processors, causes further operations including generating a display indicating the location of the distal tip of the medical instrument within the patient body.

7. The system of claim 1, wherein the medical instrument is one of an introducer wire, a guidewire, a stylet, a stylet within a needle, a needle with the optical fiber inlayed into a cannula of the needle or a catheter with the optical fiber inlayed into one or more walls of the catheter.

8. The system of claim 1, wherein:
   the distal tip of the medical instrument is magnetic, magnetized, metallic, or ferrous,
   the system further included an external magnetic device configured for placement on the patient body, and
   a magnetic field of the external magnetic device attracts or repels the distal tip.

9. The system of claim 1, wherein the stiffening stylet has flexural stiffness that is greater than a flexural stiffness of both of a cladding of the medical instrument and the optical fiber.

10. The system of claim 1, wherein the adjustment mechanism is configured to be actuated mechanically, manually, or electromechanically by a user.

11. The system of claim 1, wherein:
   the medical instrument is a medical instrument assembly comprising:
      a first medical instrument including a lumen; and
      a second medical instrument including the optical fiber,
   the operations further include determining that a curvature is present in a distal tip of the medical instrument assembly, and the curvature is formed from the second medical instrument advancing beyond a distal end of the first medical instrument.

12. The system of claim 1, wherein the medical instrument is configured for insertion within a lumen of a medical device.

13. The system of claim 12, wherein the medical instrument is reusable across multiple medical devices.

14. The system of claim 13, wherein the medical instrument includes a disposable cover configured to cover the medical instrument for each use of the medical instrument.

15. The system of claim 13, wherein the medical instrument includes a film or coating over an outer jacket of the medical instrument, the film or coating configured to be replenishable for each use of the medical instrument.

16. The system of claim 12, wherein the medical instrument is configured to be sterilized by a dry heat, a moist heat optionally in combination with pressure, a biocide optionally in combination with pressure, radiation, or a combination thereof.

17. The system of claim 16, wherein the medical instrument is configured to be re-sterilized between uses of the medical instrument.

18. The system of claim 12, wherein the medical instrument further includes a medical instrument holder configured to accept the medical instrument through a through hole of the medical instrument holder, the medical instrument holder configured to hold the medical instrument therein with friction and prevent proximal movement of the medical instrument while the medical instrument is inserted within the medical device.

19. The system of claim 12, wherein the medical instrument includes electrical circuitry and componentry configured for electrocardiogramhy, conductance measurements, or impedance measurements.

* * * * *